US012108938B2

(12) United States Patent
Perez-Lizano

(10) Patent No.: US 12,108,938 B2
(45) Date of Patent: Oct. 8, 2024

(54) SYSTEM AND DEVICE FOR VISUALIZATION OF AN ENCLOSED SPACE

(71) Applicant: DVL, INC., Las Vegas, NV (US)

(72) Inventor: Edward R. Perez-Lizano, San Diego, CA (US)

(73) Assignee: DVL, INC., Henderson, NV (US)

( * ) Notice: Subject to any disclaimer, the term of this patent is extended or adjusted under 35 U.S.C. 154(b) by 637 days.

(21) Appl. No.: 16/843,779

(22) Filed: Apr. 8, 2020

(65) Prior Publication Data

US 2020/0367722 A1    Nov. 26, 2020

Related U.S. Application Data

(63) Continuation-in-part of application No. 16/528,450, filed on Jul. 31, 2019, now Pat. No. 11,617,498, (Continued)

(51) Int. Cl.
*A61B 1/005*   (2006.01)
*A61B 1/00*    (2006.01)
(Continued)

(52) U.S. Cl.
CPC ........ *A61B 1/0051* (2013.01); *A61B 1/00073* (2013.01); *A61B 1/0052* (2013.01);
(Continued)

(58) Field of Classification Search
CPC .............. A61B 1/0051; A61B 1/00073; A61B 1/00071; A61B 1/0052; A61B 1/05; A61B 1/0676; A61B 1/267; A61B 1/00016; A61B 1/00018; A61B 1/0055; A61B 1/0058; A61M 16/0418; A61M 16/0488;
(Continued)

(56) References Cited

U.S. PATENT DOCUMENTS 3,572,325 A * 3/1971 Bazell ................ A61B 1/00165
                                                      600/164
4,078,555 A * 3/1978 Takahashi ............ A61B 1/0052
                                                      188/72.1
(Continued)

FOREIGN PATENT DOCUMENTS

DE     19524534 C1    6/1996
EP      0778044 A2    6/1997
WO    2011/065963 A1  6/2011

OTHER PUBLICATIONS

International Search Report dated on Aug. 18, 2020, regarding PCT/US2020/027226.
(Continued)

*Primary Examiner* — John P Leubecker

(57) ABSTRACT

A stylet and method of use to intubate a subject. The stylet includes a malleable rod removably housed within the stylet, as well as a flexible proximal portion having a predetermined shape defined by the malleable rod when inserted in the stylet, and a distal tip, wherein the distal tip is capable of deflection when the malleable rod is inserted in the stylet. The stylet further includes a manually operable actuator configured to receive a force from a user at the proximal end of the stylet to control a deflection angle of the distal tip.

6 Claims, 40 Drawing Sheets

Related U.S. Application Data which is a continuation of application No. 14/773,735, filed as application No. PCT/US2014/028737 on Mar. 14, 2014, now Pat. No. 10,368,726.

(60) Provisional application No. 62/830,822, filed on Apr. 8, 2019, provisional application No. 61/883,885, filed on Sep. 27, 2013, provisional application No. 61/794,566, filed on Mar. 15, 2013.

(51) Int. Cl.
| | |
|---|---|
| *A61B 1/05* | (2006.01) |
| *A61B 1/06* | (2006.01) |
| *A61B 1/267* | (2006.01) |
| *A61M 16/04* | (2006.01) |

(52) U.S. Cl.
CPC .............. *A61B 1/05* (2013.01); *A61B 1/0676* (2013.01); *A61B 1/267* (2013.01); *A61M 16/0418* (2014.02); *A61M 16/0488* (2013.01); *A61B 1/00016* (2013.01); *A61B 1/00018* (2013.01); *A61M 2205/3306* (2013.01); *A61M 2205/3569* (2013.01); *A61M 2205/3592* (2013.01); *A61M 2205/502* (2013.01); *A61M 2205/587* (2013.01); *A61M 2205/8206* (2013.01); *A61M 2209/06* (2013.01)

(58) Field of Classification Search
CPC .. A61M 2205/3306; A61M 2205/3569; A61M 2205/3592; A61M 2205/502; A61M 2205/587; A61M 2205/8206; A61M 2209/06
See application file for complete search history.

(56) References Cited

U.S. PATENT DOCUMENTS

| | | | | |
|---|---|---|---|---|
| 4,207,873 | A * | 6/1980 | Kruy | A61B 1/0052 600/146 |
| 4,413,278 | A * | 11/1983 | Feinbloom | A61B 1/317 396/17 |
| 4,488,548 | A | 12/1984 | Agdanowski | |
| 4,637,389 | A | 1/1987 | Heyden | |
| 4,746,043 | A | 5/1988 | Booker | |
| 4,805,595 | A * | 2/1989 | Kanbara | A61B 1/31 600/140 |
| 4,834,069 | A * | 5/1989 | Umeda | A61B 34/71 138/120 |
| 4,942,866 | A * | 7/1990 | Usami | G02B 23/2476 600/148 |
| 5,163,941 | A * | 11/1992 | Garth | A61M 16/0461 24/518 |
| 5,215,092 | A * | 6/1993 | Wray | A61B 8/445 600/445 |
| 5,259,377 | A | 11/1993 | Schroeder | |
| 5,363,838 | A * | 11/1994 | George | A61B 1/2676 128/207.14 |
| 5,454,185 | A | 10/1995 | Love | |
| 5,623,924 | A | 4/1997 | Lindenman et al. | |
| 5,643,221 | A * | 7/1997 | Bullard | A61B 1/0056 604/196 |
| 5,836,894 | A * | 11/1998 | Sarvazyan | A61B 8/12 600/587 |
| 5,873,842 | A | 2/1999 | Brennen et al. | |
| 5,894,369 | A * | 4/1999 | Akiba | G02B 23/2423 600/110 |
| 5,989,182 | A * | 11/1999 | Hori | A61B 1/0052 600/173 |
| 6,132,390 | A | 10/2000 | Cookston et al. | |
| 6,251,080 | B1 | 6/2001 | Henkin et al. | |
| 6,379,310 | B1 | 4/2002 | Mori et al. | |
| D487,844 | S | 3/2004 | Nichols | |
| D496,155 | S | 9/2004 | Londono | |
| 6,823,285 | B1 | 11/2004 | Bartsch et al. | |
| 7,658,708 | B2 | 2/2010 | Schwartz et al. | |
| 7,794,405 | B2 | 9/2010 | Karo et al. | |
| 8,114,026 | B2 | 2/2012 | Leschinsky | |
| 8,416,291 | B2 | 4/2013 | Carrey et al. | |
| 8,534,933 | B2 | 9/2013 | Sherwood | |
| 8,652,033 | B2 | 2/2014 | Berci et al. | |
| 8,659,421 | B2 | 2/2014 | Babineau | |
| D701,504 | S | 3/2014 | Christopher et al. | |
| 8,746,239 | B2 * | 6/2014 | Yoshida | A61M 16/04 128/207.14 |
| 8,827,899 | B2 | 9/2014 | Farr et al. | |
| 9,131,859 | B2 | 9/2015 | Sawanoi et al. | |
| 2002/0022769 | A1 * | 2/2002 | Smith | A61B 1/015 600/188 |
| 2002/0043266 | A1 | 4/2002 | Toti et al. | |
| 2004/0193016 | A1 * | 9/2004 | Root | A61B 1/0052 600/146 |
| 2005/0182297 | A1 | 8/2005 | Gravenstein et al. | |
| 2007/0035042 | A1 | 2/2007 | Sakal et al. | |
| 2007/0074720 | A1 | 4/2007 | Schwartz et al. | |
| 2007/0106208 | A1 | 5/2007 | Uber et al. | |
| 2007/0287961 | A1 | 12/2007 | Parker | |
| 2008/0097161 | A1 * | 4/2008 | Wang | A61B 1/267 600/188 |
| 2008/0236575 | A1 | 10/2008 | Chuda | |
| 2008/0312507 | A1 | 12/2008 | Kim | |
| 2009/0120444 | A1 | 5/2009 | Sapienza | |
| 2009/0322867 | A1 | 12/2009 | Carrey et al. | |
| 2010/0056861 | A1 * | 3/2010 | Spivey | A61B 17/00234 600/106 |
| 2010/0108060 | A1 | 5/2010 | Pecherer et al. | |
| 2010/0168511 | A1 * | 7/2010 | Muni | A61M 25/0152 600/104 |
| 2010/0313895 | A1 | 12/2010 | O'Neil et al. | |
| 2011/0028790 | A1 | 2/2011 | Farr et al. | |
| 2011/0120458 | A1 | 5/2011 | Schwartz et al. | |
| 2011/0160537 | A1 | 6/2011 | Chen | |
| 2011/0196204 | A1 * | 8/2011 | Setty | A61B 1/267 128/200.26 |
| 2011/0207999 | A1 | 8/2011 | Torisawa et al. | |
| 2011/0265789 | A1 | 11/2011 | Gabriel | |
| 2012/0078055 | A1 | 3/2012 | Berci et al. | |
| 2013/0096457 | A1 * | 4/2013 | Qiu | A61B 1/267 600/549 |
| 2013/0104884 | A1 * | 5/2013 | Vazales | A61M 16/0463 128/202.16 |
| 2014/0088361 | A1 * | 3/2014 | Hrayr | A61B 1/05 600/109 |
| 2014/0123976 | A1 * | 5/2014 | Mccormick | A61M 16/0488 128/200.26 |
| 2015/0366445 | A1 * | 12/2015 | Rutgers | A61B 1/2676 128/200.26 |
| 2020/0297957 | A1 * | 9/2020 | Poormand | A61M 16/0418 |

OTHER PUBLICATIONS

International Preliminary Report on Patentability received for PCT Patent Application No. PCT/US2014/028737, mailed on Sep. 24, 2015, 11 pages.

International Search Report and Written Opinion received for PCT Patent Application No. PCT/US2014/028737, mailed on Nov. 20, 2014, 12 pages.

Office Action received for European Application No. 14810570.3, mailed on Dec. 18, 2018, 4 pages.

Supplementary European search report and Search Opinion Received for EP Application No. 14810570.3, mailed on Oct. 24, 2016, 9 pages.

\* cited by examiner

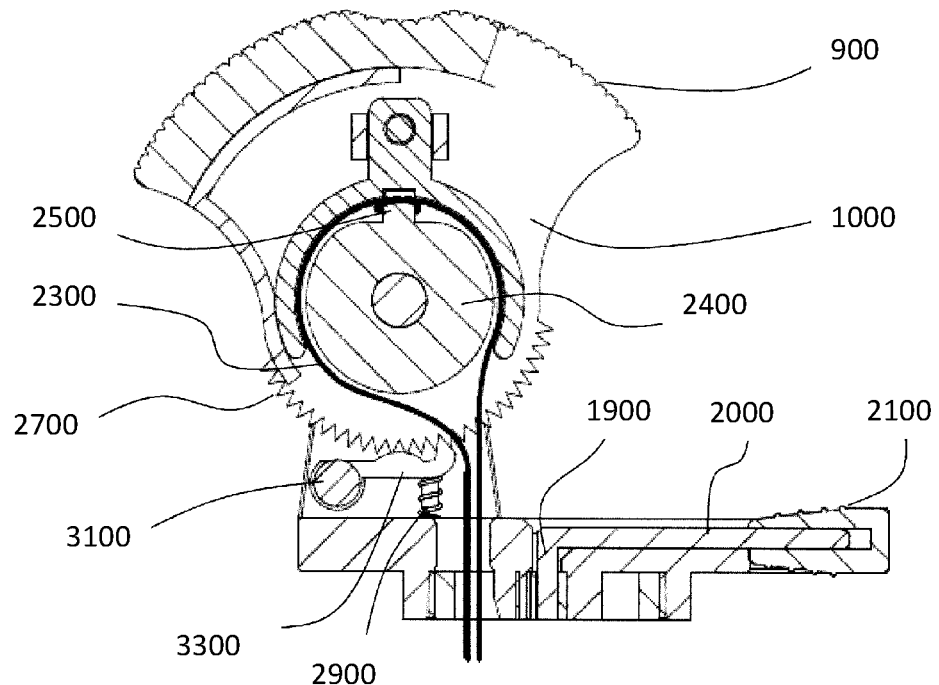
FIG. 23
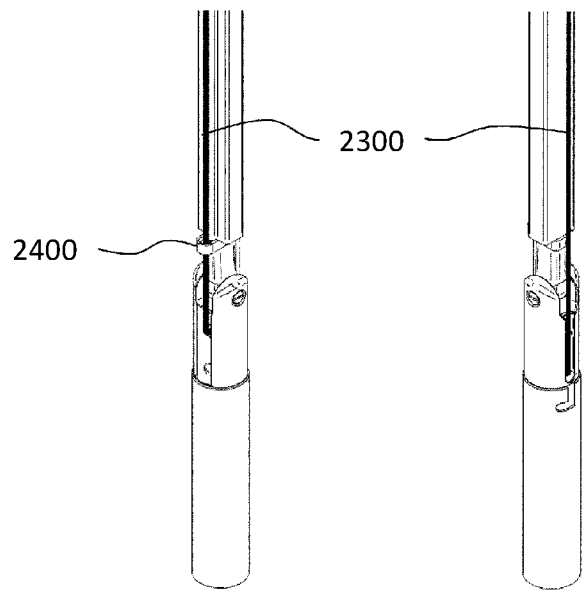 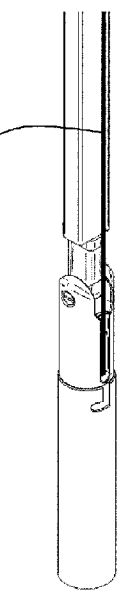
FIG. 24A    FIG. 24B

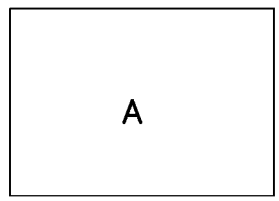 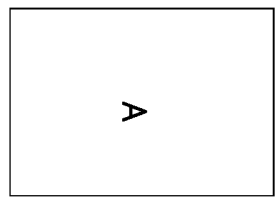 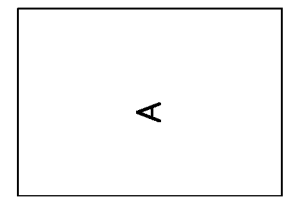
  
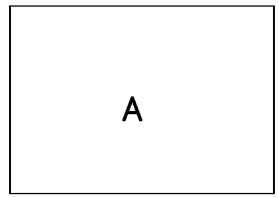 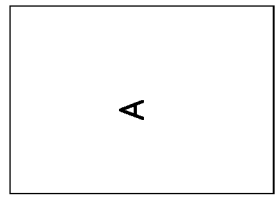 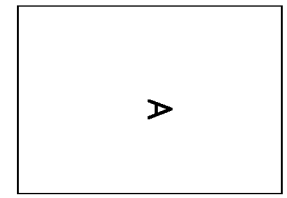
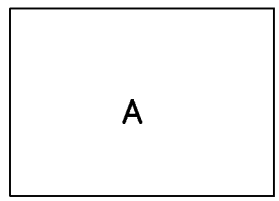 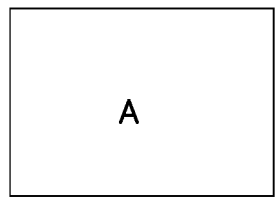 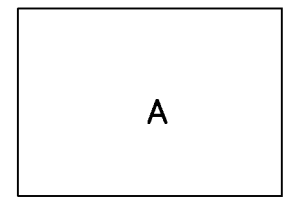
FIG. 34

SYSTEM AND DEVICE FOR VISUALIZATION OF AN ENCLOSED SPACE

CROSS-REFERENCE TO RELATED APPLICATIONS

This application is a continuation-in-part application of U.S. application Ser. No. 16/528,450 filed Jul. 31, 2019, now pending; which is a continuation application of U.S. application Ser. No. 14/773,735 filed Sep. 8, 2015, now issued as U.S. Pat. No. 10,368,726; which is a 35 U.S.C. § 371 National Stage application of International Application No. PCT/2014/028737 filed Mar. 14, 2014, now expired; which claims the benefit under 35 U.S.C. § 119(e) to U.S. Application Ser. No. 61/883,885 filed Sep. 27, 2013 and to U.S. Application Ser. No. 61/794,566 filed Mar. 15, 2013, both now expired. This application also claims the benefit of priority under 35 U.S.C. § 119(e) of U.S. Application Ser. No. 62/830,822 filed Apr. 8, 2019, now pending. The disclosure of each of the prior applications is considered part of and is incorporated by reference in the disclosure of this application.

FIELD OF THE INVENTION

The disclosure relates to intubation devices, and more particularly to endotracheal tubes and stylets for use with endotracheal tubes.

BACKGROUND

A wide variety of devices are described in the art that facilitate viewing of confined spaces. Frequently, such devices rely upon fiber optic conduits to transfer the image from the distal end of the fiber optic conduit inserted into the confined space to the operator at the proximal end of the fiber optic conduit. Such confined spaces frequently lack illumination and consequently such viewing systems often provide an illumination source. Examples of such commercially available fiber optic viewing devices include bore scopes, endoscopes, and the like. However, such devices are frequently complex involving a viewing system integral with the fiber-optic channel. Due to the complexity of these devices and the specialized nature of their applications, they are often very expensive restricting their use to professionals whose work demands the use of such instrumentation.

A common procedure that may utilize fiber optic viewing system is endotracheal intubation which is a common technique that is used when an individual must be ventilated such as after receiving a general anesthetic. The technique consists of placing an endotracheal tube (i.e. a flexible, plastic tube) into the patient's trachea to ventilate his/her lungs. During intubation, the endotracheal tube (ET) must be inserted past the patient's teeth and tongue and then past the epiglottis and the vocal cords into the trachea.

Devices have been developed that utilize flexible fiberoptics, either alone or in conjunction with endotracheal tubes, to perform intubation. However, such scopes are awkward to use due to their length and inability to shape the ET. Additionally such devices are very costly which limits access to these devices. As such, there is a need for a system that allows illumination and viewing of the respiratory tract during intubation which is also flexible and easily adjustable to ensure ease of intubation.

During tracheal intubation, an ET must be inserted into a patient's airway. In a typical intubation process a clinician standing above/behind the head of the supine patient will use a laryngoscope to move the tongue and epiglottis out of the way and then insert an ET through the patient's vocal cords into the trachea. Once the ET is correctly positioned in the trachea, commonly a cuff on the ET will be inflated to allow positive ventilation of the patient. It is necessary to ensure accurate placement of the ET in the trachea and to avoid incorrect placement of the ET e.g. into the esophagus rather than into the trachea. The patient is commonly anesthetized and apneic, so the intubation procedure has to be completed rapidly, and it is advantageous to confirm correct placement of the ET quickly and accurately so that ventilation can begin.

Location of the ET can be determined using a number of methods, including visualization, capnography, and X-ray location of the tube, alongside physical examination methods such as auscultation of the chest and epigastrium, and visualization of thoracic movement. However, many of these methods of determining ET placement are not sufficiently reliable to be used as sole techniques to correctly determine ET location. Direct visualization of the ET passing through the vocal cords into the trachea is the most reliable method of quickly and accurately determining correct placement of the ET.

In some cases, the clinician performing the intubation may be able to directly visualize placement of the ET, but this is not always possible, depending on the particular anatomy of the patient. For example difficulties may be encountered where the patient has restricted neck flexibility, or is obese. For such patients, video laryngoscopes are a well-known option for facilitating intubation. However, video laryngoscopes can have drawbacks. The video apparatus is typically provided at an intermediate location along the laryngoscope blade, the distal end of the blade can partially obstruct the field of view. Also the ET itself may obstruct the view of the vocal cords and trachea as it advances past the end of the laryngoscope. Video laryngoscopes tend to be expensive, which further limits their use as single use devices.

The act of placing the ET offers its own difficulties, even when it can be visualized clearly. Typically an ET is made from semi-rigid polymer, and has a gentle curve to align with the airways of the patient. However, patient anatomy may require that the ET has a specific shape, for example, a sharper bend at the distal end, to aid insertion through the vocal cords into the trachea. Because the material of the ET is generally flexible and does not retain shape when bent, a stylet may be used with the ET. A stylet is an elongate device inserted into an ET to hold it in a specific—perhaps altered—shape to facilitate intubation. Stylets may also provide additional rigidity to the ET to aid navigation of the ET into the desired location. Some known stylets can be inserted into the ET and shaped by the clinician so the form of the ET is retained before and during insertion of the combined devices into the patient's airway. However setting the shape of the stylet before intubation can lead to undesirable delays during the intubation procedure where the set shape turns out to be not quite right for the patient's anatomy.

Over the last several years, indirect laryngoscopy has replaced direct laryngoscopy as a high success alternate method of laryngoscopy, especially in patients presenting with a "difficult airway". See (Video-assisted Laryngoscopy) section from "Practice Guidelines for Management of the Difficult Airway" ASA-American Society of Anesthesiologists, 2013.

In contrast to direct laryngoscopy, with indirect laryngoscopy the laryngoscopist visualizes the patient's vocal cords by means other than obtaining a direct line of sight. This is usually accomplished with a video laryngoscope or a bronchoscope.

CMOS-equipped bronchoscopes and video laryngoscopes such as U.S. Pat. No. 8,790,250B2 to Peterson and US2010261967A1 to Pacey offer high resolution images without orientation issues and are quickly replacing their fiberoptic and mirror/prism device equivalents. With video laryngoscopy, the laryngoscopist is able to visualize the larynx with a high success rate. However, a new set of problems are realized when comparing indirect to direct laryngoscopy: 1) blood, secretions, and fogging can all obscure the cameras view on these single view video laryngoscopes; 2) a standard C-shaped ET passing through a channeled video laryngoscope blade is incorrectly angled for placement along the patient's tracheal axis since the patient's tongue is not displaced as it is in direct laryngoscopy and the video laryngoscope blade shape is hyperangulated to view anterior vocal cords with high success. The ET must now retroflex to take on an "S shape" in order to be successfully aligned with the patient's tracheal axis for intubation; 3) soft tissue damage from the ET as it passes without direct or indirect observation through the patient's oropharynx. See (Video-assisted Laryngoscopy) section from "Practice Guidelines for Management of the Difficult Airway" ASA—American Society of Anesthesiologists, 2013; and 4) correct placement of the ET within the trachea is not able to be verified visually. With bronchoscopy, the following problems exist: 1) blood, secretions, and fogging can all obscure the cameras view on these single view bronchoscopes; 2) the bronchoscope can be steered into the trachea. However, the ET still needs to be "railroaded" over it in a "blind" procedure which can lead to laryngeal inlet injury or failed intubation; 3) the bronchoscope is unable to flex or retroflex a standard ET.

Another problem encountered during video laryngoscopy or bronchoscopy is that the patients cardiorespiratory data is not incorporated into the video monitor used for laryngoscopy. The laryngoscopist either has to make available a second monitor or shift attention away from the laryngoscopy monitor or use only auditory cues such as the pitch change associated with a falling oxygen saturation on the pulse oximeter. Alternately, a second provider can call out the oxygen saturation values and other cardiorespiratory parameters. None of these solutions are ideal as they all require extra monitoring equipment, personnel, or simply do not provide the data to the clinician in a timely manner without distraction. Only 67% of the population can detect a pitch change corresponding to a 1% fall in oxygen saturation and 11% cannot detect a pitch change until there is a change with every beat. See (Can People Hear the Pitch Change on a Variable Pitch Pulse Oximeter) Journal of Clinical Monitoring 1992 Jul. 8 (3): 198-200. Due to this problem the video monitor for this device may incorporate cardiopulmonary data into the video display.

Portability is also an important feature lacking in many video airway device designs. This feature allows the device to be easily used in austere conditions inside or outside of a hospital.

SUMMARY OF THE INVENTION

The present invention provides a device and system which combines a stylet with imaging and display capabilities to enable visualization of confined spaces. Accordingly, in one aspect, the invention provides an imaging system. The imaging system includes: a) a stylet having a distal end, a proximal end and a deflectable section disposed therebetween; and b) an image acquisition element disposed toward the distal end of the stylet. The stylet includes: i) a first shaft having a distal end and a proximal end, the proximal end of the first shaft being coupled to a first pressure receiving element at the proximal end of the stylet; and ii) a second shaft having a distal end and a proximal end, the distal end of the second shaft being coupled to the distal end of the first shaft at the distal end of the stylet, and the proximal end of the second shaft being coupled to a second pressure receiving element disposed distal to the first pressure receiving element at the proximal end of the stylet, the second pressure receiving element slidably coupled to the first shaft, wherein application of opposing forces to the first and second pressure receiving elements produces a deflection in the deflectable section. In various embodiments, the imaging system further includes an image conduit coupled to the image acquisition element and traversing along the length of the first or second shaft and optionally includes a coupling for operably engaging a display of the system. In another embodiment, the image acquisition element is in wireless communication with the display. In various embodiments, the system further includes a malleable rod removably disposed within a lumen, channel, groove, or recess of the first or second shaft.

In another aspect, the invention provides an intubation device. The intubation device includes: a) a stylet having a distal end, a proximal end and a deflectable section disposed therebetween; and b) a malleable rod removably disposed within a lumen or recess of the stylet extending along its length. The stylet further includes: i) a first shaft having a distal end and a proximal end, the proximal end of the first shaft being coupled to a first pressure receiving element at the proximal end of the stylet; and ii) a second shaft having a distal end and a proximal end, the distal end of the second shaft being coupled to the distal end of the first shaft at the distal end of the stylet, and the proximal end of the second shaft being coupled to a second pressure receiving element disposed distal to the first pressure receiving element from the user's perspective at the proximal end of the stylet, the second pressure receiving element coupled to the first shaft, wherein application of opposing forces to the first and second pressure receiving elements produces angular deflection in the deflectable section. In various embodiments the intubation device further includes an illumination source disposed toward the distal end of the stylet which may be arranged as an array.

In another aspect, the invention provides an imaging system having: a) a stylet having a distal end and a proximal end; b) an image acquisition element disposed toward the distal end of the stylet; and c) a malleable rod removably disposed within a lumen or recess extending along the length of the stylet. The stylet further includes: i) a first shaft having a distal end and a proximal end; and ii) a second shaft having a distal end and a proximal end, the distal end of the second shaft being coupled to the distal end of the first shaft at the distal end of the stylet, and wherein the first shaft and the second shaft are of different lengths. In various embodiments, the imaging system further includes an image conduit coupled to the image acquisition element and traversing along the length of the first or second shaft and optionally includes a coupling for operably engaging a display of the system. In another embodiment, the image acquisition element is in wireless communication with the display. In various embodiments, the system further includes a malleable rod removably disposed within a lumen or recess of the first or second shaft.

In another aspect, the invention provides a kit. The kit may include an imaging system or intubation device as described herein. The kit may further include instructions for obtaining images of a confined space, such as an airway. In some embodiments, the kit further includes one or more spacer elements.

In another embodiment, the invention provides a method of intubating a subject. The method includes: a) inserting the stylet of the system of claim 1 into an ET; b) insert the stylet and the ET into the airway of the subject; c) visualizing the airway of the subject via the image acquisition element; d) inserting the stylet and the ET into the trachea of the subject; and e) removing the stylet from the subject's trachea, thereby intubating the subject. In embodiments, the method may further include confirming correct depth of placement of the ET in the trachea of the subject. Additionally, a malleable rod may be inserted into the first or second shaft of the stylet and bent to a desired curvature before inserting the stylet in to the airway.

In yet another embodiment, the invention provides a method of imaging a confined space. The method includes applying opposing forces to the first and second pressure receiving pads to generate a deflection in the stylet of the present invention, inserting the stylet into the confined space, and visualizing the space via an image acquisition element before, during or after insertion of the device into the confined space, thereby imaging the confined space.

In various embodiments, the invention provides a stylet for guiding an ET during intubation. The present invention includes a number of individual proposals relating to various features of a stylet, each of which may be considered individually or in combination with any other of the proposals herein.

In various aspects, the disclosure provides a single or double lumen ET that includes: a tube having a lumen; optionally a connector operable to connect the tube to a breathing circuit; and one or more bumps, ribs, fins, or projections on an inner wall of the tube for contacting the distal end of a stylet or endoscope disposed within the tube to reversibly secure the stylet or endoscope in a set position during deflection and minimize the impedance to airflow through the tube during operation. In various embodiments, the tube has a flexible bending segment located at a distal end of the tube to allow angular deflection coinciding with angular deflection of the stylet or otherwise bending of the tube while preventing kinking of the tube.

In various embodiments, the ET may include markings or color coding for identification of depth of insertion when the ET is advanced in an intubation conduit to identify the exact depth of insertion where the endotracheal tube's flexible bending segment has exited the intubation conduit and is able to be deflected without impedance. In some embodiments, the ET includes a power supply and wiring in electrical communication with an illumination source and an image acquisition element coupled to a distal end of the tube, and optionally multiple wavelength light emitters and sensors in electrical communication with the power supply, the sensors being coupled with a wall of the tube and positioned longitudinally and/or radially along the wall of the tube for the purpose of obtaining oxygen saturation readings and cardiopulmonary data from a patient. In various embodiments, the ET includes one or more spatial position sensors disposed at any point along the length of the tube or the connector and optionally a wireless transmitter for transmission of image acquisition data, oxygen sensor data, and/or spatial position data to a display monitor. In embodiments, where the ET is double lumen ET, the tracheal lumen and the bronchial lumen are substantially the same length longitudinally to enable rapid use of an endo scope or a stylet in either lumen without adjustment.

In another aspect, the disclosure provides a method of manufacturing the ET of the disclosure. The method includes the ET, wherein the flexible bending segment is manufactured as a locally thinned segment to allow angular deflection while preventing kinking of the tube; wherein the flexible bending segment is manufactured as a concertina or bellows to allow angular deflection while preventing kinking of the tube; wherein the flexible bending segment is manufactured of a different material than the remaining portion of the endotracheal tube to allow angular deflection while preventing kinking of the tube, and/or wherein the flexible bending segment is manufactured as a flexible wire reinforced segment to allow angular deflection while preventing kinking of the tube.

In another aspect, the invention provides a stylet for guiding an endotracheal tube during intubation. The stylet includes: a flexible stylet body having an angularly deflectable tip located at the distal end of the flexible stylet body, the angularly deflectable tip moveable in two opposing directions from the distal end of the flexible stylet body, wherein the flexible stylet body includes a first thermoset plastic coating covering stylet components located in an attachable endotracheal tube or attachable video endotracheal tube proximal to the angularly deflectable tip of the stylet; and an actuator control mechanism configured with one or more pressure receiving elements to receive pressure from the hand of a user and deliver forces to one or more flexible shafts of the flexible stylet body for controlling the deflection angle of the angularly deflectable tip.

In various embodiments, the stylet includes a second thermoplastic elastomer covering stylet components located in an attachable endotracheal tube or attachable video endotracheal tube, the second thermoplastic elastomer covering having a distal opening for an image acquisition element and an illumination source.

In various embodiments, the stylet includes an actuator control mechanism. In embodiments, the actuator control mechanism includes a wheel having a plurality of discrete stop points which provide locking of the angularly deflectable tip at discrete incremental deflection angles by including releasably interlocking elements that prevent transition of the stylet back to the relaxed configuration while the stylet is being deflected. In embodiments, the actuator control mechanism includes a plurality of discrete stop points which provide locking of the angularly deflectable tip at discrete incremental deflection angles by including releasably interlocking elements that prevent transition of the stylet back to the relaxed configuration while the stylet is being deflected.

The disclosure provides a steerable stylet, optionally preloaded in a single or double lumen ET. The stylet includes a flexible stylet body; at least one flexible shaft of the flexible stylet body for controlling an angularly deflectable tip located proximate to a distal end of the stylet, the shaft(s) being disposed in a lumen or recess of the stylet body thereby forming an elongated unitary shaft, the angularly deflectable tip being movable via a deflectable section from the longitudinal axis of the distal end of the stylet; and an actuator control mechanism having a control mechanism for engaging a user's hand and controlling the deflection angle of the angularly deflectable tip. Within the deflectable section is a deflection point at which point an angle is generated in the stylet body (as opposed to a continuous bend) to angularly deflect the deflectable tip to allow steering of the tip though the airway. Upon deflection at the deflection point, the angularly deflectable tip is deflected with respect to the longitudinal axis of the stylet shaft through a deflection zone which defines the range of motion and deflection angle.

In embodiments, the stylet comprises a flexible stylet body having an angularly deflectable tip located at a distal end of the flexible stylet body. Angularly deflectable refers to the fact that the tip angularly deflects at a defined deflection point. By allowing the tip to angularly deflect at a deflection point, rather than providing gradual bending along a deflectable portion of the stylet, it is possible to accurately adjust the direction of the stylet's distal tip, without affecting the shape of the rest of the flexible stylet body by e.g. additional unwanted bending along the length of the stylet.

In embodiments, the pivotable tip is rigid, and affixed to the distal end of stylet body at a pivot hinge. The pivot angle of the tip is defined as the angle between the longitudinal axis of the distal end of the stylet body, and the longitudinal axis of the tip. The pivotable tip is pivotable in two opposing directions relative to the direction of the longitudinal axis of the distal end of the stylet body, and/or relative to a neutral or rest position of the tip. This pivot range of the tip may be at least ±10°, at least ±20°, at least ±30°, at least ±40°, at least ±50°, at least ±60°, at least ±70°, at least ±80°, at least ±90°, at least ±100°, at least ±110°, at least ±120°, at least ±130°, at least ±140°, at least ±150°, at least ±160°, at least ±170°, or at least ±180°, to allow a degree of deflection suitable for guiding the end of an ET into the desired location. The range of movement of the tip may or may not be symmetrical, of course. A range of at least ±10° therefore includes a tip which is movable between, e.g. −10° and +15°.

The pivot range of the tip may be as large as ±45°, ±50°, ±60°, ±70°, ±80°, ±90°, ±100°, ±110°, ±120°, ±130°, ±140°, ±150°, ±160°, ±170°, or ±180° from the longitudinal axis of the distal end of the stylet body. A pivot range of ±90° from the longitudinal axis of the distal end of the stylet body means that the tip can pivot through a 180° pivot range, from a position substantially perpendicular to the distal end of the stylet body on one side of the body (−90°), through a position substantially parallel to the longitudinal axis of the distal end of the stylet body (0°), to a position substantially perpendicular to the distal end of the stylet body on the opposing side of the stylet body (+90°). A pivot range of ±360° means that the tip can pivot through a 360° pivot range, from a position substantially parallel to the distal end of the stylet body on one side of the body (−180°) through a position which is substantially parallel to the longitudinal axis of the distal end of the stylet body (0°) to a position substantially parallel to the longitudinal axis of the distal end of the stylet body on the opposing side of the stylet body) (+180°). Advantageously, the stylet allows for movement of the stylet tip through a wider range of motion than typical known stylets. Furthermore, more accurate control of the distal end of the ET into which the stylet in inserted during an intubation procedure can be achieved.

In embodiments, the pivotable tip is operable to move omnidirectionally, is rotationally moveable with 3, 4, 5, 6, 7, 8, 9, 10, 11, 12, 13, 14, 15, 16, 17, 18 or more flexible shafts, and is movable within a pivot angle range of about 0° to about 5°, 10°, 20°, 30°, 40°, 50°, 60°, 70°, 80°, 90°, 100°, 110°, 120°, 130°, 140°, 150°, 160°, 170° or 180° with respect to the distal end of the stylet.

In embodiments, the invention relates to a stylet tip portion which can be deflected from a rest or neutral position relative to the stylet body, especially at a local flexure portion between the body and tip portion such as a pivot, such as in the first proposal above. The tip deflection is controlled by a control mechanism having an actuator. The actuator may be disposed at a proximal end of the stylet body, for ease of access by a clinician during an intubation procedure. The actuator may comprise a rotatable, pivotable or slidable control portion. For example, it may comprise a ball, wheel, dial, lever or joystick. Preferably the actuator of the control mechanism is hand-operated, however various electronically-controlled mechanisms are also contemplated. For example, where the actuator comprises a rotatable control portion, this could be connected to a motor for driving rotation of the control portion, the motor being controlled by an electronic control module.

In embodiments, the actuator control mechanism is connected to the angularly deflectable tip by one or more control connectors, one or more flexible shafts that form an elongated unitary shaft that may be disposed within the flexible stylet body. Preferably, there is at least a first portion of each individual shaft in operable connection to the actuator control mechanism and the other side of each individual shaft in operable connection to the angularly deflectable tip. By applying unequal forces to the first portion of each individual shaft, the tip can be angularly deflected through the deflection range at a deflection point within the deflectable section. Typically, the deflectable section is disposed at a distal region of the shaft body and in proximity to the distally disposed angularly deflectable tip.

Pivotable refers to the fact that the tip pivots at a defined pivot point. By allowing the tip to pivot at a pivot point, such as the deflection point of the deflectable section, rather than providing gradual bending along a generally deflectable portion of the stylet, it is possible to accurately adjust the direction of the stylet tip, without affecting the shape of the rest of the stylet body by e.g. additional unwanted bending along the length of the stylet. In embodiments, the deflection section is less than about 5, 4, 3, 2 or 1 cm in length and located within 10, 9, 8, 7, 6, 5, 4, 3, 2 or 1 cm proximal to the distal end of the shaft body. In such embodiments, the pivotable tip is operable to move omnidirectionally, is rotationally movable with 3, 4, 5, 6, 7, 8, 9, 10, 11, 12, 13, 14, 15, 16, 17, 18 or more flexible shafts, and is movable within a pivot angle range of about 0° to about 5°, 10°, 20°, 30°, 40°, 50°, 60°, 70°, 80°, 90°, 100°, 110°, 120°, 130°, 140°, 150°, 160°, 170° or 180° with respect to the distal end of the stylet.

The actuator may connected to the pivotable tip by one or more control connectors, such as flexible lines such as wires (henceforth "wires"). Preferably, there is at least a first portion of the wire connected to one side of the pivotable tip, and a second portion of the wire connected to the opposing side of the tip. In this way, by applying tension to the first wire portion, the tip can be moved in a first direction. By applying tension to the second wire portion, the tip can be moved in a second direction. The first and second wire portions may be part of a single piece of wire. Alternatively, the first and second wire portions may be two separate wires.

Preferably, the control mechanism provides a plurality of discrete predetermined stop points for the actuator. For example, the actuator may include first and second relatively moveable members, wherein the first member has e.g. a series of notches which act as discrete stop points by engagement with a portion of the second of the relatively moveable members. Preferably, the first relatively moveable member is a rotatable control portion having a series of notches which sequentially engage with a detent of the second relatively moveable member as the control portion is rotated. These stop points can provide locking of the pivotable tip at discrete incremental pivot angles. By providing discrete stop points, a person operating the control mechanism can set the pivot angle of the tip to a particular angle, and keep the tip locked at this angle without further interaction by the operator; the operator may let go of the actuator. This is advantageous in comparison to known systems which require that the control mechanism is continuously held at the correct position to give the desired stylet shape. The stop points may provide incremental pivot angle changes of between 1° and 20°. For example, the stop points may provide incremental pivot angle changes of 1°, 2°, 5°, 10° or 15°.

Where the second relatively moveable member has a detent, the detent may be moveable to allow it to move into and out of engagement with notches on the first relatively movable member. Preferably, the first and second members are biased into engagement e.g. of one or more detents with one or more notches. Conveniently, one or both members e.g. member having the detent, may be attached to a spring member which acts to urge the detent into engagement with the notches. The detent may preferably be shaped to help prevent jamming of the actuator. For example, the detent may have a protrusion which restricts the distance the detent can enter into the notches on the first relatively moveable member. Preferably the detent is pivotable, and can pivot into and out of engagement with the notches.

The actuator may have one or more end stops which restrict a movement range of the actuator and correspondingly the pivot range of the pivotable tip.

Providing such an end stop can prevent over-bending of the tip, which may be desirable to prevent damage to the stylet and/or the ET. The end stops may be formed as part of a sliding arrangement. For example, the end stops may be formed as end stops of a groove in which a pin slides. One proposed configuration includes a recessed slot formed in the dial of the actuator, into which a pin projecting from the actuator body is located. On rotation of the dial, the pin slides along the slot until it reaches an end stop at one end of the slot, thereby preventing further rotation of the dial, and corresponding movement of the tip. The skilled person will be aware of a range of other suitable configurations which would be suitable for restricting the movement range of the actuator. For example, a simple modification of the above proposed configuration is the pin may be formed on the dial, and the slot may be formed on the actuator body.

As envisioned herein, stylet of the invention may further include one or more bumps, ribs, fins or projections on the distal end of the stylet body for contacting a wall of an ET, e.g., contact a lumen wall of the tube. The allows securement of the stylet in a set position during pivoting movement. It also allows impedance of airflow through the ET during operation to be minimized. For example, the bumps, ribs, fins or projections may be spaced around the circumference of the stylet body and include recesses between them which allow gas to continue flowing through the ET and external to the stylet body during operation.

As provided herein, the stylet may have an image acquisition element disposed on the pivotable tip. Preferably the image acquisition element is disposed at the distal end of the tip portion, and is arranged to capture images in a direction along the longitudinal axis of the tip, distal to the tip. Where the stylet is used in combination with an ET, the image acquisition element may be arranged to capture images from the end of the ET. However, it is contemplated that for some uses, the image acquisition element may be arranged to capture images in a direction radial to the longitudinal axis of the stylet. Providing an image acquisition element in the stylet has a number of benefits. Because of the wide range of movement of the stylet tip, locating an image acquisition element in the tip offers a large possible field of view. The tip can be adjusted as desired to better capture the desired field of view. Furthermore, because the stylet will typically be located within the ET during intubation, placement of the image acquisition element at the stylet tip allows for visualization of the vocal cords and trachea of a patient as the ET passes through the vocal cords.

Accordingly, correct placement of the tube can be reliably determined with minimal obstruction to the field of view.

The stylet may comprise a preforming rod, (also referred to herein as a 'malleable rod') removably disposed within a lumen of the stylet body. Typically the stylet body is tubular with a central lumen. Such preforming rods are known as such and are of material and dimensions selected for ready plastic deformation.

Providing a preforming rod allows a clinician to bend the stylet into a desired shape to assist with intubation. However, the rod is removable to facilitate certain procedures such as intubation with a hyperangulated video laryngoscope blade, nasal intubation, intubation through an intubating oropharyngeal airway, or intubation through a supraglottic airway device. The rod may have a rectangular cross section, which can increase the stylet's resistance to torsion, however this is not essential, and rods with other cross sections, (e.g. square, circular or otherwise) may also be used. An oblong cross section is desirable to promote preferential bending in a single plane. The material of the preforming rod may be of a malleable material such as metal (which may be metal alloy), as is known, for example, titanium, aluminum, or steel.

Preferably, the rod is made of titanium. The rod may be substantially the same length as the stylet body.

Conveniently, the rod may have a handle at the proximal end to increase ease of insertion and/or removal of the rod from the lumen of the stylet body. The handle portion may have a textured (e.g. ridged) gripping portion to further assist in insertion/removal of the rod from the lumen of the stylet body.

In embodiments, the stylet may have an attaching portion located at a proximal end of the stylet body, adapted for attachment to an ET connector. ET connectors are well-known in the art, and are used to connect an ET to ventilation apparatus. Typically, they will be a single component having a tapered portion for removable insertion into an ET, a flange to aid grip, and a ventilation attachment portion for attaching to the ventilation apparatus.

Preferably, the attaching portion of the stylet is adapted to connect to the ventilation attachment portion of an ET connecter. The attaching portion of the stylet may therefore be a plug portion adapted to provide a plug fit connection to the corresponding ET connector.

Accordingly, with this configuration, the stylet can be attached to an ET via attachment to an ET connector. This is not essential, but is advantageous, as it helps to prevent relative longitudinal movement of the stylet with respect to the ET during intubation, and can additionally help to prevent the stylet from protruding from the distal end of the ET during intubation, which may be undesirable as such protrusion can cause damage to the patient's airways. Preferably, the attaching portion is integral with a body or retaining housing of the actuator of the stylet.

The stylet may have a port for connection to an oxygen line. Preferably, the port passes through a body or retaining house of the actuator of the control mechanism, into a space defined by an attaching portion of the stylet. Such a configuration can allow oxygen, air, or medication to be delivered directly into an ET to which the stylet is connected via an ET connector.

In various embodiments, the stylet may be attached to a single or double lumen ET. This may be done by attachment of the stylet and ET through the attaching portion located at a proximal end of the stylet body and a proximally disposed ET connector of an ET.

The disclosure further provides an ET which is particularly suitable for use with stylets of the type proposed herein, but which may also be used in combination with other stylets. General features of an ET include the following, which may be used in our proposals and are familiar to the skilled person. This means that a clinician using the ET will be familiar with the overall configuration of the ET, which is helpful for successful intubation in the limited time available. Accordingly, the ET has a body comprising a flexible, hollow tube having a distal end for insertion into a patient's trachea during intubation, and a proximal end, which the clinician may hold and use to direct movement of the distal end of the tube. The proximal end is typically attached to an ET connector for connection of the ET to ventilation apparatus after the intubation procedure has been completed. The ET connector may be removable so that it can be removed to allow the ET to be cut to length after insertion, and then subsequently replaced to allow connection of the ET to ventilation apparatus.

The tube may have an inflatable cuff which can be inflated during the intubation procedure once the ET is in place, to hold the tube in the correction position to protect from pulmonary aspiration, and permit positive pressure ventilation of the patient. Where the tube has an inflatable cuff, this is connected to an inflation line through which air may be pumped to inflate the cuff. At least a portion of the inflation line may be recessed into the wall of the ET.

The distal end of the tube may have a beveled tip, to aid in insertion of the tube between the vocal cords of the patient. Typically, the distal end of the tube will also have a subsidiary opening to provide an alternate gas passage in the case of occlusion of the main opening, e.g. an opening known as a Murphy eye formed in a sidewall of a tip portion of the tube.

In embodiments, the ET may have multiple such subsidiary air openings, for example two Murphy eyes. The openings may be formed in opposing sidewalls of a distal tip portion of the ET. Where there are multiple openings, they can be smaller whilst retaining the same total flow area for the passage of gas in comparison to typical known tubes having only one Murphy eye. The advantage of providing multiple, smaller openings or Murphy eyes is that it can prevent a stylet tip from passing through or catching in these openings.

In embodiments, an ET has a bending portion or local flexure at the distal end of the tube. A bending portion is a portion of the tube which is more susceptible to bending under a bending force than the body of the ET. The bending portion may extend out to the distal tip of the ET. Alternatively, the bending portion may be a portion at the distal end region of the ET, but intermediate the body and a less flexible distal tip portion of the tube. The exact location and length of the bending portion will depend on a number of factors, as discussed below. Preferably, the position of the bending portion is selected to align with the expected position of the pivot point of the pivotable tip of the stylet of the first aspect when the stylet and ET are used together.

The flexible bending segment may be a concertina portion or bellows, i.e. with one or more wall corrugations to enable easier flexing at that location. Alternatively or additionally, the flexible bending segment may have a portion made from a different material to the material of the rest of the body of the ET. The flexible bending segment may be locally thinned in comparison to the thickness of the rest of the body of the tube. The flexible bending segment may be manufactured as a flexible wire reinforced segment to allow curved or angular deflection while preventing kinking of the ET. The entire ET may also be manufactured as a flexible wire reinforced ET to allow angular deflection while preventing kinking of the ET at any point along its length. Each of these features, which may be used separately or in combination, can make the flexible bending segment more susceptible to bending than the rest of the body of the ET. Accordingly, when used in combination with a stylet of the first aspect of the present invention, the distal end of the ET may be easier to direct by control of the angularly deflectable tip of the stylet. This can allow the ET to be more easily guided into the correct location by the clinician.

In another embodiment the stylet may include one or more gears in operable connection to a dial of the actuator. The one or more gears are configured to interact with the flexible shafts or control wire(s) disposed within the stylet body. The one or more torque generating gears to allow the amount of force required by the operator to manipulate the stylet to be reduced thereby enabling the deflection of a standard, unmodified, endotracheal tube.

The invention also provides a single or double lumen ET having one or more bumps, ribs, fins or projections on an inner wall of the tube for contacting the distal end of a stylet disposed within the tube to secure the stylet in a set position during pivoting movement and minimize impedance of airflow through the tube during operation. The tube may be used with a laryngoscope having an oxygen line and suction port at its distal end, supraglottic airway, or video ET.

In embodiments, an ET of the invention may include power and wiring in electrical communication with multiple wavelength light emitters and sensors, the sensors being coupled with a wall of the single or double lumen ET and positioned longitudinally and/or radially along the length of the wall for the purpose of obtaining oxygen saturation readings and cardiopulmonary data from a patient.

The invention further provides an intubation kit, including a stylet, optionally in combination with an ET. The kit may include a stylet of the disclosure and/or an ET (single or double lumen) of the disclosure.

The kit can be used to perform an intubation process by a) inserting the stylet into the ET, b) inserting the stylet and ET into the airway of a patient, c) visualizing the airway of the patient, preferably using an image acquisition element of the stylet, d) guiding the ET and stylet through the vocal cords of the patient into the trachea, and e) removing the stylet from the ET. Such a kit can offer increased ease of intubation, in particular for patients with difficult airways.

An intubation method using the present stylet, ET or intubation kit is a further aspect of the invention.

BRIEF DESCRIPTION OF THE FIGURES

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIG. 23 is a sectional view of the actuator control mechanism of FIG. 21.

FIGS. 24-24B, 24(A) and 24(B) show two different perspective views of the angularly deflectabletip of a stylet.

FIG. 34 illustrates use of a spatial orientation/position sensor for the double lumen ET of FIG. 32 or 33 and sets for diagrams of monitor image orientation vs. video camera orientation.

DETAILED DESCRIPTION

Figure 1:
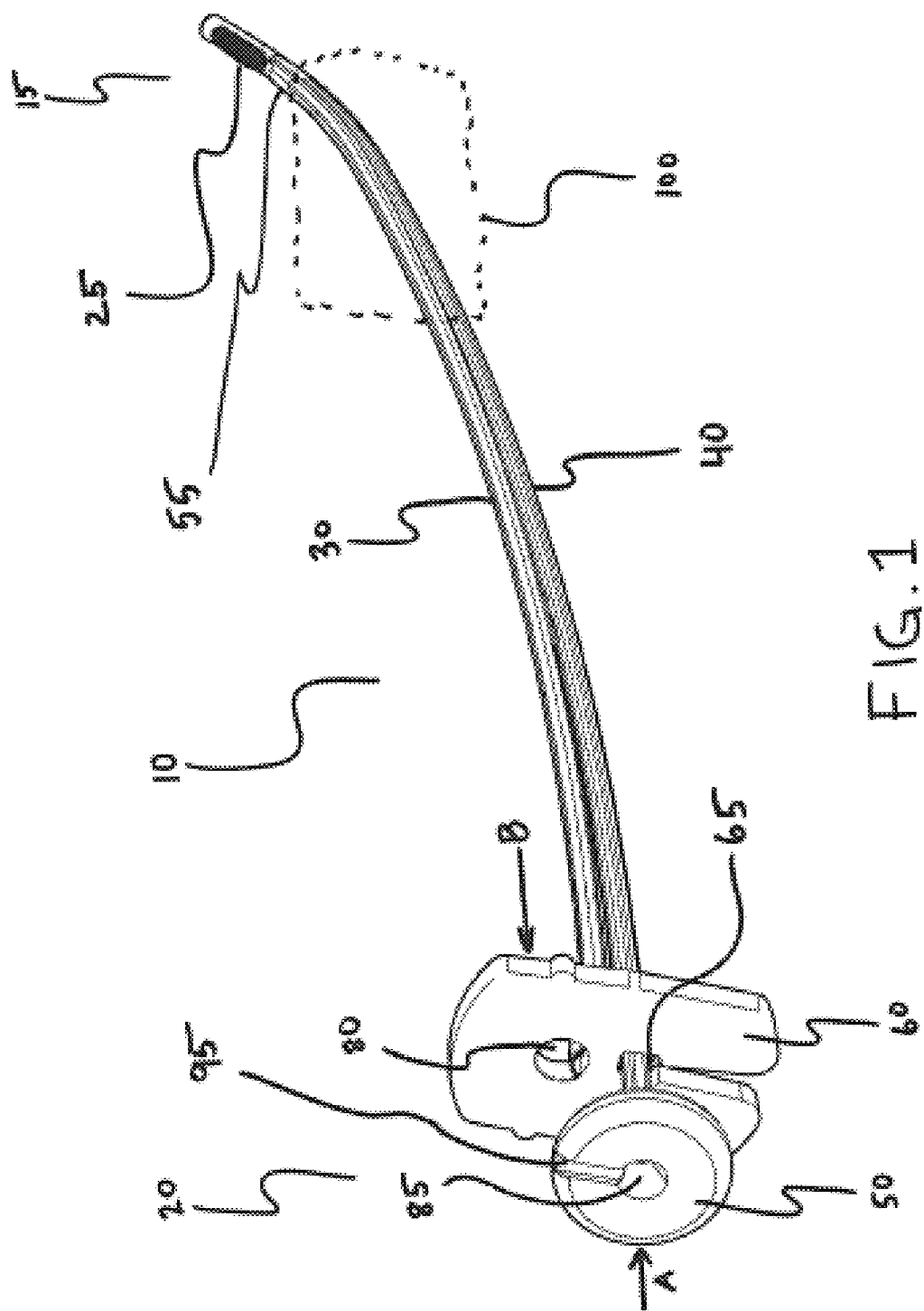
FIG. 1 is a perspective view of one embodiment of a stylet of the disclosure.

The invention relates to an imaging system having improved functionality for imaging of an enclosed space, such as a patient's respiratory tract. As such, the invention provides a device and system which combines a stylet with imaging and display capabilities to enable visualization of confined spaces. The system provides a low cost alternative that exhibits improved functionality as compared to existing imaging systems and is useful in a variety of fields including, but not limited to, medical treatment and diagnosis, surveillance, and mechanical and automotive applications.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

With reference to FIGS. 1-10, the present disclosure generally relates to a system and device for imaging a confined space, such as an airway of a subject. With specific reference to FIGS. 1-3, in general terms, in one embodiment the imaging system includes: a) a stylet (10) having a distal end (15), a proximal end (20) and a deflectable section (100) disposed there between; and b) an image acquisition element (25) disposed toward the distal end of the stylet. The stylet includes: i) a first shaft (40) and a second shaft (30). The proximal end of the first shaft is coupled to a first pressure receiving element (50) at the proximal end of the stylet. The distal end of second shaft is coupled to the distal end of the first shaft at the distal end of the stylet (at 55), while the proximal end of the second shaft is coupled to a second pressure receiving element (60) disposed distal to the first pressure receiving element at the proximal end of the stylet. In general, the second pressure receiving element engages the first shaft (i.e., at 65), such that application of opposing forces (arrows A and B) to the first and second pressure receiving elements (50, 60) produces a deflection in the deflectable section (100). As such, application of opposing forces allows angular deflection of the distal tip to be adjusted while entering a confined space, such as an airway.

Figure 2:
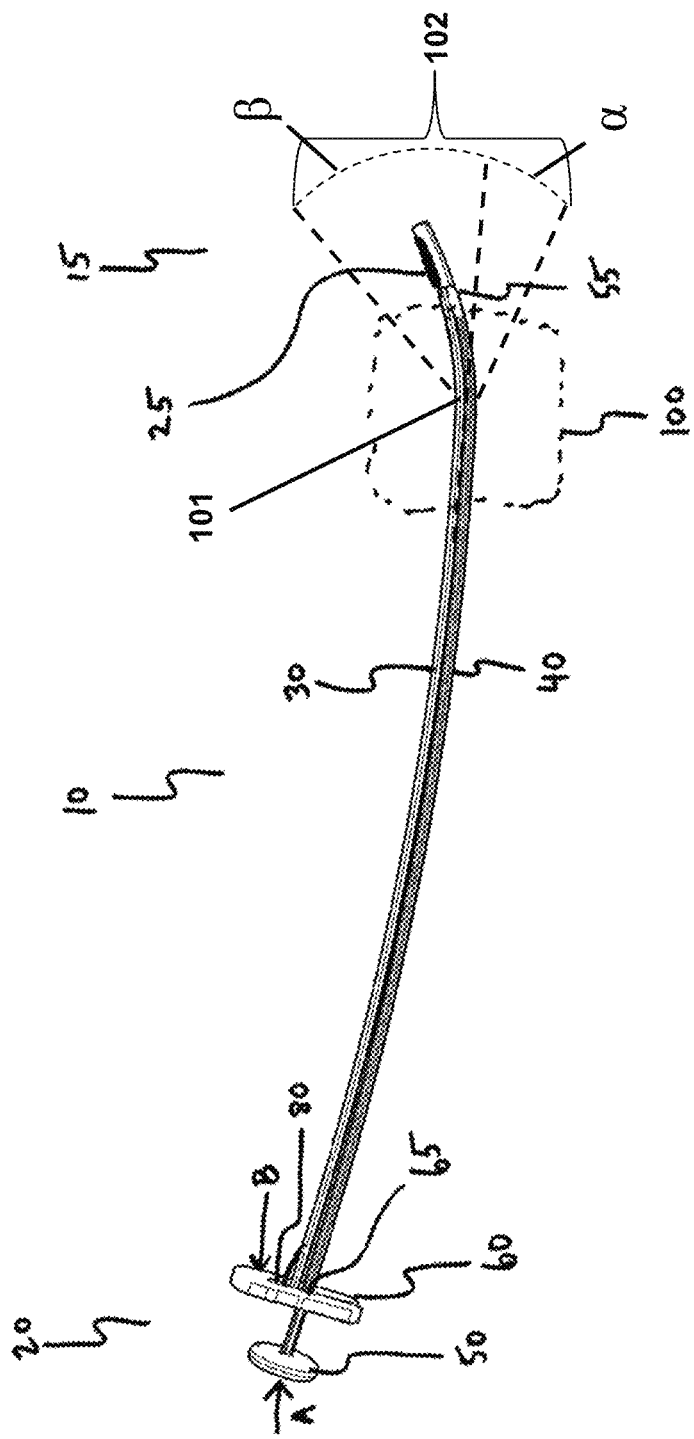
FIG. 2 is a side view of one embodiment of a stylet of the disclosure.

With reference to FIG. 2, within the deflectable section (100) is a deflection point (101) at which point an angle β is generated in the shafts (as opposed to a continuous bend) to pivot the tip thereby allowing steering of the tip though the airway. Upon deflection at the deflection point (101), the tip is pivoted with respect to the longitudinal axis of the stylet shaft through a deflection zone (102) which defines the range of motion and deflection angle. As used herein, the deflection zone refers to the area encompassed by the range of motion of the tip through angles α and β.

It will appreciated that while the stylet illustrated in FIGS. 1-10 includes only 2 flexible shafts, the stylet may have a multitude of flexible shafts, e.g., 2, 3, 4, 5, 6, 7, 8, 9, 10, 11, 12, 13, 14, 15, 16, 17, 18, 19, 20 or more.

Figure 30:
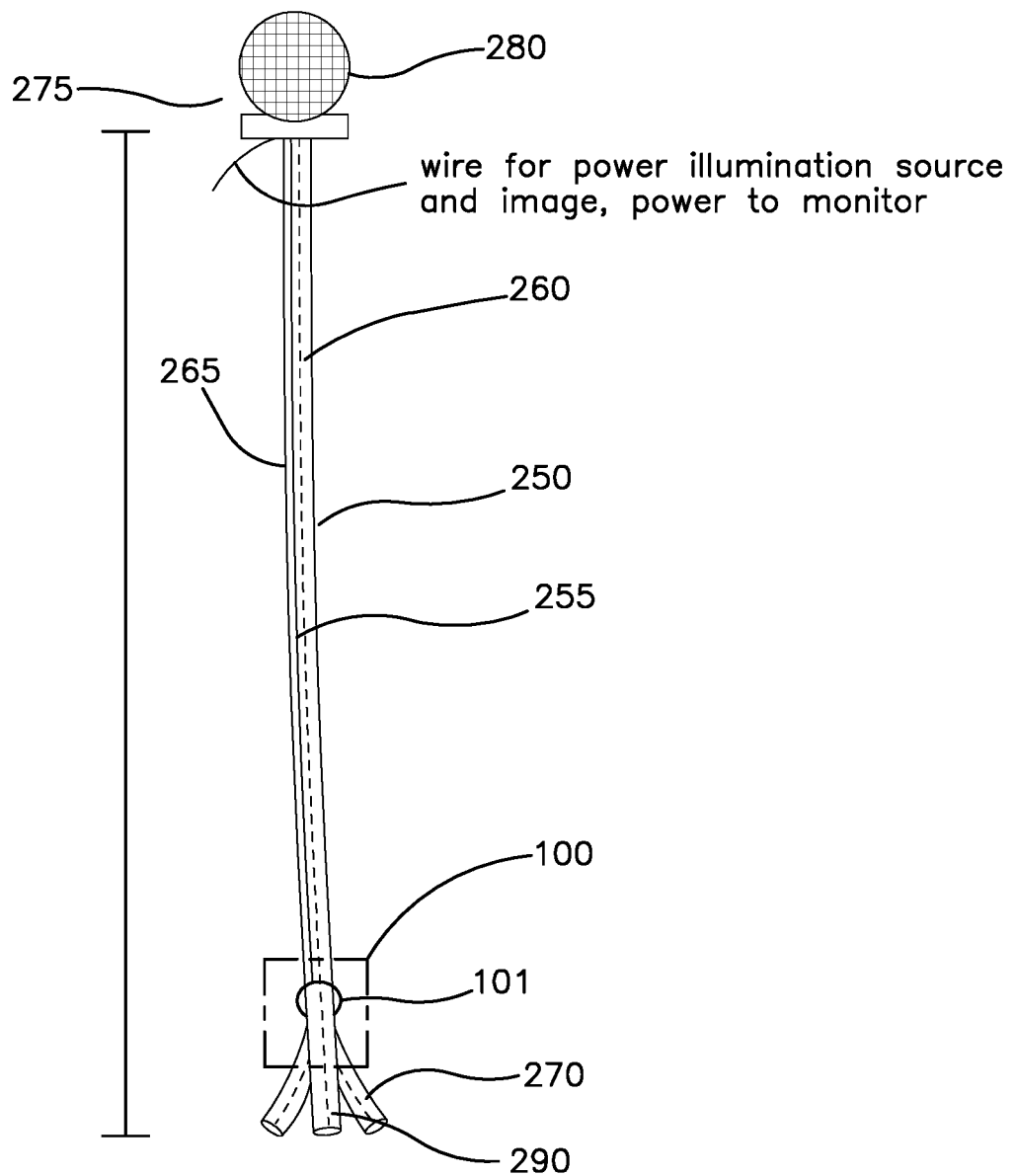
FIG. 30 is a front view of a stylet in one embodiment of the invention.
Figure 31:
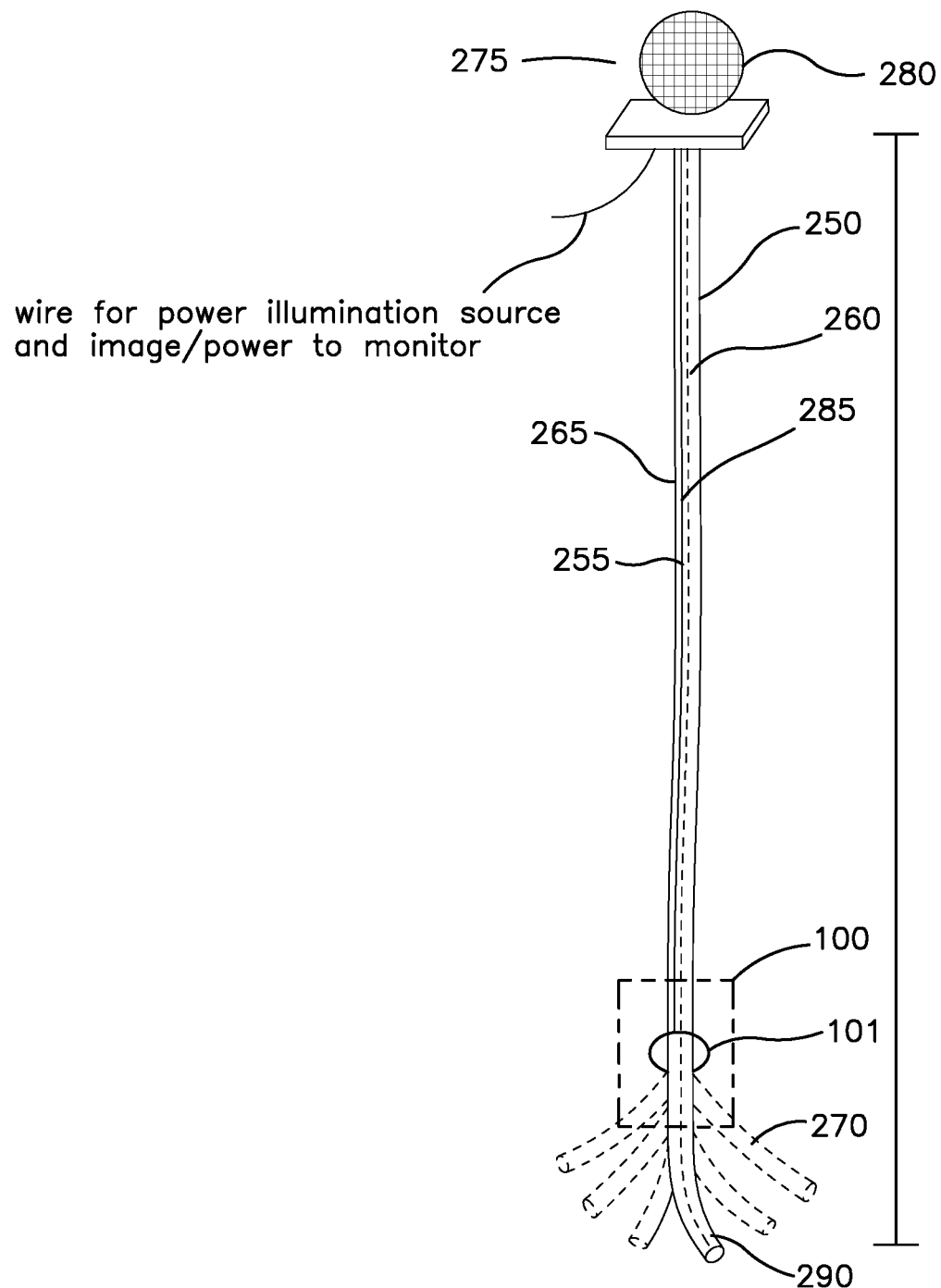
FIG. 31 is side view of the stylet of FIG. 30 in one embodiment of the invention.

Accordingly, as illustrated in FIGS. 30 and 31, the disclosure provides a steerable stylet that includes a stylet body (250); at least 3 flexible shafts (255) for controlling a pivotable tip (270) located proximate to a distal end of the stylet (D or E). The shafts (255) are disposed in a lumen (260) of the stylet body thereby forming an elongated unitary shaft (265). Additionally, the pivotable tip (270) is movable via a deflectable section (100) in at least three directions from the longitudinal axis of the distal end of the stylet (D or E). The stylet also includes an actuator control mechanism (275) having a ball-type control (280) for engaging a user's hand and controlling the pivot angle of the pivotable tip (270). The stylet further includes removable malleable rod (285) and an image acquisition element (290) disposed in the pivotable tip (270)

Within the deflectable section (100) is a deflection point (101) at which point an angle β is generated in the shafts (as opposed to a continuous bend) to pivot the tip thereby allowing steering of the tip though the airway. Upon deflection at the deflection point (101), the tip is pivoted with respect to the longitudinal axis of the stylet shaft through a deflection zone (102) as illustrated for the embodiment in FIG. 2.

It will be appreciated that the stylet of the invention may include multiple deflectable sections each with a deflection point. As such, the multiple angles of deflection may be imparted along the stylet body at each deflection point. This may be achieved by incorporating multiple shafts of varying lengths in the stylet body. Alternatively, as discussed below, this may also be achieved by incorporating multiple control wires of which are connected a different points along the stylet body.

As used herein, the term "image acquisition element" is used to refer to a means to acquire an optical image and convert said optical image into an electronic signal. An image acquisition element may be used to digitize individual still images or for digitization of multiple images in the form of motion picture images. Examples of digital image sensors include the charge coupled device (CCD) or the complementary metal-oxide-semiconductor (CMOS) active pixel sensor imagers. An active pixel sensor imager refers to a two-dimensional array of individual active pixel sensors, each active pixel sensor containing a photo-detector and an active amplifier. Such image acquisition elements are well known in the art as well as others which may be utilized. In one embodiment, the image sensor is a CMOS active pixel sensor imager. CMOS active pixel sensor arrays possess desirable characteristics such as ease of manufacture, low power consumption, and are less prone to the blooming effect where the light source overloads the sensitivity of each individual sensor causing bleeding of the light source into surrounding pixels enabling the use of a brighter light source to assist in visualization. The term image acquisition element may also refer to a component of an infrared thermal scanning system comprising an infrared imaging sensor. Commercially available CCD image sensors are sensitive to near-infrared light which facilitates infrared image capture sufficient for video transmission in zero lux (or near zero lux).

As will be understood by those in the art, the system of the present disclosure may include one or more image acquisition elements, for example 1, 2, 3, 4, 5, 6, 7, 8, 9, 10 or more. Additionally, while at least one image acquisition element is generally disposed toward or at the distal tip of the stylet, an image acquisition element may be located at any point along the length of the stylet to assist in imaging the interior of a cavity. Additionally, an image acquisition element may be angled in any direction with respect to the longitudinal axis of the device and be fully incorporated into the design of the stylet without protruding from the stylet's external surface. In one embodiment, at least one image acquisition element is arranged such that images distal to the distal tip are obtained while any additional image acquisition elements are arranged such that images radial to the longitudinal axis of the stylet may be obtained.

Figure 4:
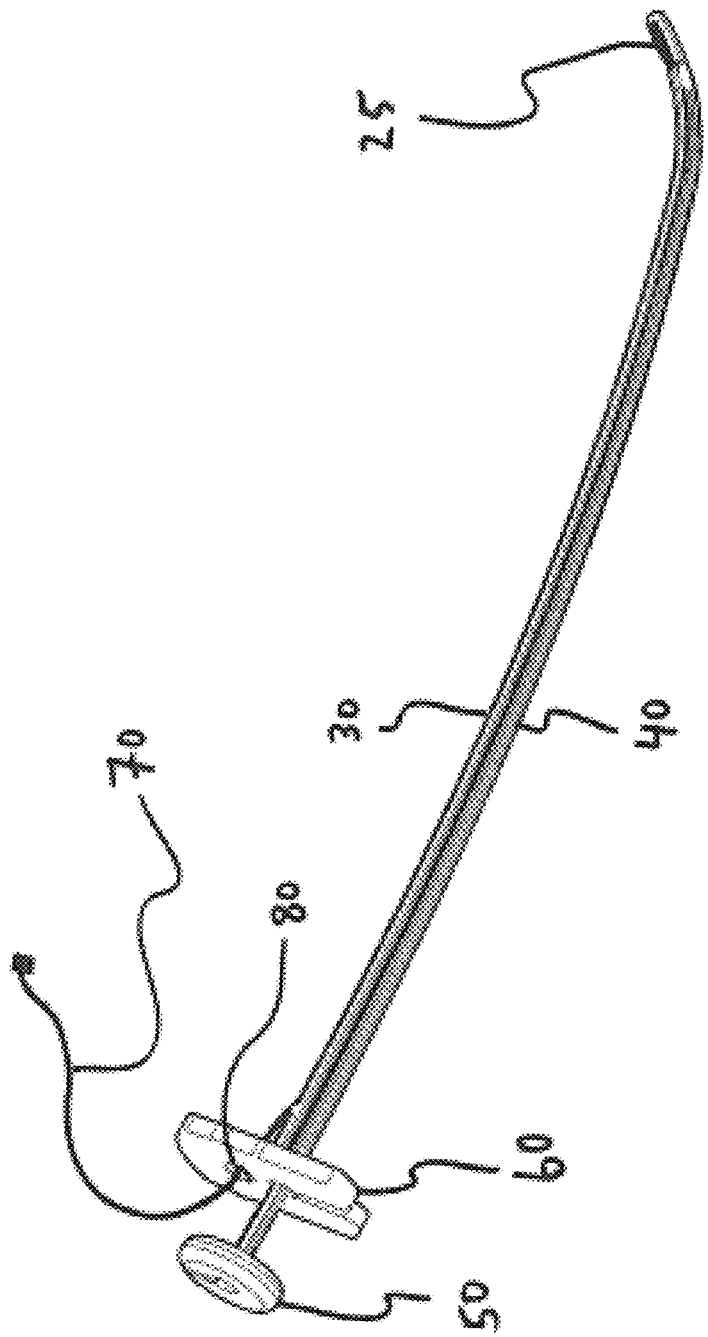
FIG. 4 is a perspective view of one embodiment of a stylet of the disclosure.
Figure 5:
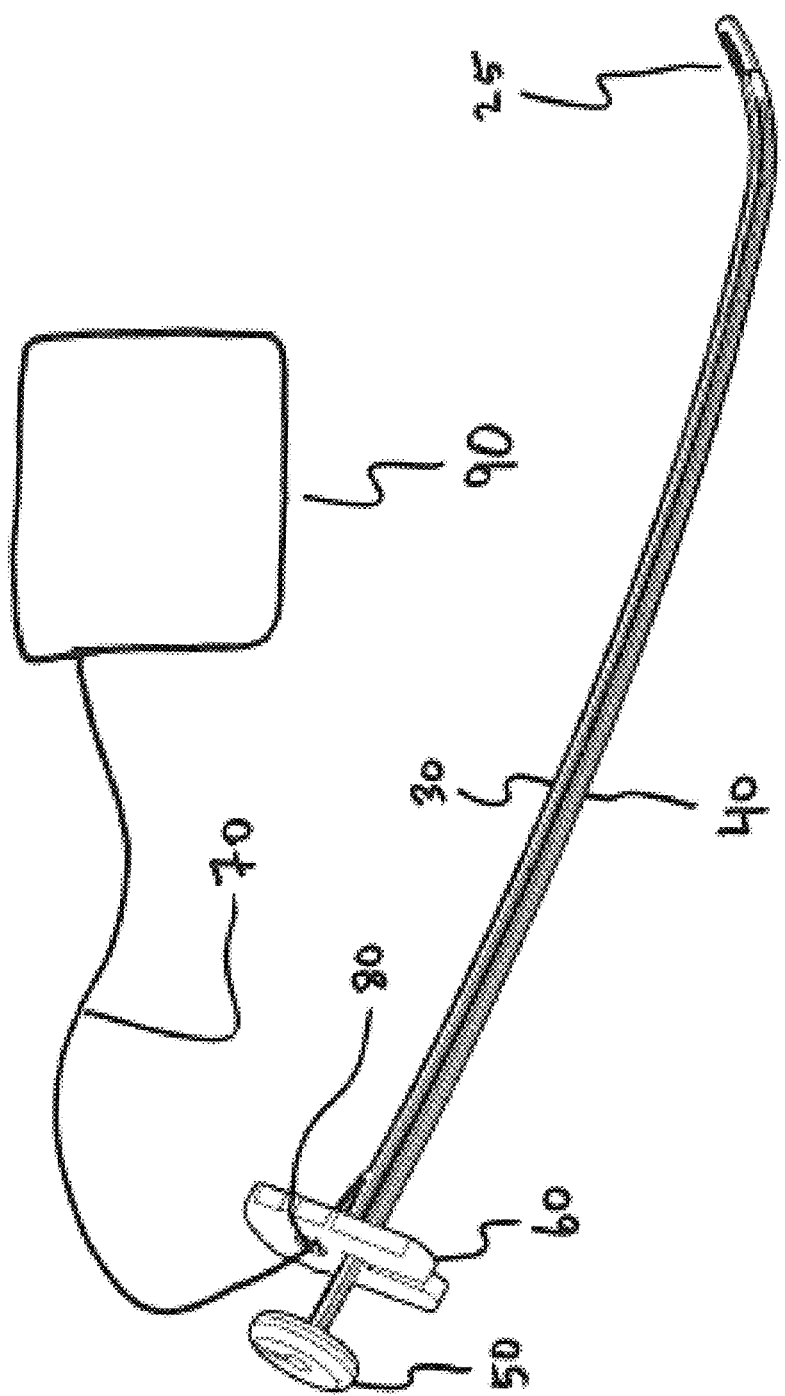
FIG. 5 is a perspective view of one embodiment of an imaging system of the disclosure.

With reference to FIGS. 4 and 5, the system may further include an image conduit (70) for transmission of electrical signals from the image acquisition element, to, for example, a display (90). As illustrated in FIGS. 4 and 5, image conduit (70) traverses the length of the second shaft (30) and through the second pressure receiving element (60) via hole (80) which traverses the thickness of the second pressure receiving element (60). Image conduit (70) allows electrical communication between the image acquisition element and, display (90) for example. As will be understood by those on the art, image conduit (70) may be coupled with multiple image acquisition elements for transmission of electrical signals. Further, while the embodiment shown FIGS. 4 and 5 depicts image conduit (70) as traversing the length of the second shaft (30), it will be understood that image conduit (70) may alternatively traverse the length of the first shaft (40). In various embodiments, the image conduit traverses the first or second shaft via a lumen or groove disposed within or on the surface of the respective shaft.

In addition to multiple image acquisition elements, the system of the disclosure may further include one or more illumination sources for illuminating the inside of a cavity to assist in image acquisition. For example, illuminating light may be provided to the interior of a cavity via an illumination source disposed along the stylet. In one embodiment, at least one illumination source is arranged on the stylet such that light is emitted distal to the distal tip of the stylet. The illumination source may be arranged in any manner that facilities illuminating the cavity. For instance, the illumination source may be arranged an array having a plurality of sources. One or more optical channels may be provided in the stylet to house the illumination source which may be equipped with its own power source or be in electrical communication with the display which may be equipped with functionality to operate the illumination source. In one embodiment, electrical communication for the illumination source may be achieved by integrating the wiring into the optical conduit. Alternatively, the illumination source may receive illuminating light from an external source or the display via an optical channel suitable to transmit light. The illumination source may emit any source of illumination including infrared, ultraviolet, visible light of one or more frequencies or white or colored light. Additionally, the illumination source may convey electromagnetic radiation of a specific nature (e.g., light of specific color or hue, laser light, infrared or ultraviolet light, and the like.). In one embodiment, the illumination source is employed to deliver electromagnetic radiation of a particular wavelength.

As an alternative to transmission of an acquired image through image conduit (70), an acquired image may also be wirelessly transferred to the display. As such, an image acquisition element of the disclosure may include functionality for wirelesly transmitting a signal, such as via a data communication link. Additionally, wireless communication pathways may be configured for secure, encrypted uni- or bi-directional data exchange. In particular, wireless functionality may include radio data communication, satellite data communication, Wi-Fi data communication, IrDA data communication, infrared data communication, Bluetooth™ data communication, and ZigBee™ data communication. Additional wireless communication protocols include, Wi-Fi™ 802.11 a/b/g/n, Bluetooth®, or cellular data transfer protocols such as GSM, 3G. 4G, LTE and similar protocols for the wireless transfer of data.

As used herein, the term "display" refers to a device for providing a two-dimensional or three-dimensional representation of the image acquired by the image acquisition element. Commercially available versions of such displays include but are not liquid crystal displays as well as light emitting diodes (LED), polymer light emitting diodes (PLED), organic light emitting diodes (OLED), polymer organic light emitting diodes (PLOED), passive matrix organic light emitting diode (PMOLED), or active matrix organic light emitting diode (AMOLED) arrays. The use of OLED technology facilitates flexible displays and may be preferred where such flexible display technology is desirable. Multiple layers of transparent OLED layers may also be incorporated to provide three dimensional image display which may be useful in some applications where the apparatus of the present invention is used to visualize the use of remote manipulating tools where depth perception or three dimensional details are of interest to the operator. Such displays may also incorporate touch screen technology to facilitate manipulation (e.g. zoom, rotation, or perspective) of the image displayed on the display means.

In certain circumstances, it may be useful to have a power supply capable of supplementing the power supply of the system to facilitate extended use of the system and/or illumination source if so provided. It will be understood that the power source for the display of the disclosure may be external voltage from, for example, a wall outlet, or may be provided via batteries. Additionally, the amount of power supplied will be sufficient to also power all other components of the system, for example the image acquisition element as well as illumination sources if utilized. As used herein, batteries may be non-rechargeable or rechargeable. Examples of batteries useful in the practice of the present invention include zinc-carbon, zinc-chloride, alkaline (e.g., zinc-manganese dioxide), lithium (e.g., lithium-copper oxide, lithium-iron disulfide, lithium manganese dioxide), silver oxide, silver-zinc, NiCd, NiMH, NiZn, lithium ion batteries. The term battery includes a single cell or a plurality of two or more cells. For purposes of shipment and extended shelf life, there should be an operator removable physical barrier introduced between the power source and the circuitry of the remainder of the transmission module to preserve the power source during storage and shipment and guard against parasitic drain of power supply. When rechargeable batteries are used as the power source, the device of the present invention may also be provided with a recharging system adapted for the particular configuration and specifications of the rechargeable battery employed.

In various embodiments, images generated by the image acquisition element may be transferred to the display, and alternatively to a one or more additional displays. This may be accomplished by direct wireless transmission from the image acquisition element to the additional display or by wireless transmission from the primary display to the additional display. As such, the system provides for remote monitoring. For example, a supervising physician may be able to receive images acquired by different systems being utilized in multiple different rooms.

As shown in FIGS. 1-5, the first and second shaft of the stylet are coupled at the distal end of the stylet, with the first and second shafts being independent at the proximal end of the stylet. It will be understood that the point at which the first and second shaft are uncoupled to one another along the length of the stylet determines the amount of deflection of the distal tip as well as the size and location of the deflection zone. As such, the first and second shaft may be uncoupled at any point along the length of the stylet, for example the shafts are uncoupled at about 0.25, 0.50, 0.75, 1.0, 1.25, 1.50, 1.75, 2.0, 2.25, 2.50, 2.75, 3.0, 3.25, 3.50, 3.75, 4.0, 4.25, 4.50, 4.75, 5.0, 5.25, 5.50, 5.75, 6.0, 6.25, 6.50, 6.75, or 7.0 inches from the distal tip of the stylet. Further, the stylet may be configured to split into or be comprised of more than two independent shafts upon transition of the stylet to the deflected state. For example, each shaft may form 2, 3, 4, or 5 more independent shafts each connected to one or more of the other shafts at various locations along the length of the stylet. The stylet may include a third flexible shaft coupled to a first flexible shaft and a second flexible shaft at the distal end of the stylet. Application of force to the third flexible shaft produces curved or angled deflection in the deflectable section to facilitate steering in a third direction. Such steering is needed for correct placement of a single or double lumen endotracheal tube in a mainstem bronchus. A simple tab or loop at the proximal end of the stylet can be used for delivery of force by the hand of the user to these extra flexible shafts. All or part of any of these extra flexible shafts may be composed of materials with different or the same elasticity as the other shafts. For example, the third shaft may be composed of a flexible wire or flexible plastic material while the first two shafts are composed of the same or different material.

Additionally, while the embodiment shown in FIGS. 1-5 depicts the first and second shafts as being adjacent one another (i.e., side-by-side), it will be understood that the first and second flexible shaft may be configured to be coextensive or conterminous in a variety of geometries. For example, the one shaft may be disposed within a lumen or recess of the other along a portion of, or the entire length of the shafts. Additionally, it will be understood that the shafts may be manufactured of the same or different materials. For example one shaft may be more rigid than the other. In an embodiment, one shaft is disposed within a lumen or recess of the other along a portion of, or the entire length of the shafts, and one shaft is composed of material having a different elasticity than the other. For example, all or part of one shaft may be composed of a malleable metal or composed of a flexible wire while the other is entirely or partially composed of a plastic material. Many combinations are suitable for this invention as well as synthetic wire materials.

Any number of materials may be utilized in various components of the invention. Examples of suitable materials are well known in the art including thermoform or thermoset plastics but are not limited to polycarbonate (PC), polyethylene (PE), high density polyethylene (HDPE), polyetherimide (PEI), polysulfone (PSO), polyethersulfone (PES), polyethylene terepthalate (PET), polypropylene, polystyrene, high impact polystyrene (HIPS), acrylanitrile butadiene styrene (ABS), polyvinylchloride (PVC), acetal, Nylons (e.g., Nylon 4-6, Nylone 6-6, Nylon 11, or Nylon 12) , acrylic-styreneacetonitrile (ASA), polyester liquid crystal polymer (LCP), stylene acrylonitrile (SAN), polyvinyldiene difluoride (PVDF), melamine, phenolics and the like. Typical procedures for forming the materials into suitable housing may be formed by compression molding, blow molding, casting, extrusion, pressure forming, and the like.

In one embodiment of the invention, one or more of the components of the present invention is/are fabricated from or coated with materials that provide improved non-slip surfaces, particularly when wet such as rubber, Neoprene or other suitable thermoplastic elastomers.

The present invention also provides software application capable of execution on elements of the system which are provided with microprocessors. For example, an application which upon initiation places the system in condition for display of the image conducted to the display from the image acquisition element. For example such software would place the system in video mode, and optionally turn on the illumination source, and enable controls such as illumination level, zoom control, and focus control of the image acquisition element, recording, and broadcast of the signal to remote devices such as other networked computers and portable computing and communication devices such as smartphones.

The various steps in these functional processes or blocks that may be implemented in a variety of ways. It should also be noted that the various functions disclosed herein may be described using any number of combinations of hardware, firmware, and/or as data and/or instructions embodied in various machine-readable or computer-readable media, in terms of their behavioral, register transfer, logic component, and/or other characteristics. For example, the functions of various blocks can be combined with one another into any other number of modules.

Each module can be implemented as a software program stored on computer readable media provided in a component of the system. Computer-readable media in which such formatted data and/or instructions may be embodied include, but are not limited to, a tangible memory (e.g., random access memory, read only memory, etc.) to be read by a central processing unit to implement the functions.

The application software may be accessed from within or loaded into a component of the system. As disclosed herein, embodiments and features of the invention may be implemented through computer-hardware, software and/or firmware. Although some of the disclosed implementations describe components such as software, systems and methods consistent with the innovations herein may be implemented with any combination of hardware, software and/or firmware.

Figure 3:
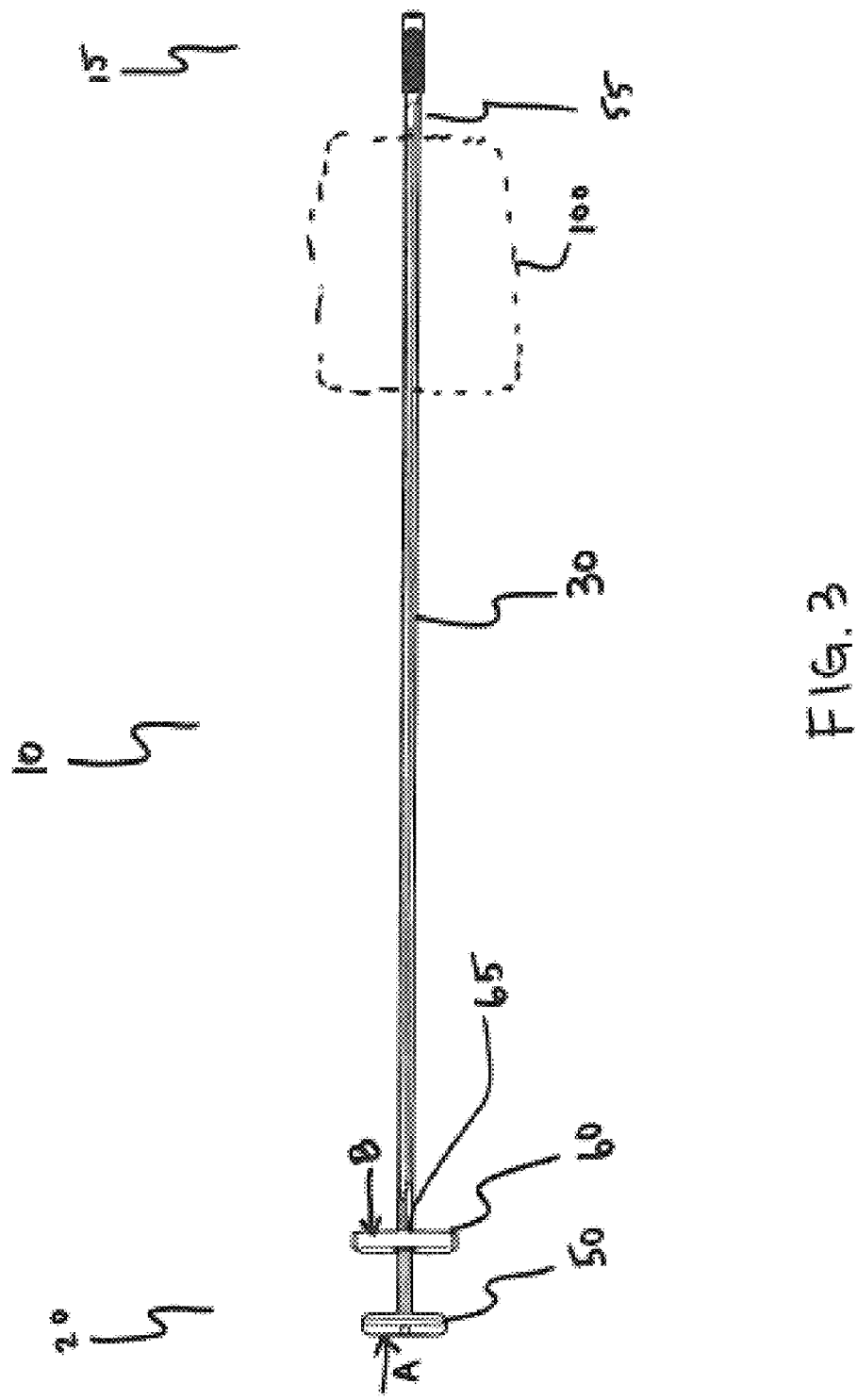
FIG. 3 is a top view of one embodiment of a stylet of the disclosure.

The system of the present disclosure may further include a malleable rod. The rod may be received within a lumen or groove which traverses all or a portion of the length of the stylet. Again with reference to FIGS. 1-3, in one embodiment, first shaft (40) includes a central lumen or recess traversing all or a portion of its length, and accessed by opening (85) in the first pressure receiving element (50). While the embodiment of FIGS. 1-3 depicts the first shaft being configured to receive the malleable rod, it will be understood that the second shaft may alternatively, or also, be configured to receive the malleable rod. The malleable rod is inserted into the shaft such that the shaft may be bent to have a predetermined shape or deflection. In various embodiments, the first or second pressure receiving element is provided with a recess configured to house the end of the malleable rod so that the end of the rod does not interfere with the user. For example, the embodiment shown in FIG. 1 includes recess (95) in the first pressure receiving element (50).

The display allows the user to view the inside of a cavity while manipulating the distal end of the stylet within the cavity. This is extremely advantageous when conducting medical procedures such as endotracheal intubation of a subject which requires exact placement and advancement of the distal tip of the stylet into the trachea. Ideally, the display is positioned such that the user may easily view the display while also manipulating and operating the stylet. In one embodiment, the display is adapted to be worn on the wrist of a user so that the user has a direct view of the display at all times during an intubation procedure. For example, the display may be attached to a sleeve to be worn by the user. Alternatively, the system may also include a display holder to house the display having a malleable or articulating arm adapted to attach or couple to an object in the user's surrounding, such as an IV pole, side rail or operating room table.

As discussed herein, the stylet of the disclosure transitions from a first relaxed configuration to a second deflected state upon application of opposing forces to the first and second pressure receiving elements. As shown in FIGS. 1-3, application of opposing forces (arrows A and B) to the first and second pressure receiving elements (50, 60) produces a deflection in the deflectable section (100). As such, application of opposing forces allows deflection of the tip to be adjusted while entering a confined space, such as an airway. Typically, the stylet is transitioned from the first configuration to the second configuration by forces applied by a thumb and one or more fingers of a user such that the first and second pressure receiving elements are squeezed together. However, it will be appreciated by those in the art that such a force may be generated in a variety of ways. For example, in one embodiment, the first and second pressure receiving elements of the stylet may by electromechanically coupled and configured to draw the first and second pressure receiving elements closer to one another. The stylet may further include an actuator to facilitate generation of force.

In various embodiments, the electromechanical coupling may be voice activated or activated by a mechanical or digital switch.

Additionally, the system of the disclosure may be configured such that the stylet may be maintained in a particular configuration, for example, the first relaxed configuration or the second deflected configuration. One in the art would appreciate that this may be accomplished in a variety of ways. In one embodiment, the stylet may be configured such that the first and second pressure receiving elements interlock with one another during transitioning of the stylet between configurations. This may be achieved via the electromagnetic coupling or alternatively, the first and second pressure receiving elements may include releasably interlocking elements that prevent transition of the stylet back to the relaxed configuration while the stylet is being deflected.

Figure 6:
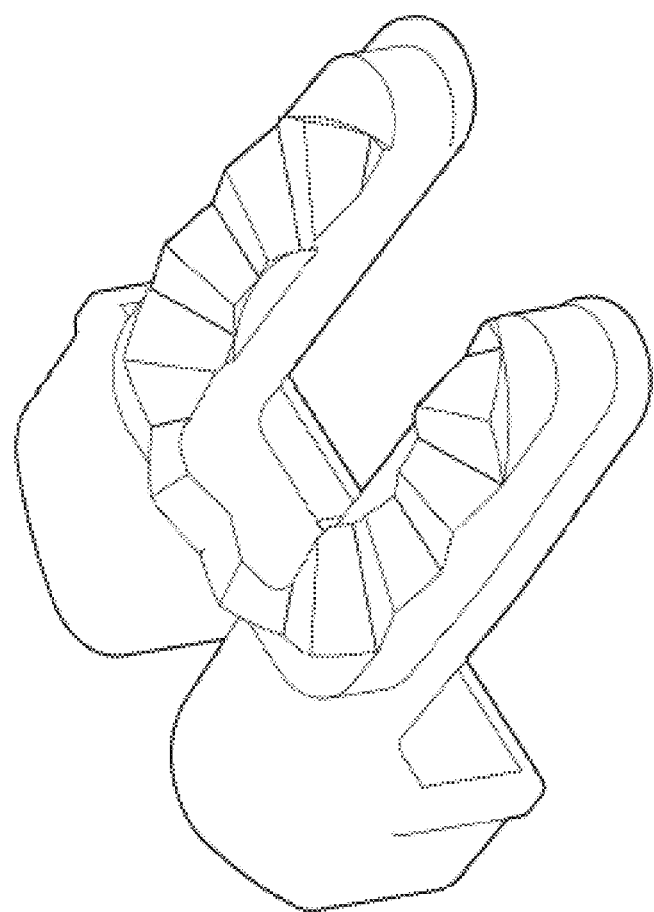
FIG. 6 is a perspective view of one embodiment of a spacer of the disclosure.
Figure 7:
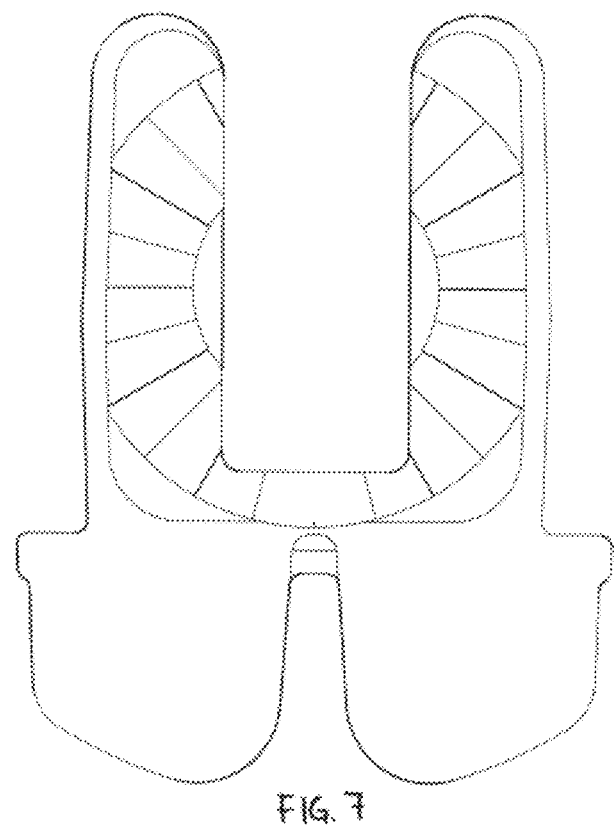
FIG. 7 is a front view of one embodiment of a spacer of the disclosure.
Figure 8:
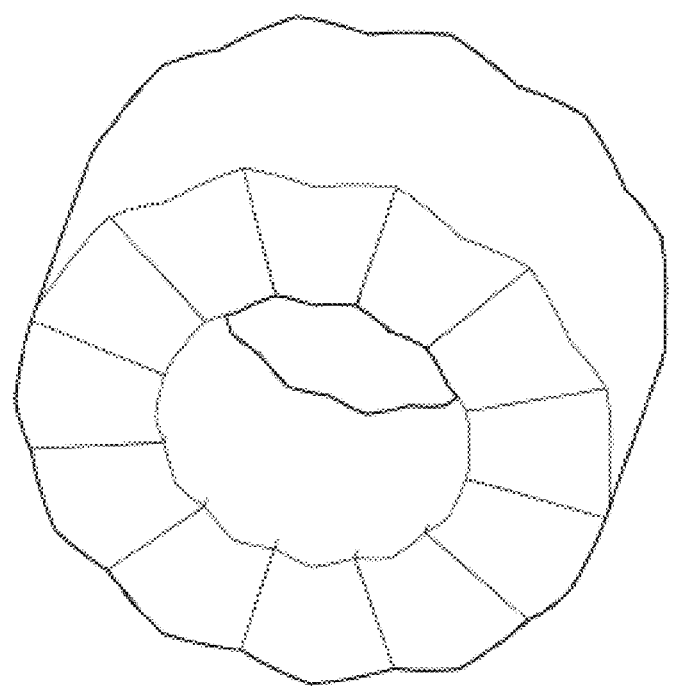
FIG. 8 is a perspective view of one embodiment of a spacer of the disclosure.
Figure 9:
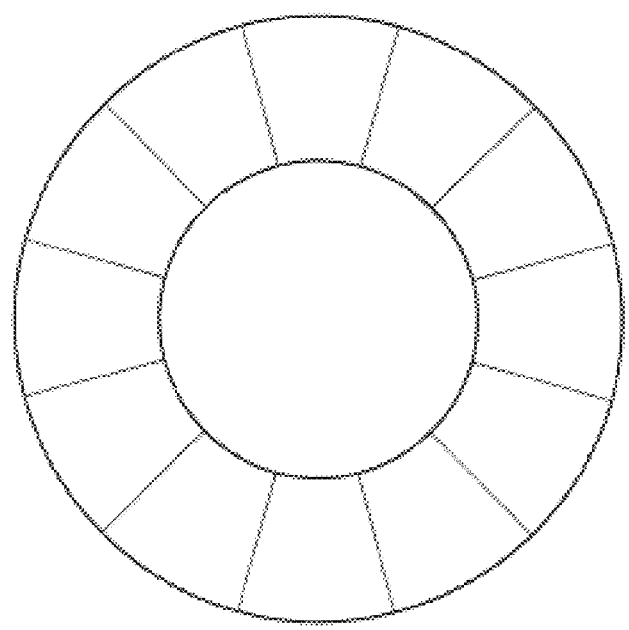
FIG. 9 is a front view of one embodiment of a spacer of the disclosure.
Figure 10:
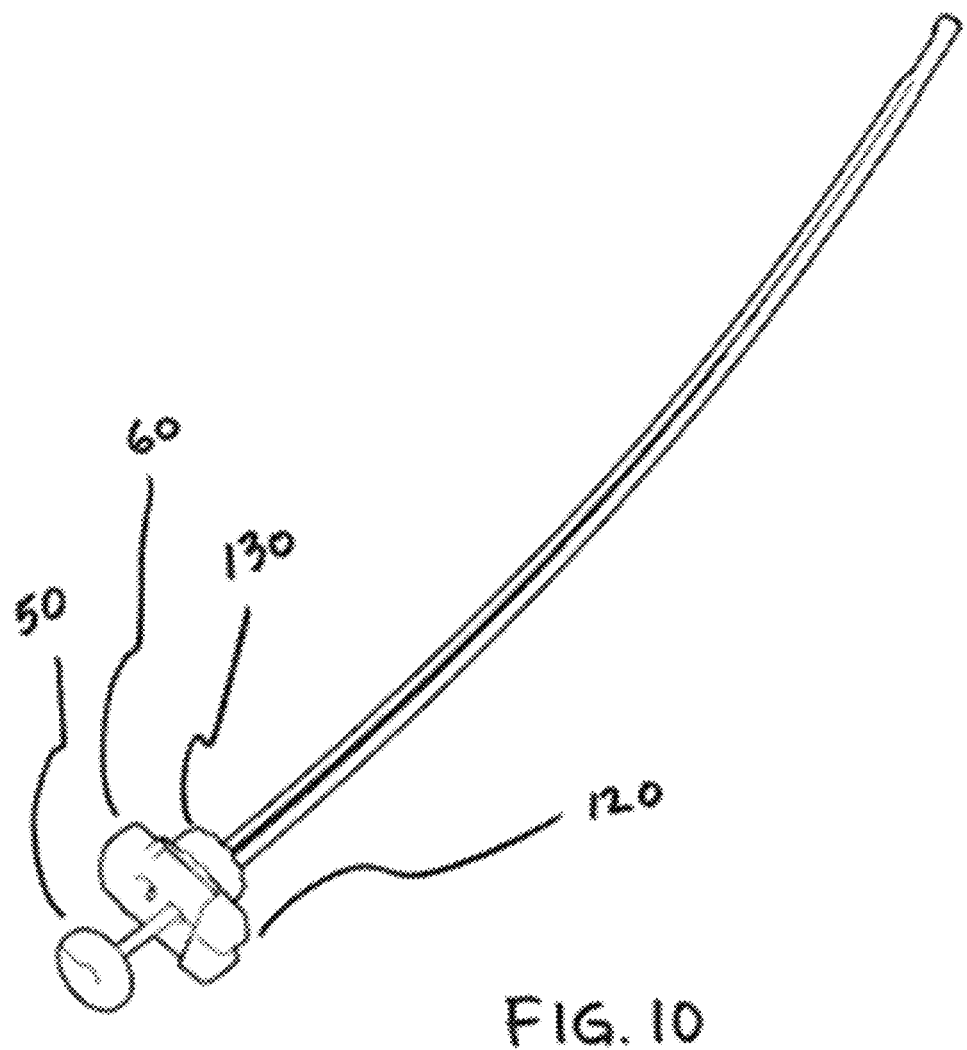
FIG. 10 is a perspective view of one embodiment of a stylet of the disclosure with spacers.
Figure 11:
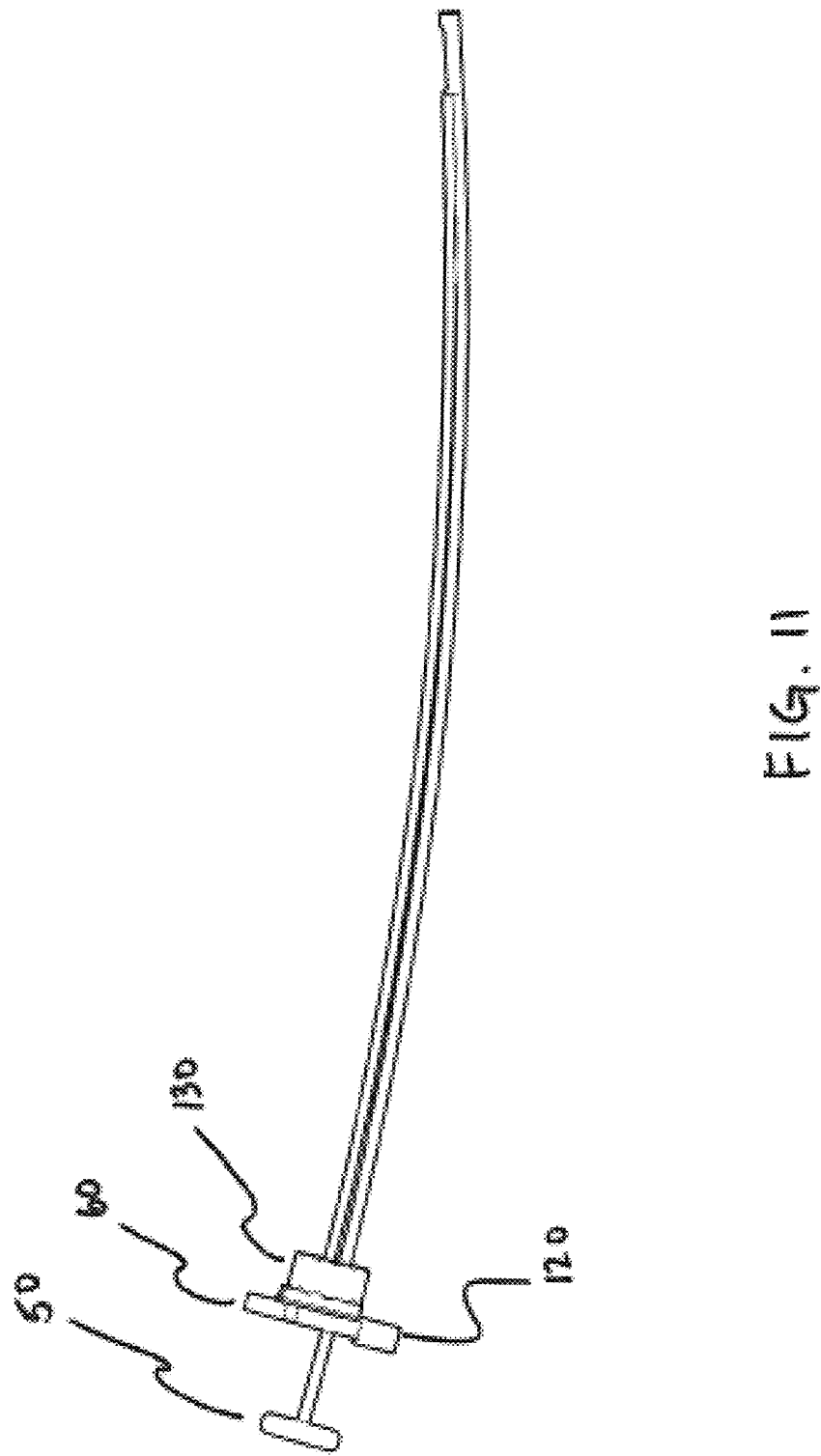
FIG. 11 is a side view of one embodiment of a spacer of the disclosure with spacers.

Advantageously, the stylet of the system of the disclosure, is adaptable to be used with accessory devices of different lengths and types. For example, the length of the stylet may be altered by inclusion of stylet spacers or an attaching portion that may be disposed over that first and second shafts of the stylet. FIGS. 6-9 illustrate spacers that may be utilized with the present system embodiments of the invention. FIGS. 6 and 7 depict an embodiment of a spacer that is disposed over the stylet shaft and configured to couple to a pressure receiving element. FIGS. 8 and 9 illustrate an embodiment of a spacer that is disposed over the stylet shaft and configured to engage the spacer shown in FIGS. 6 and 7. As shown in FIGS. 10 and 11, spacer (120; that shown in FIGS. 6 and 7) couples with the second pressure receiving element (60) and engages a second spacer (130; that shown in FIGS. 9 and 10). The spacers may be configured or shaped such that rotational motion between the spacers is prevented. This may be accomplished in a number of ways. For example, the spacers may include surface grooves or ridges that prevent rotation with an adjacent spacer. In various embodiments, a stylet may be configured to include any number of spacers, such as 1, 2, 3, 4, 5, 6, 7, 8 or more spacers. The stylet spacer or attaching portion may optionally be configured to engage with the actuator control mechanism designed as a wheel with pressure receiving elements about its circumference.

The ability to adjust the length of the stylet allows the system to be used with a variety of accessory devices of different lengths and types. For example, the system of the disclosure is adaptable for use with accessory devices for both pediatric and adult application, such as pediatric and adult ETs.

The system of the disclosure is ideal for use with a video laryngoscope, video supraglottic airway, video ET or a video oral airway. In addition to its use as a device capable of delivering immediate visual verification of correct ET placement (faster and more accurate than either the capnography or breath sounds), this system has the added benefit of being a standalone low-cost alternative to video laryngoscopes for use with difficult intubations. It can also augment the use of a video laryngoscope by providing a view of the larynx from the tip of the ET during intubation thus providing an immediate image of a correctly placed (trachea) or incorrectly placed (esophagus) ET. The view of the larynx is often obstructed during video laryngoscope intubation as the distal end of the ET passes in front of the video laryngoscope's camera. Additionally, the correct ET depth placement within the trachea can be quickly visually verified thus preventing an inadvertent endobronchial intubation; a benefit not provided by a video laryngoscope used without this invention.

In one aspect, the system of the disclosure is used for intubating a subject. As such the invention provides a method for intubating a subject. Generally, the method includes inserting the stylet of the disclosure into an ET. The stylet and the ET are then inserted into the airway of the subject. The airway of the subject is visualized via images acquired by the image acquisition element and transmitted to the display. The stylet and the ET are then inserted into the trachea of the subject and subsequently the stylet is removed from the subject's trachea. In embodiments, the method may further include confirming correct depth of placement of the ET in the trachea of the subject. Additionally, a malleable rod may be inserted into the first or second shaft of the stylet and bent to a desired curvature before inserting the stylet into the airway.

The ability to controllably place a display near the patient's oral opening allows the laryngoscopist to intubate the patient without having to move his head and neck to view a distant screen. A display placed near or adjacent to the proximal end of a stylet or ET is similarly out of the laryngoscopist's field of view during direct laryngoscopy. Any small movement of the head and neck away from the view during direct laryngoscopy complicates visualization of the vocal cords and can lead to injury of the teeth, gums, or lips.

This allows the laryngoscopist to view the larynx with direct vision by using standard laryngoscope blades such as the Miller blade and MAC blade without changing technique. Because of their low profile and non-accentuated curvature when compared to video laryngoscopic blades, they are typically preferred by experienced laryngoscopists. Thus, the laryngoscopist needs only to move his eyes to rapidly switch between direct and video views of the larynx. Direct laryngoscopy is thus augmented with a system that does not require a significant 'learning curve' to use successfully.

As used herein, the term "patient" or "subject" refers to a variety of animal types. Generally the patient or subject is human, although as will be appreciated by those in the art, the patient or subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition. As such, it is clear that the system of the invention may be utilized in veterinary applications.

Figures 19A, 19B:
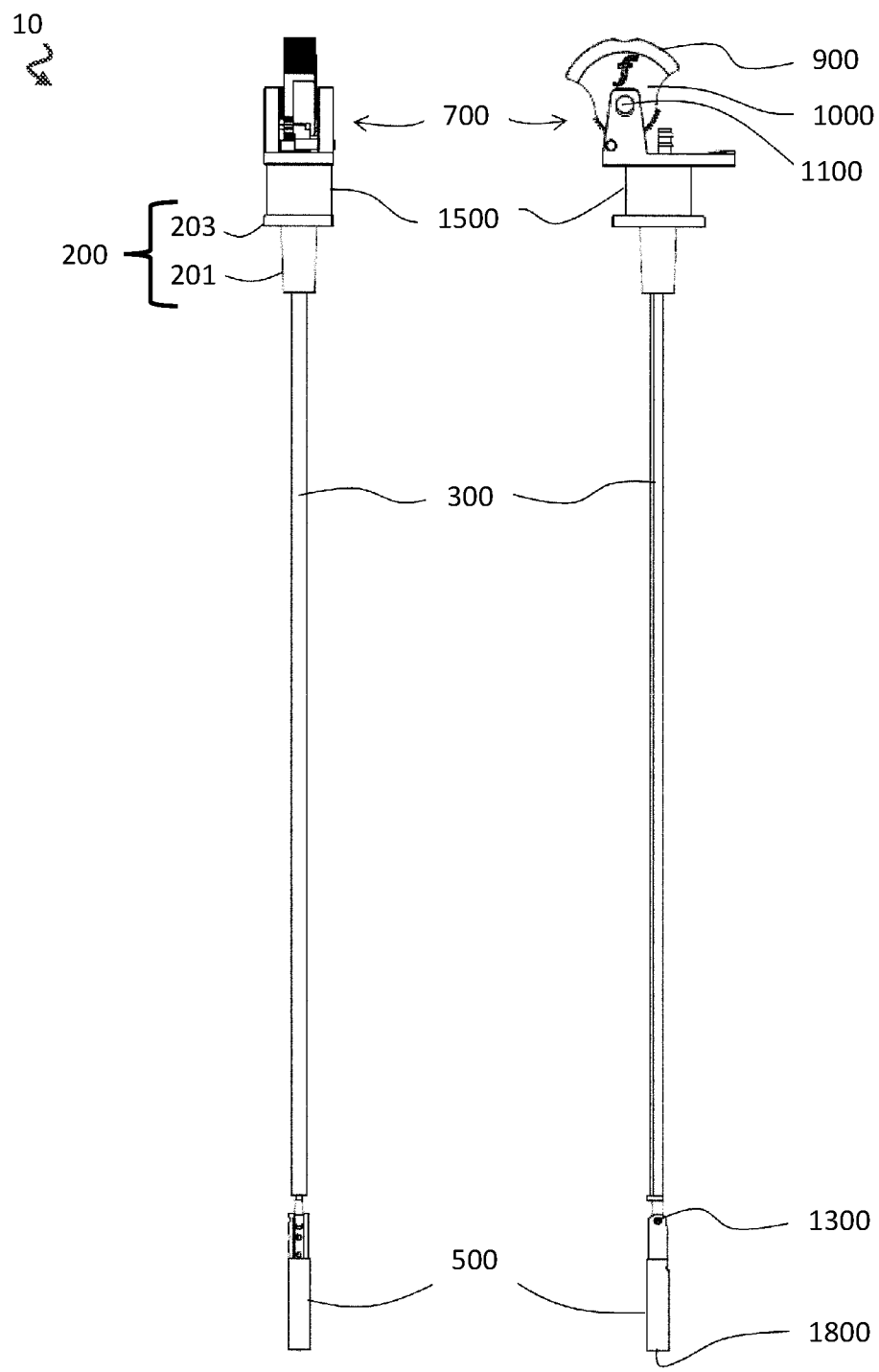
FIGS. 19A-19B, 19(A) shows a front aspect, and 19(B) a side aspect of a stylet.

FIG. 19 shows (a) a front aspect, and (b) a side aspect of a stylet (10) of the disclosure, connected to an ET connector (200). The stylet has a stylet body (300) with a distal and a proximal end. Distal and proximal are here described in relation to the use of the stylet, with the proximal end being the end of the stylet which is typically held by an operator during use in a process of intubation. The distal end of the stylet is the end which in use may be inserted into a patient's airway to assist in an intubation process. The stylet has a pivotable tip (500) located at the distal end of the stylet body, and an actuator (700) attached at the proximal end of the stylet body. The actuator (shown in FIG. 21 and described in detail below) is here conveniently manipulated by the operator using a thumb-pad (900) on a dial (1000) which rotates around an axle (1100). The pivotable tip is affixed to the stylet body (300) at a pivot hinge (1300) which allows movement of the pivotable tip in a plane. The stylet has an attaching portion (1500) located at the proximal end of the stylet, formed integrally with the body/retaining housing (1700) of the actuator. The attaching portion here is formed as a receiving socket or plug portion which forms a plug-fit connection with an ET connector (200), which has a tapered portion (201) for connecting to an ET, and a flange portion (203). The ET connector (200) is one of standard known ET connectors and does not in itself form part of the proposals relating to the stylet.

FIGS. 12-14 and 17-18 illustrate a stylet of the invention which is substantially the same as that of FIG. 19. However, the actuator is manipulated by the operator using a thumb-pad (900) on a dial (1000) having multiple arcuate recesses (3100) disposed about the dial (1000). Further, the thumb-pad may be composed of different material than the dial to facilitate tactile friction with a digit of the operator.

In various embodiments, the handle portion of the malleable rod includes a tab (3000) that has a tip that extends beyond the housing when the rod is disposed within the stylet body to facilitate contact with a digit of the user. In embodiments, the tab may be configured as a disk having a circular, elliptical, square, triangular, or rectangular shape. FIGS. 12-18 illustrate a malleable rod in which the tab (3000) is generally elliptical.

Figures 20A, 20B:
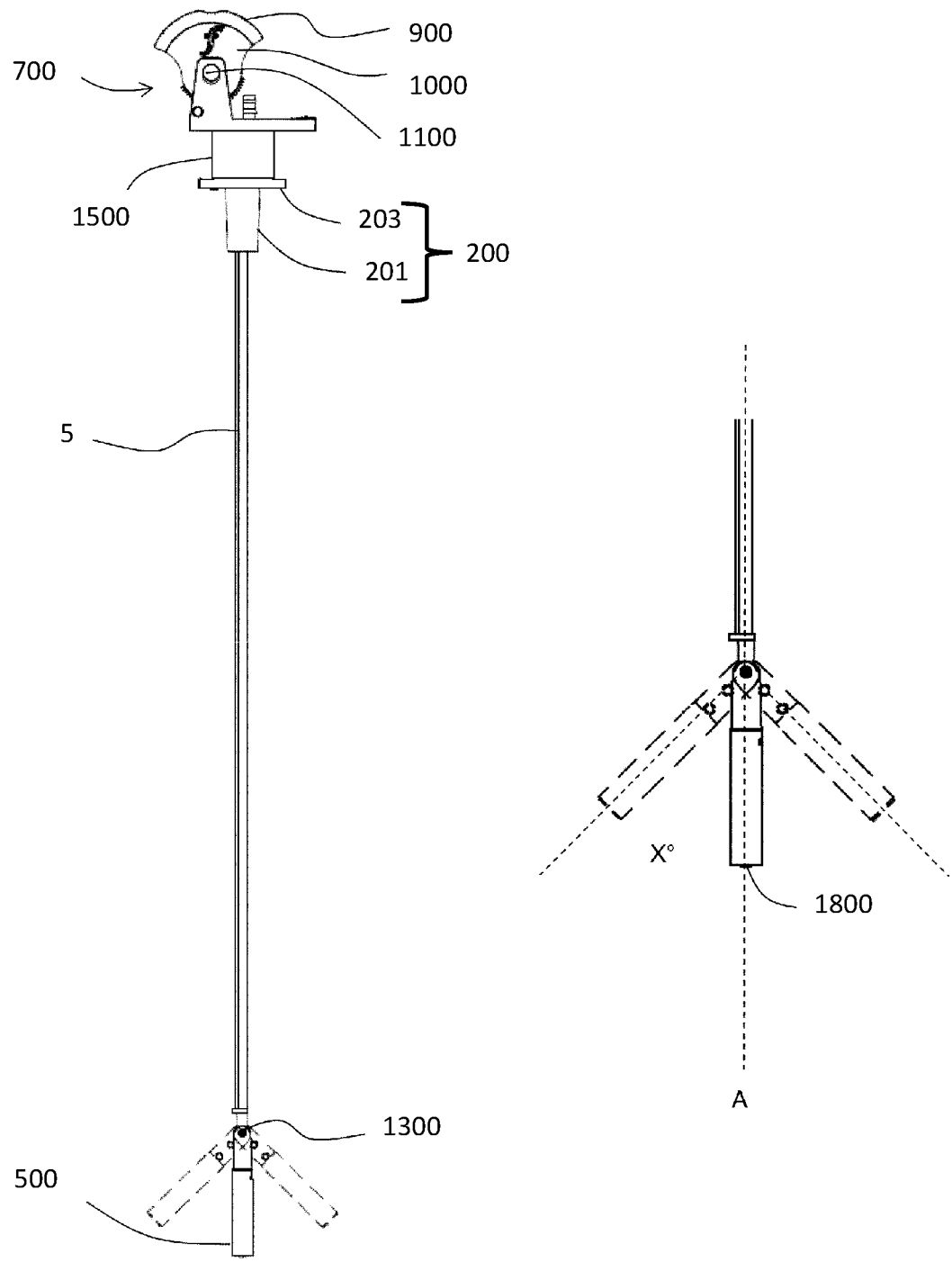
FIGS. 20A-20B, 20(A) shows a side aspect of a stylet showing movement of the angularly deflectable tip, and 20(B) a detail view of the angularly deflectable tip showing the deflection angle of the tip.

With reference to FIGS. 19-20, the stylet has an image acquisition element (1600) disposed at the end of the tip. This device is therefore positioned in such a way as to be able to capture images distal to the distal tip of the stylet. Where the stylet is used in combination with an ET, the image acquisition element will therefore capture images from the end of the ET. The images captured by the device may be transmitted in real time to a display device. Conveniently, there may be a wire (not shown) running along or inside the body of the stylet for electronically transmitting the image (s) from the image acquisition element at the stylet tip to such a display device. Where there is such a wire, it may be protected by a sheath. Other method of transmitting such images are also contemplated, including, for example, wireless transmission of image data. FIGS. 20 (*a*) and (*b*) show the range of movement of the pivotable tip in this stylet. The tip can pivot at the pivotable hinge within a pivot range ±X° from the longitudinal axis of the distal end of the stylet body, marked as axis A in FIG. 20 (*b*). In FIG. 20 (*b*) the pivot range is observed to be approximately ±45°, however depending on the exact configuration of the stylet, a pivot range of up to ±90° or ±180° may be possible. Advantageously, the tip can pivot in both directions from a ˆneutral' position where the tip is generally aligned with the stylet body. Accordingly, the stylet offers improved maneuverability of the stylet tip which can assist in more accurate guiding of an ET during an intubation process. The mechanism by which the pivoting of the tip is controlled is discussed in relation to FIGS. 21-23, below.

Figure 21:
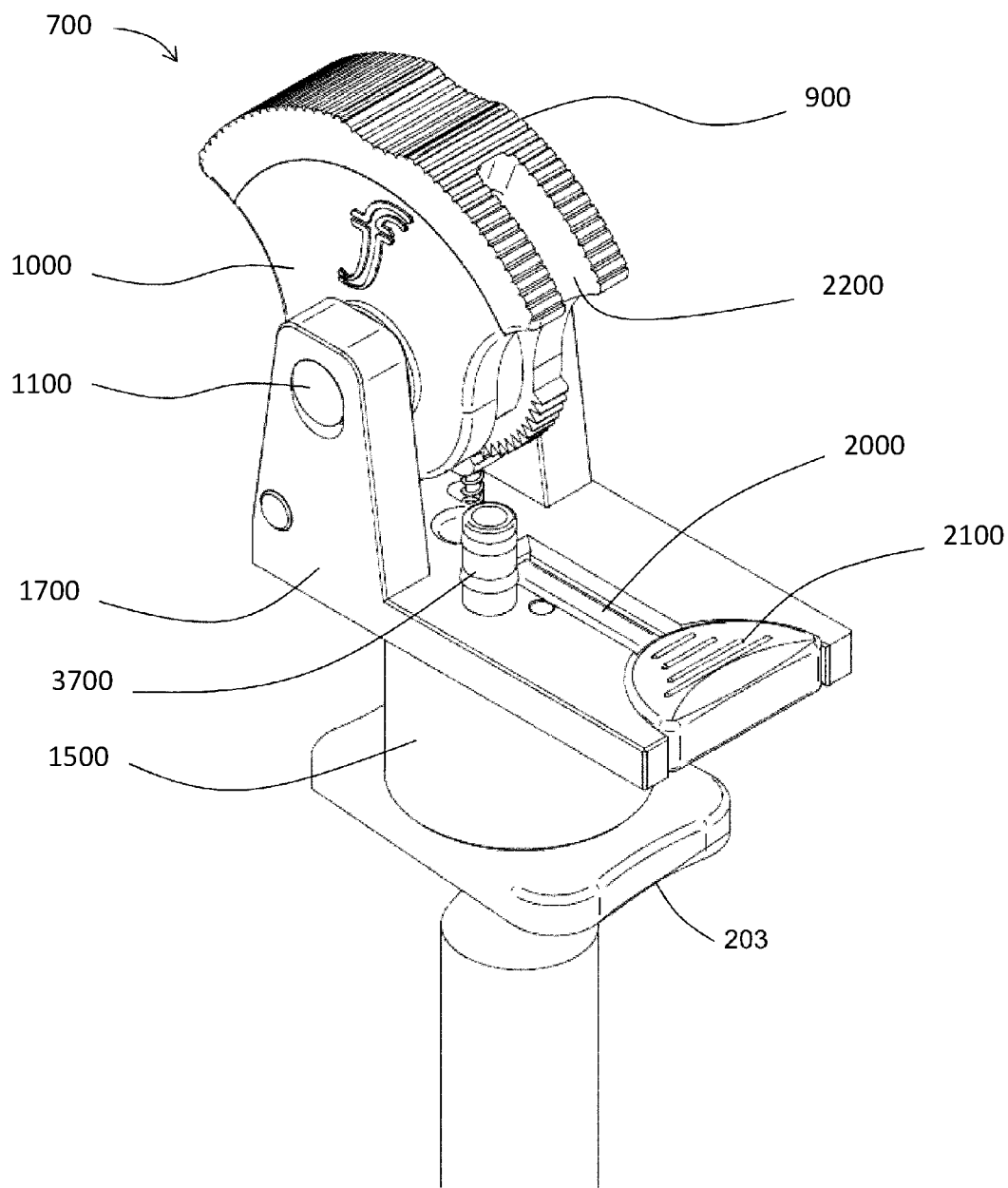
FIG. 21 shows a perspective view of an actuator control mechanism of the stylet of FIGS. 19 and 20 (control wire omitted).
Figure 22:
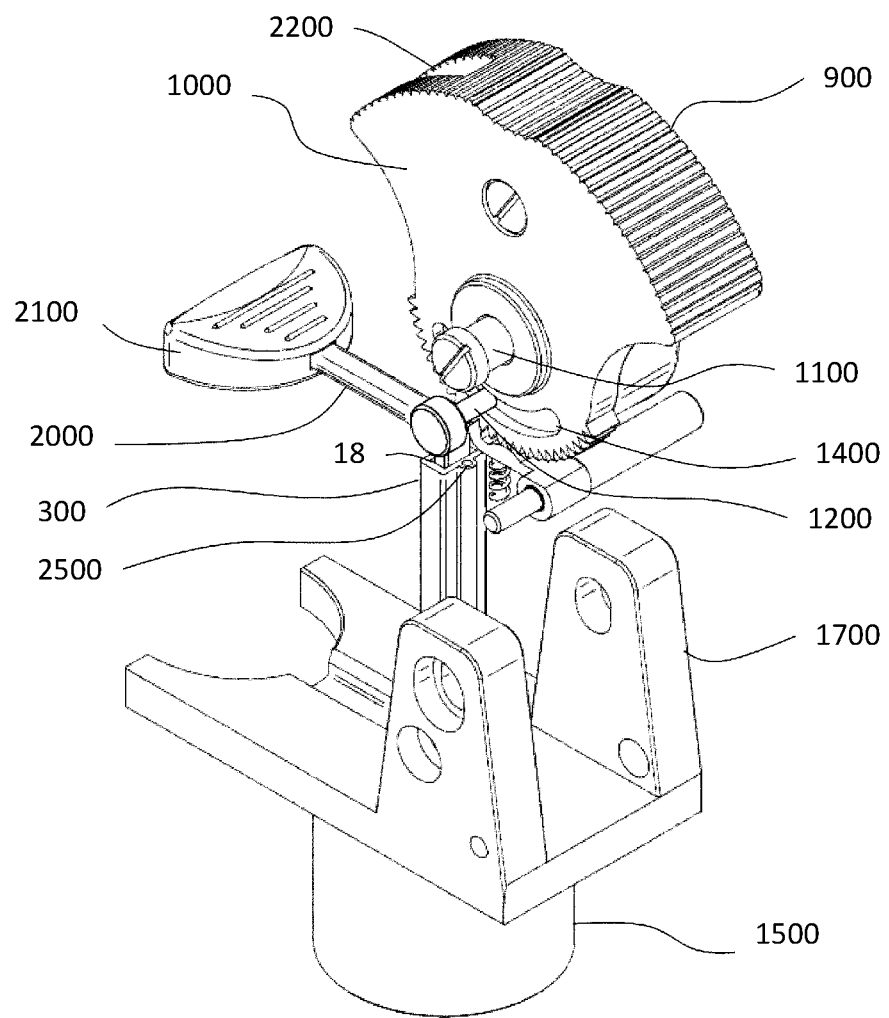
FIG. 22 shows a perspective exploded view of the actuator control mechanism of FIG. 21.

FIGS. 21 and 22 show respectively a perspective view and an exploded perspective view of an actuator of the stylet of FIGS. 19 and 20, with control wires omitted. FIG. 21 shows the actuator connected to an ET connector at attaching portion (1500). FIG. 22 does not include an ET connector. As described above, the mechanism has a thumb-pad (900) which can be manipulated to provide directional control of the tip of the stylet in a manner described in detail below. The thumb-pad is formed as part of a dial (1000) which is rotatable around an axle (1100) in response to forces on the thumb-pad provided by an operator. Here, the thumb-pad is shaped to for improved ease of use, including a ridged surface for increased grip by the operator, although this is not essential. The dial is attached to a body or retaining housing (1700) of the actuator via the axle (1100). Attaching portion (1500) is integrally formed with the body of the actuator. This may provide improved ease of manufacture of the device.

The actuator has a sliding pin and slot arrangement having end stops arranged to restrict the movement range of the actuator (and correspondingly restrict the movement range of the stylet tip) . Here, the pin (1200) is arranged to project from the actuator body (1700) to engage slot (1400) formed in the dial (1000) of the actuator. As the actuator dial is rotated, the slot moves in relation to the pin until the pin hits an end of the slot, preventing further relative movement of the components.

A handle portion (2000) of a malleable titanium rod (1900) is visible, the remainder of the rod being removably disposed within a central lumen (1800) of the tubular stylet body (300). The malleable rod here has a rectangular cross section, with the central lumen of the stylet body being correspondingly rectangular. The handle has a ridged gripping portion (2100) to aid removal and insertion of the rod. Here the handle portion of the rod lies within a recess formed in the body of the actuator, which can prevent the handle from obstructing the actuator during use. In use, the malleable rod can either be removed from the stylet completely, or can be bent into a desired shape to aid in insertion of the stylet and ET through vocal cords. In this particular embodiment, the dial of the actuator has a notch (2200) which enables the malleable rod to be removed easily without obstruction by the dial.

Figure 12:
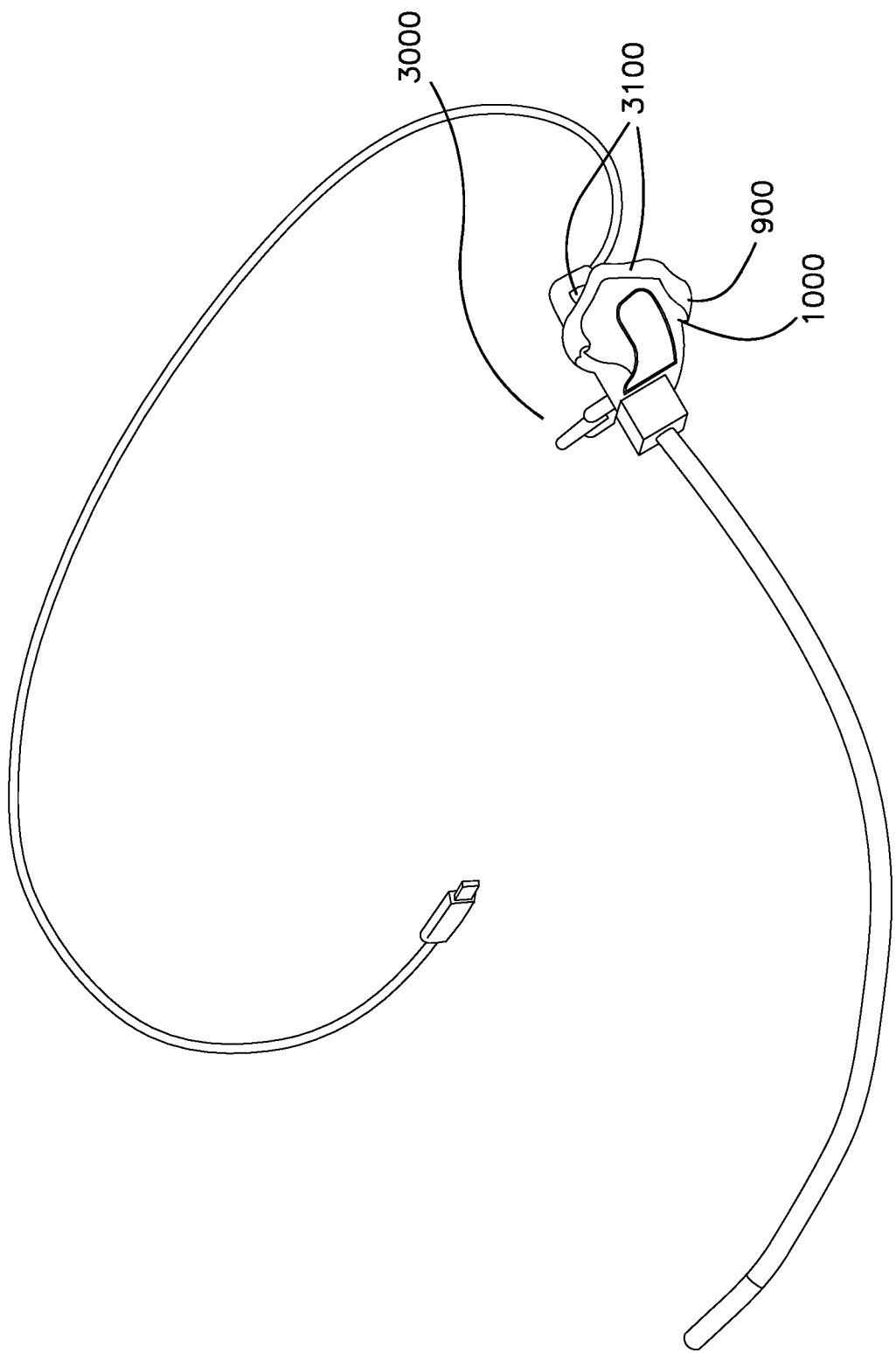
FIG. 12 is a side view of one embodiment of a stylet of the disclosure with a deflected distal tip.
Figure 13:
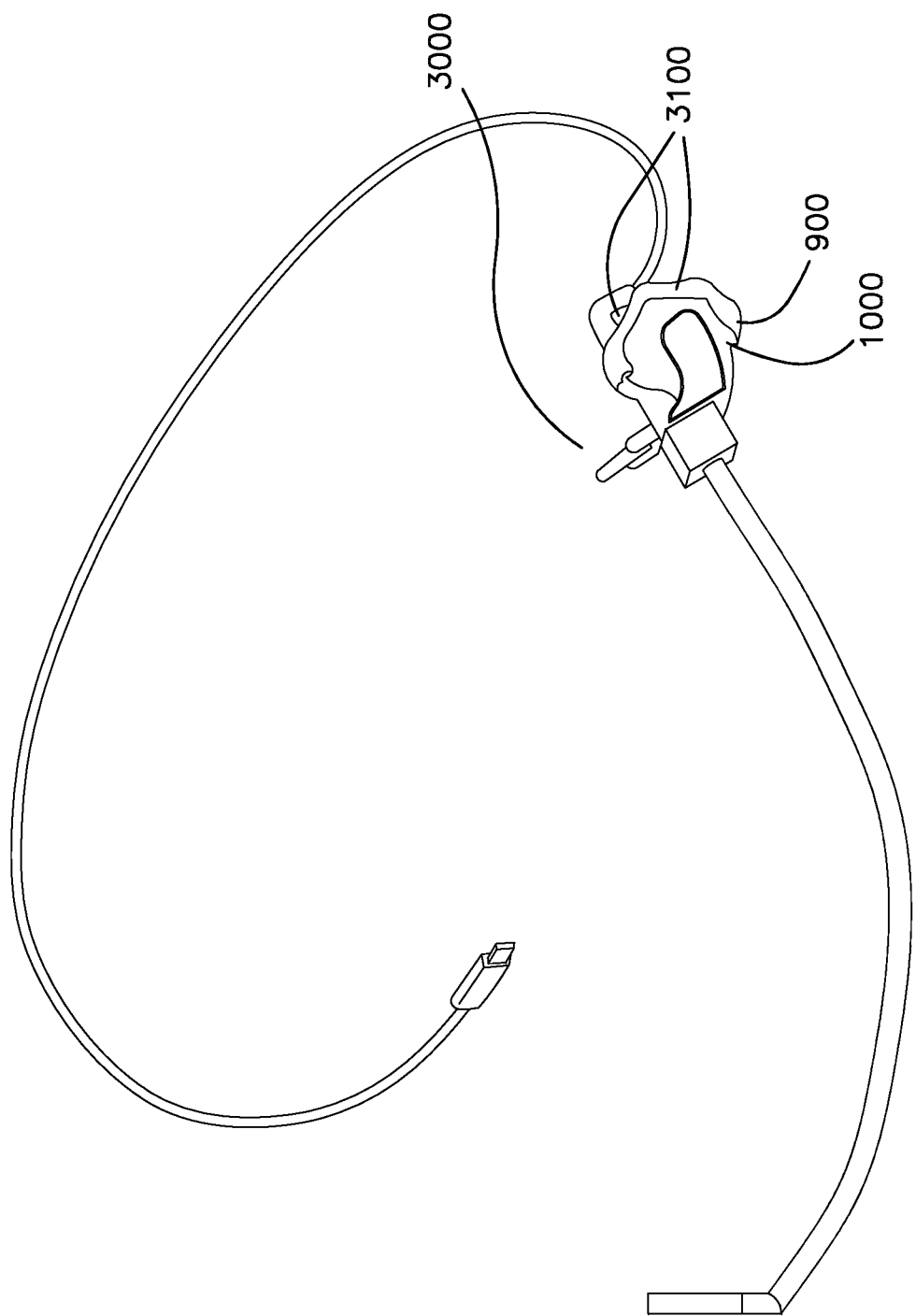
FIG. 13 is a side view of the stylet of FIG. 12.
Figure 14:
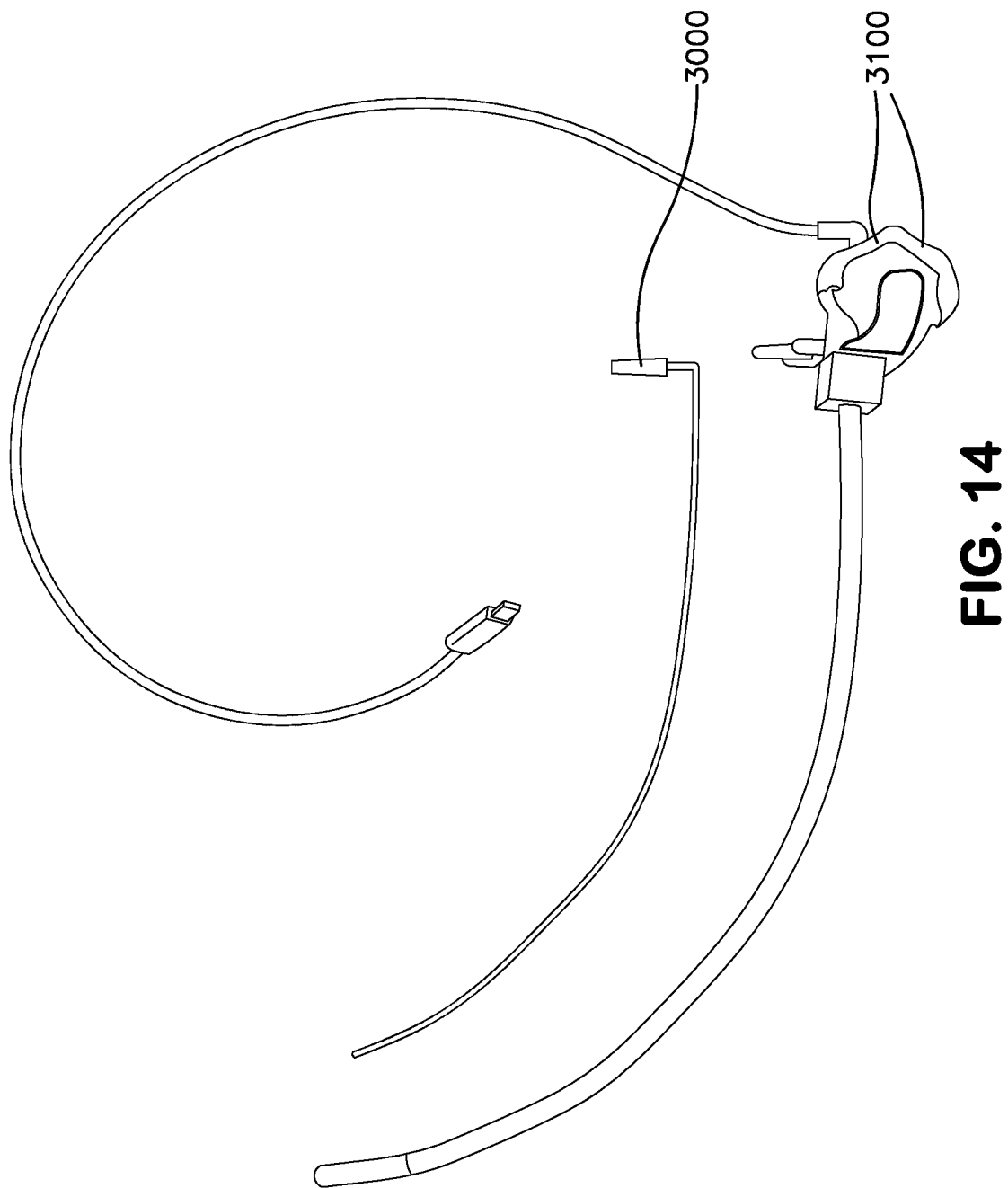
FIG. 14 is a side view of the stylet of FIG. 12 wherein the malleable rod is removed from the stylet and shown separate from the stylet.
Figure 15:
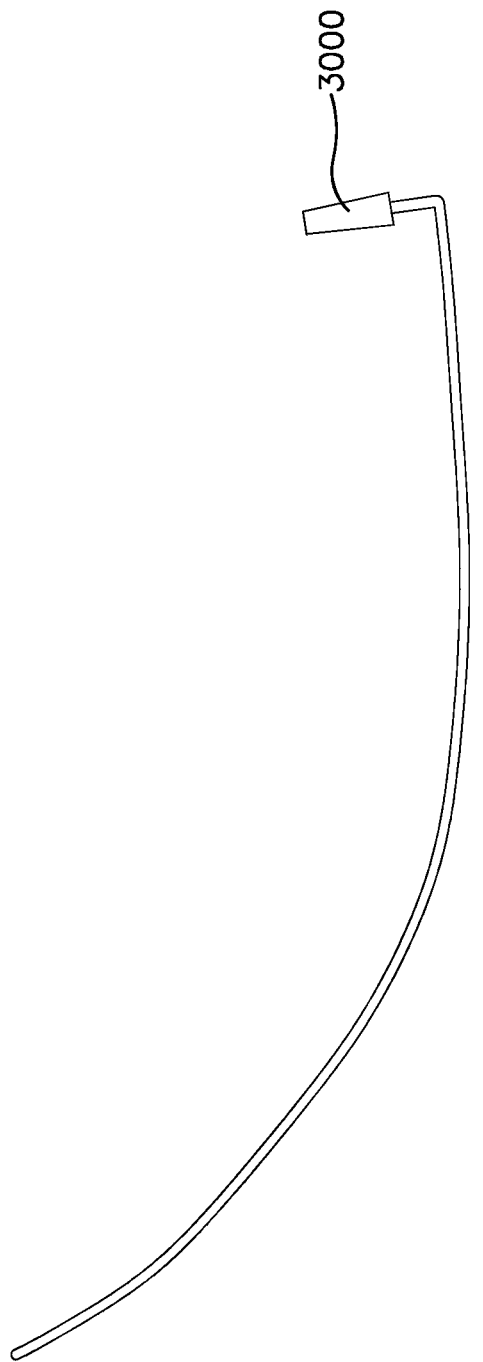
FIG. 15 is a side view of the malleable rod of FIG. 14.
Figure 16:
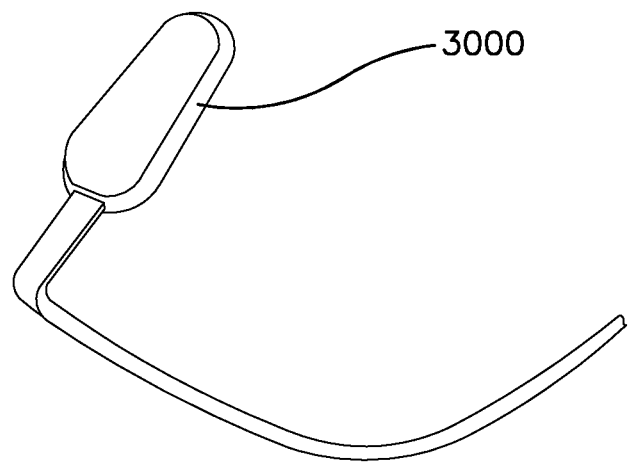
FIG. 16 is an expanded perspective view of the tab region of the malleable rod of FIG. 15.
Figure 17:
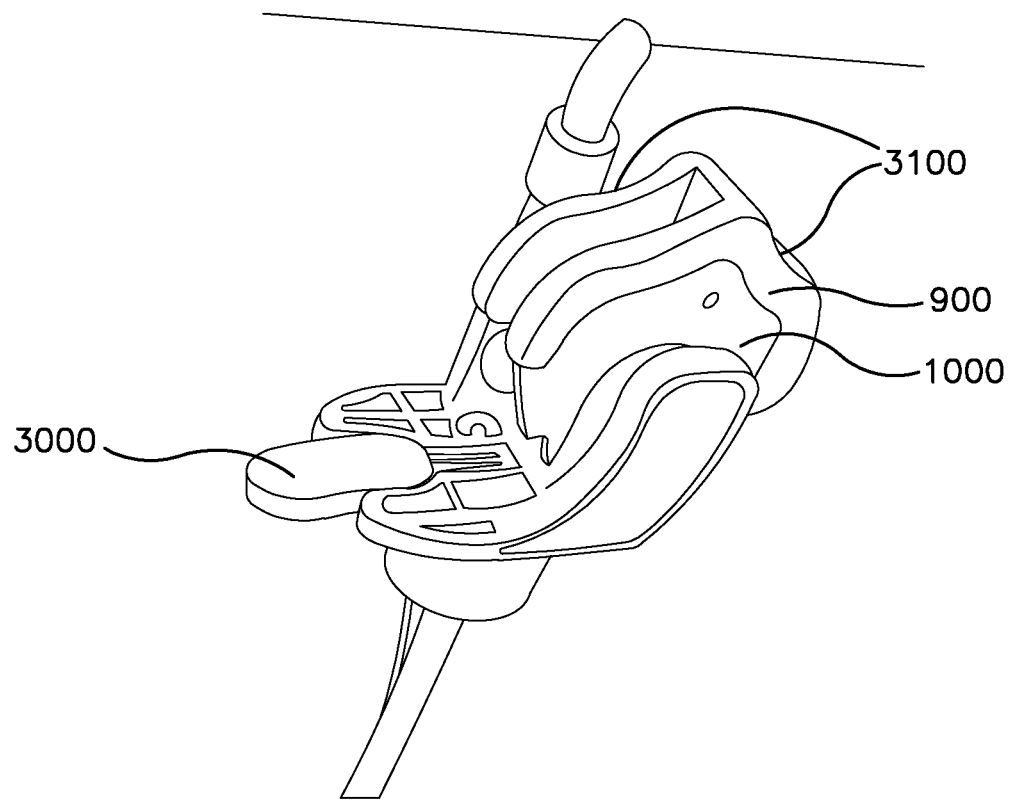
FIG. 17 is an expanded perspective view of the proximal end of the stylet of FIG. 12.
Figure 18:
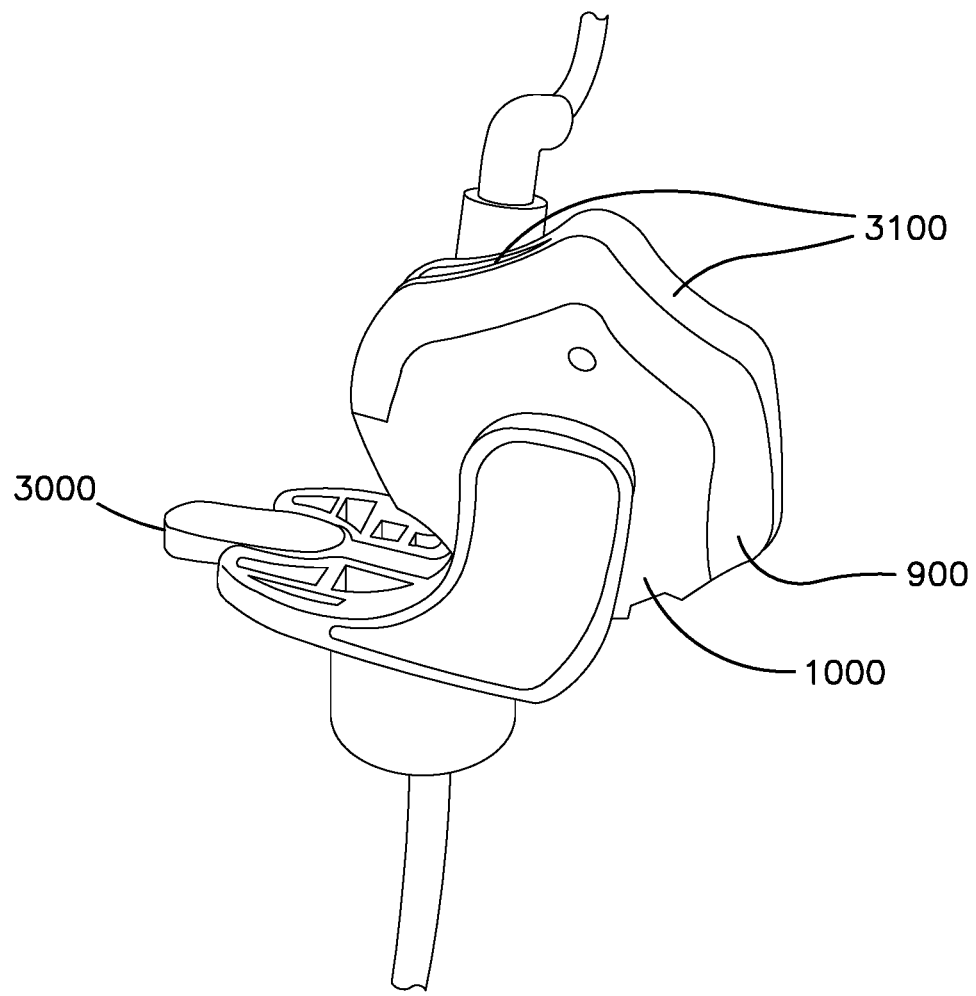
FIG. 18 is an expanded side view of the proximal end of the stylet of FIG. 12.

FIGS. 12-14 illustrate a stylet of the invention which is substantially the same as that of FIG. 19. However, the handle portion of the malleable rod includes a tab (3000) that has a tip that extends beyond the housing when the rod is disposed within the stylet body to facilitate contact with a digit of the user. In embodiments, the tab may be configured as a disk having a circular, elliptical, square, triangular, or rectangular shape. FIGS. 12-18 illustrate a malleable rod in which the tab (3000) is generally elliptical.

The stylet further has a port (3700) located on the body of the actuator for attachment to an air or oxygen line. The port passes through the actuator body into a cavity defined by the attaching portion (1500). Thus, when the stylet is attached to an ET via an ET connector, air or oxygen can be provided into the ET via this port on the stylet. The port may have a ridged outer surface to help retain an oxygen line which is connected to the port.

FIG. 23 shows a sectional view of an actuator of FIGS. 21 and 22. There is a control wire (2300) extending round a central drum (2400) of the actuator dial and attached to a retaining portion (2500) to hold its circumferential position. Turning the drum adjusts the pivot angle of the tip of the stylet. In this embodiment, there is a single control wire which is attached to the retaining portion at its center, thus providing a first control wire portion and a second control wire portion which extend down to opposing sides of the pivotable tip, as shown in FIGS. 24(*a*) and (*b*). As the dial of the actuator is rotated, tension is applied to one or other of the two wire portions. By applying tension to the first wire portion, the tip can be moved in a first direction. By applying tension to the second wire portion, the tip can be moved in a second direction. Whilst here the first and second wire portions are part of a single wire, they may alternatively be two separate control wires, and may be attached to a single retaining portion, or separate respective retaining portions, of the actuator.

Conveniently, the stylet body may have one or more wire retainers (2400) formed on the body as shown in FIG. 24(*a*). Such retainers can help to hold the control wire(s) flush against the stylet body and avoid snagging of the wires during use. Alternatively or additionally, at least a part of one or more of the wire portions may run inside a channel (2500) formed in the stylet body, as shown in FIG. 22.

The dial (1000) has a toothed portion (2700), the notches of which engage with a spring-loaded detent (2900) to provide a series of incremental stop points. The detent (2900) is on an arm pivotable about a pivot axle (3100), and affixed to a spring (3300) at the opposing end. Accordingly, the detent is biased into engagement with the notches on the dial (1000) by the spring force of the spring. As a user rotates the dial (1000) to adjust the pivot angle of the stylet tip, this rotational movement of the toothed portion of the dial forces the detent out of engagement with the notches against the spring force, until the detent can click into the subsequent notch. In this way, the mechanism allows for relatively smooth incremental adjustment of the pivot angle of the stylet tip. One further advantage of the particular mechanism shown is that the user does not need to continuously provide input to the control mechanism to keep the stylet tip at a desired angle. Once the pivot angle of the tip has been set by rotation of the dial, the detent holds the dial in the selected position until it is again adjusted by the user. This means that the user can let go of the actuator to perform other actions as needed.

Figure 35:
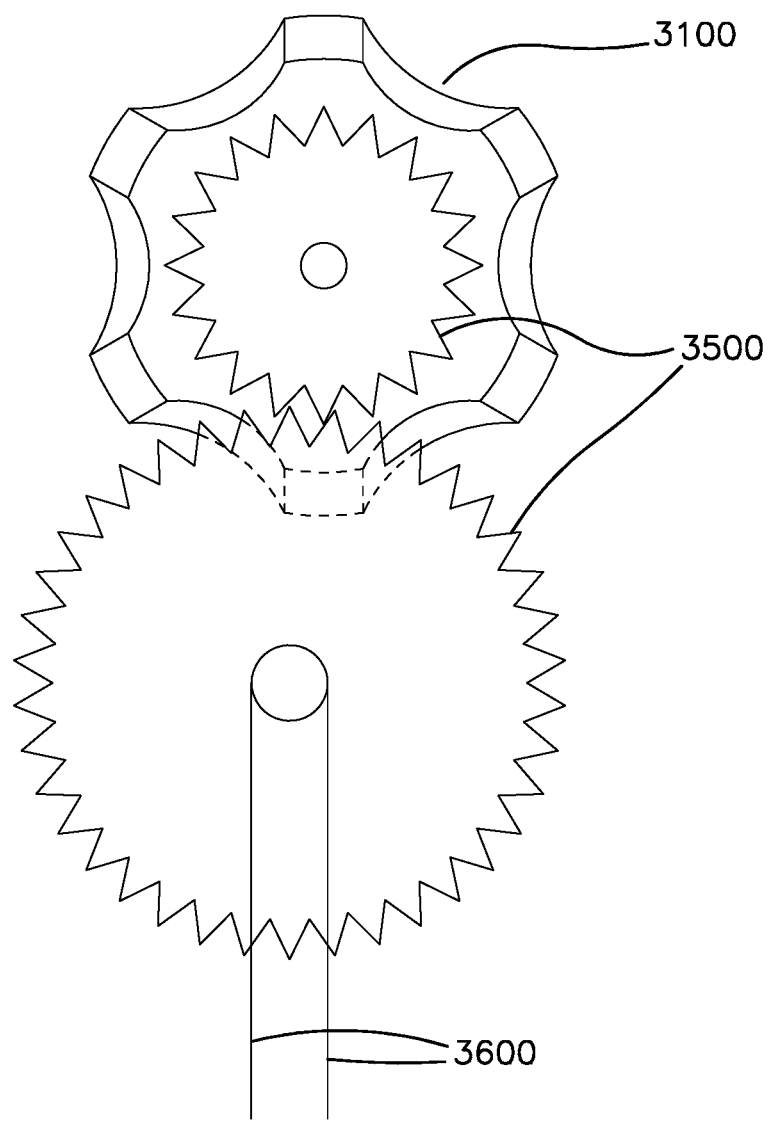
FIG. 35 illustrates an embodiment of the control mechanism of the actuator which includes torque generating gears for reducing the amount of force required by the operator to manipulate the stylet.
Figure 36:
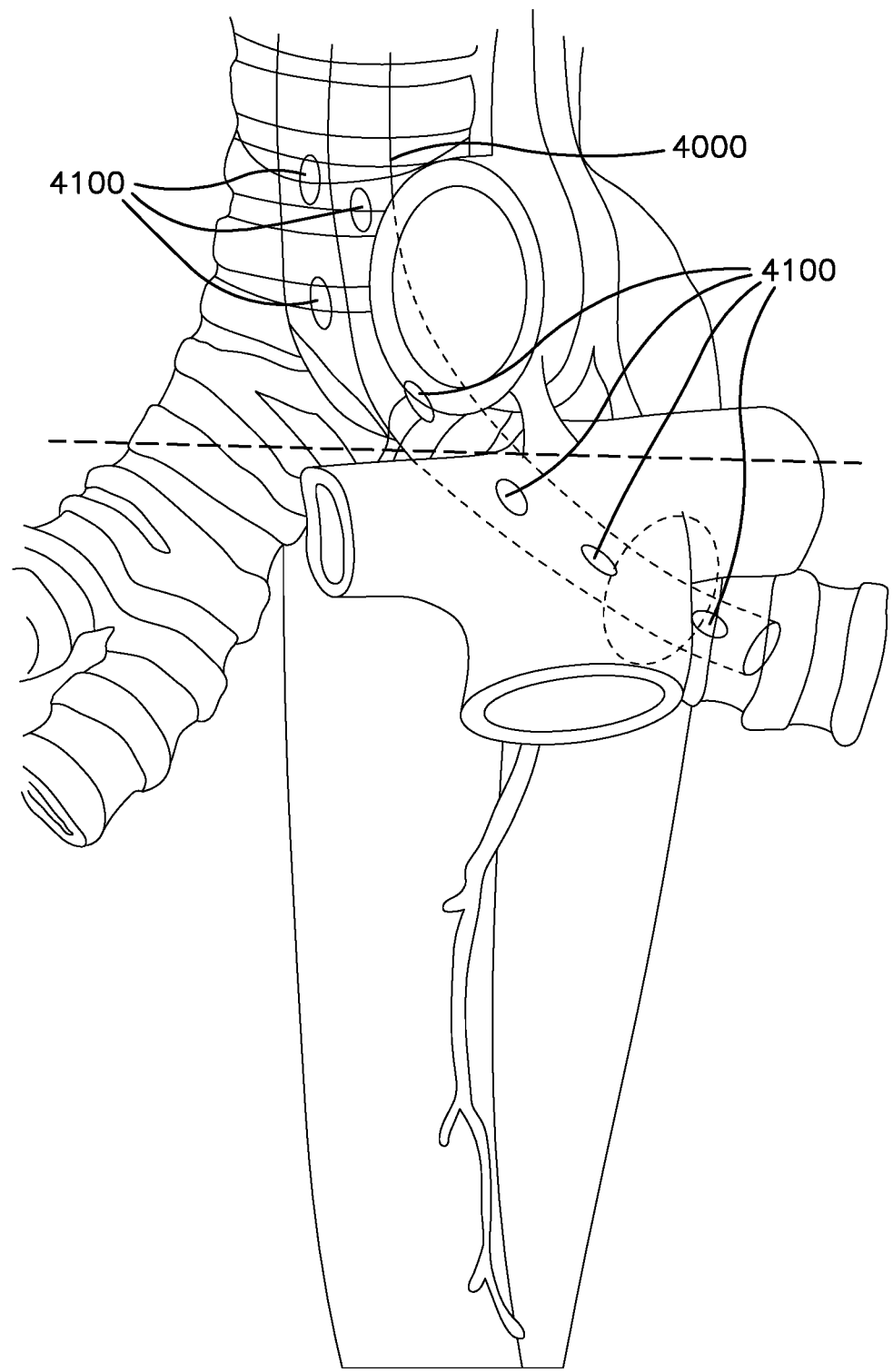
FIG. 36 illustrates a double lumen ET in one embodiment of the invention which includes multiple sensors disposed along the length of each tube
Figure 37:
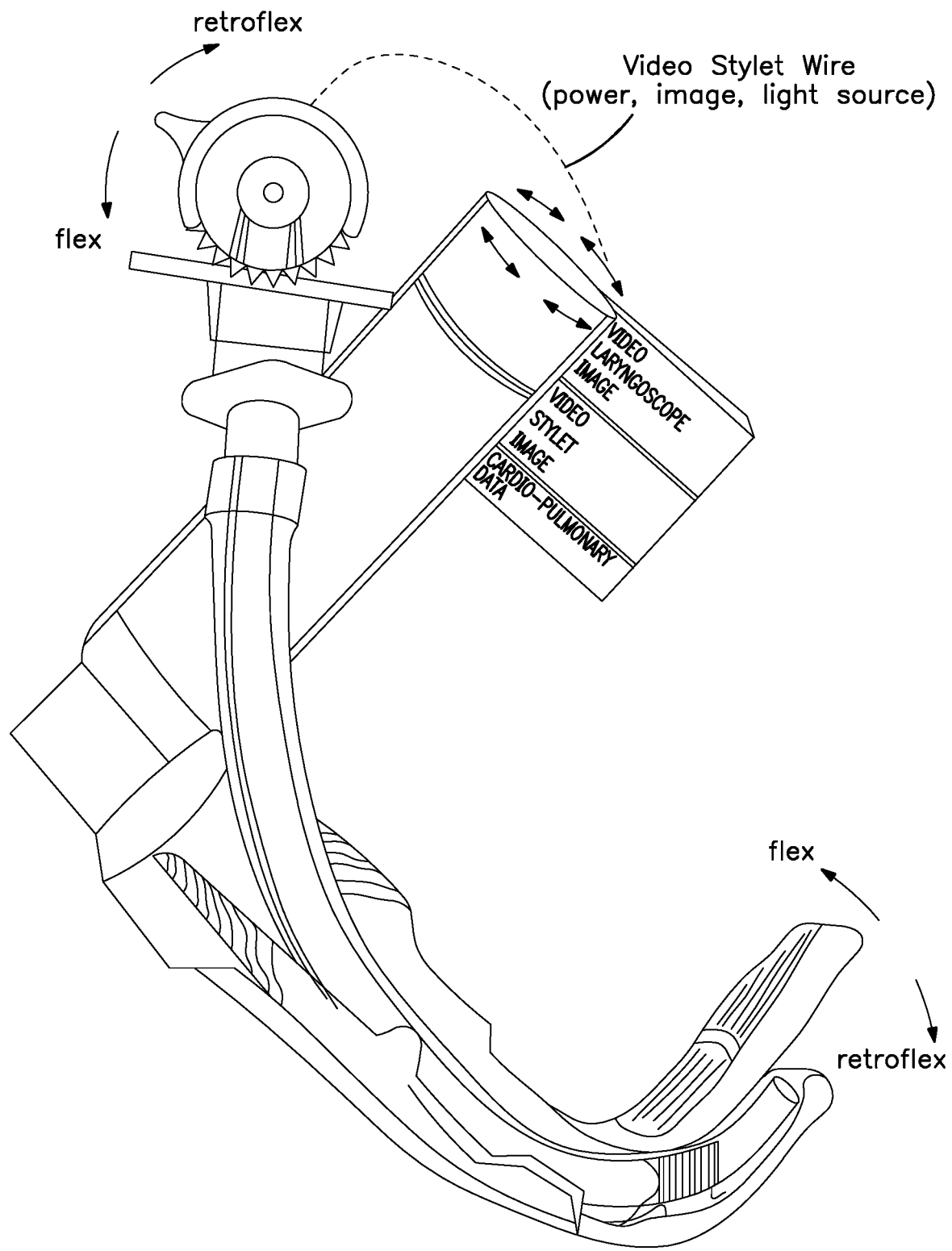
FIG. 37 illustrates a video laryngoscope utilizing a stylet of the disclosure in one embodiment of the invention.
Figure 38:
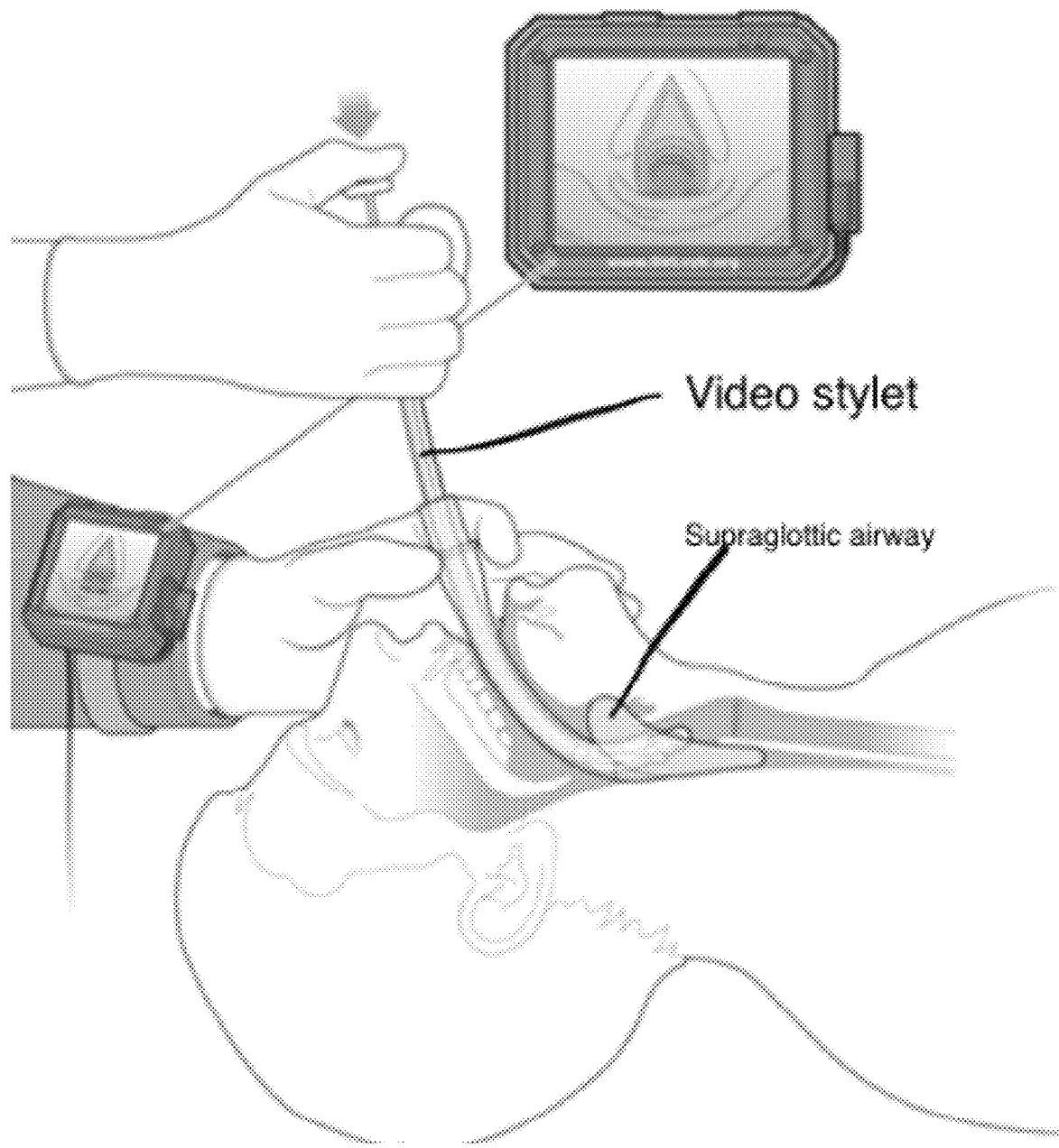
FIG. 38 is a schematic view of a stylet of the disclosure in use in one embodiment of the invention.
Figure 39:
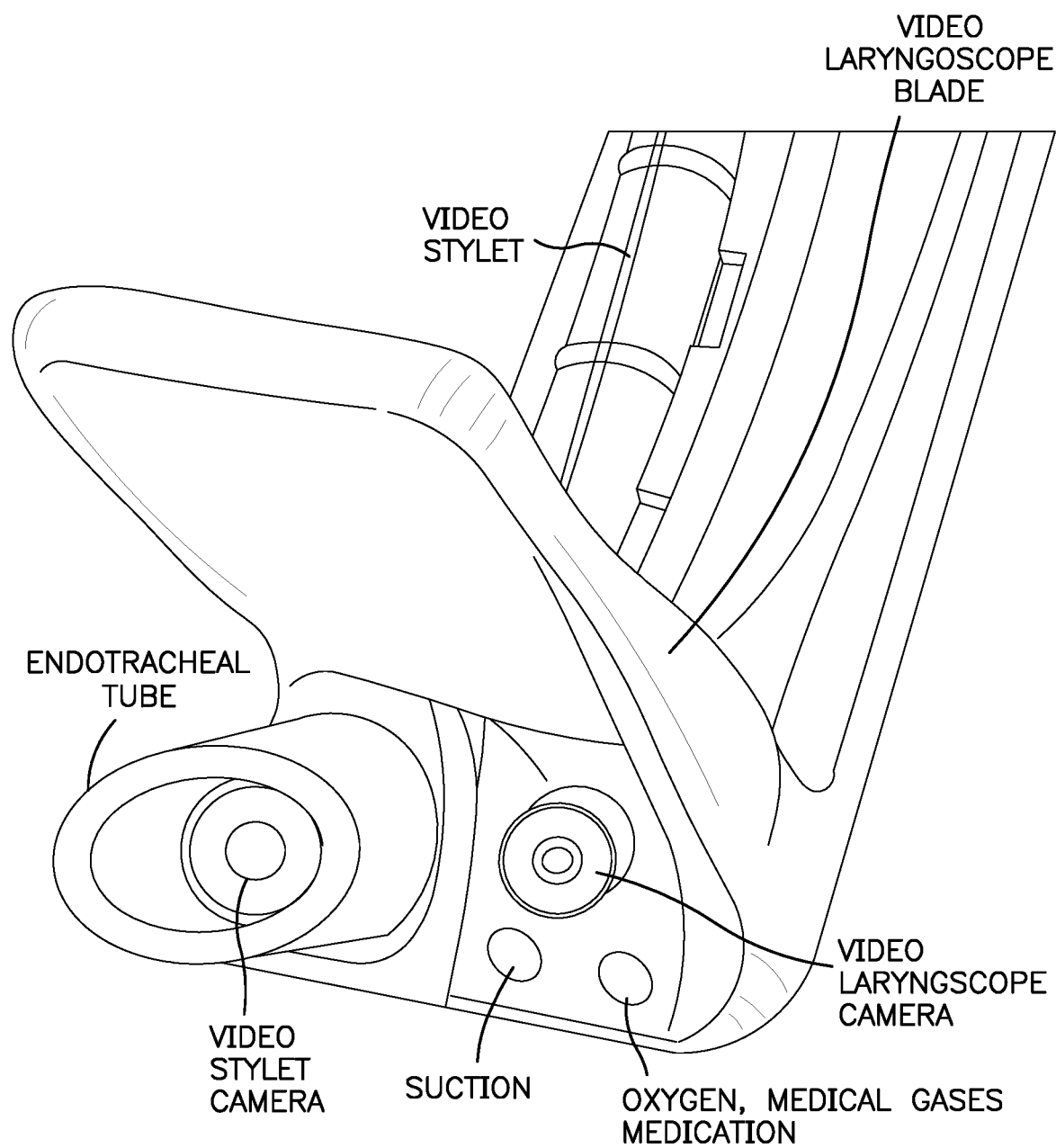
FIG. 39 illustrates a video laryngoscope utilizing a stylet of the disclosure in one embodiment of the invention. Also illustrated are various connectors.

FIG. 35 illustrates an embodiment of the stylet which includes one or more gears (3500) in operable connection to a dial (3100) of the actuator. The one or more gears (3500) are configured to interact with the flexible shafts or control wire(s) (3600) disposed within the stylet body. The one or more gears (3500) allows the amount of force required by the operator to manipulate the dial (3100) to be reduced.

Figures 25A, 25B, 25C:
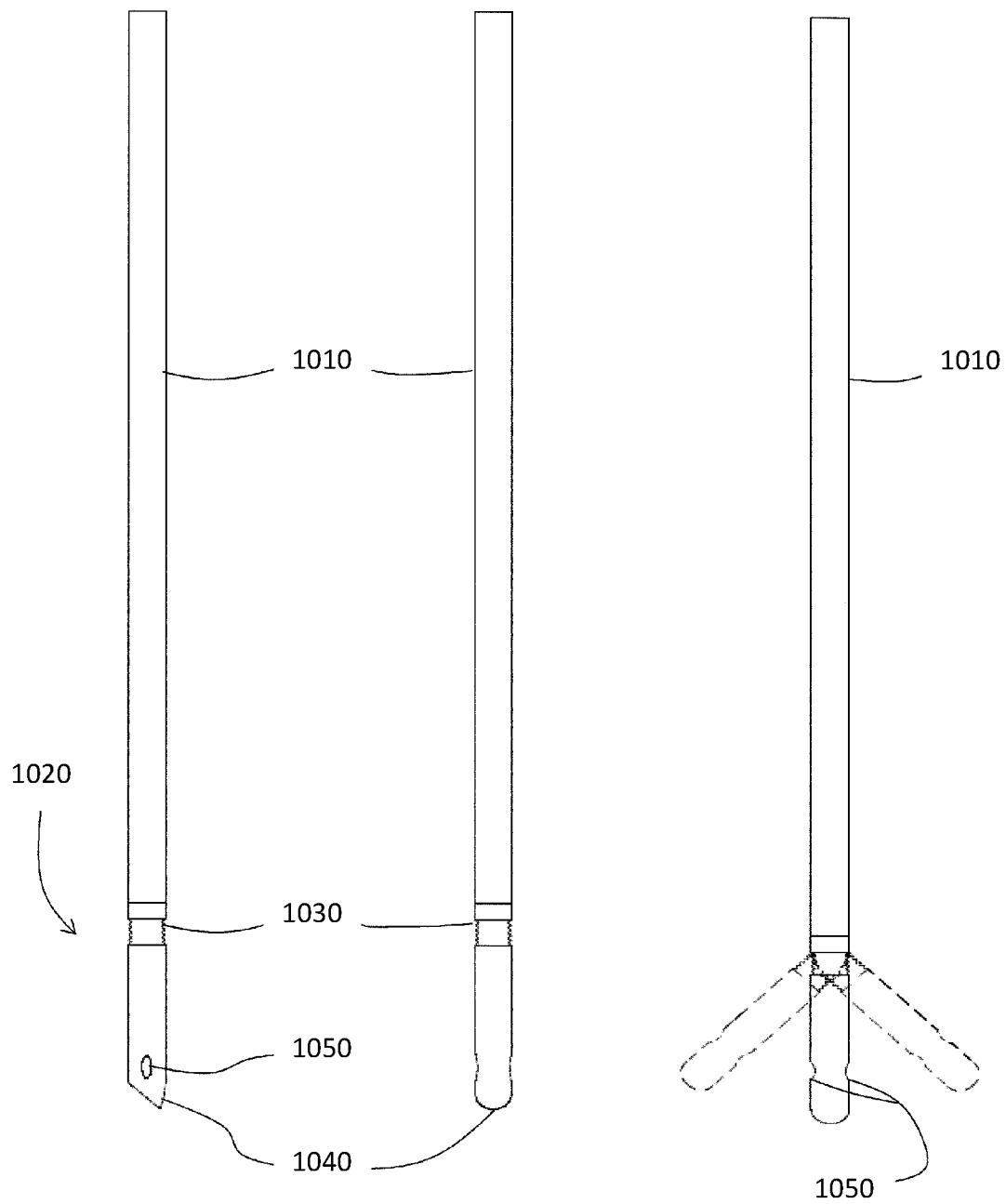
FIGS. 25A-25C, 25(A) shows a side aspect and 25(B) a front aspect of a first embodiment of an ET, and further shows 25(C) a side aspect showing bending of the flexible bending segment of the ET.

FIGS. 25 (*a*)-(*c*) show a first embodiment of an ET. The ET has a body 1010 which comprises a flexible hollow tube. The ET body may typically be made from e.g. PVC, although the skilled person will be aware of a range of other suitable materials. The distal end of the tube is inserted into a patient's trachea during intubation. The proximal end of the ET may be removably attached to an ET connector for connection to a ventilation system, although this is not shown in these drawings. The ET has a bending portion (1030) located towards the distal end (1020) of the body, intermediate the body and the distal tip portion (1040) of the tube. The bending portion is here formed as a concertina portion of the tube to promote preferential bending at that position. The concertina allows for increased bending of the bending portion in comparison to the general flexibility of the body of the ET, as demonstrated in FIG. 25 (*c*). The length of the concertina portion is not particularly limited, but should allow a suitable range of angular movement at the bending portion without excessive strain in the material. The position of the bending portion along the length of the ET is selected in this embodiment such that when used in combination with the stylet described above, the pivot hinge of the stylet will align with the bending portion of the ET.

The ET includes two Murphy eyes (1050) formed at the distal end of the tube, on opposing sides of the tube. These openings provide alternative flow paths for air in the cause of occlusion of the main outlet of the tube. The Murphy eyes are sized to limit or prevent protrusion of a stylet through the openings. The skilled person will be well aware of a wide variety of features which the ET may incorporate but which are not pictured here, including but not limited to an inflatable cuff and corresponding inflation line with pilot balloon, a radio opaque line to enhance imaging of the tube, and markings on the tube to guide positioning of the tube. The ET may further include markings or color coding for identification of depth of insertion when the ET is advanced in an intubation conduit to identify the exact depth of insertion where the endotracheal tube's flexible bending segment has exited the intubation conduit distally and is able to be deflected without impedance. Corresponding marking or color coding may be placed on the stylet as well to provide identification of the stylet's exact depth of insertion where the stylet's deflection point of the deflectable section has exited the intubation conduit distally and the stylet is able to be deflected without impedance.

Figure 26:
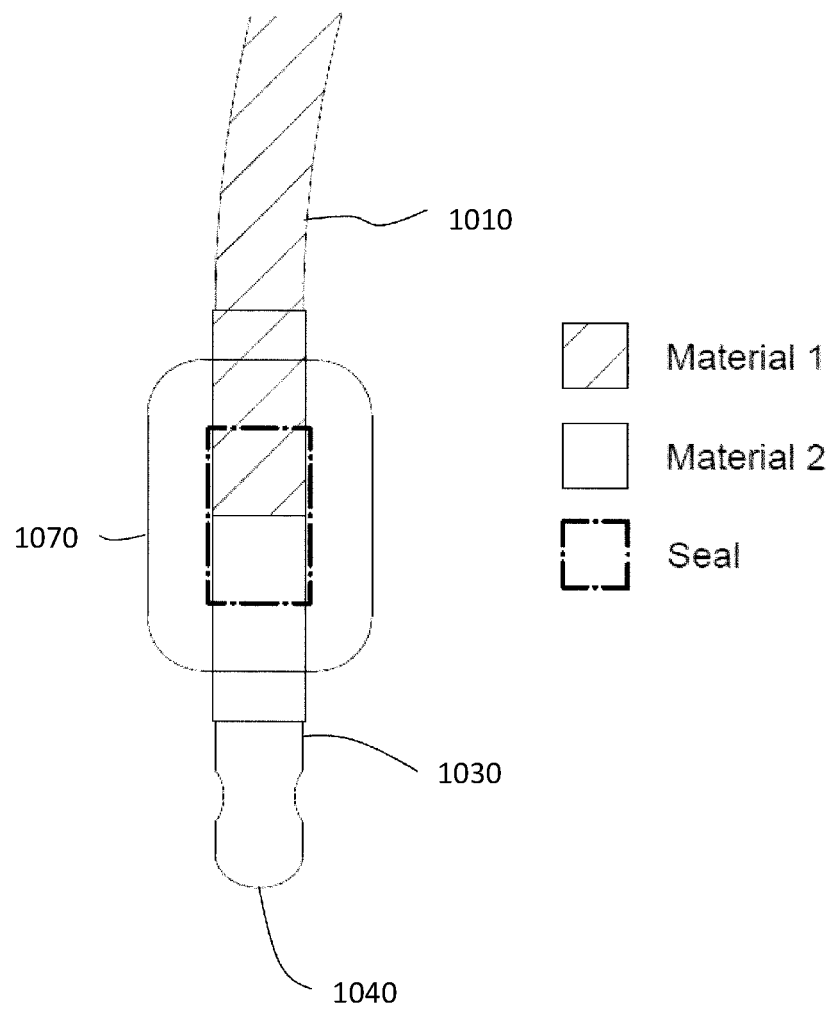
FIG. 26 shows a schematic view of a second embodiment of an ET.

FIG. 26 shows a schematic view of a second embodiment of an ET. In this embodiment, the bending portion (1030) is a portion of the tube made from a different material to the material of the body (1010) of the tube. Here, the body of the tube is made from a first type of PVC, and the bending portion is made from a second, softer PVC, although it may also be possible to use e.g. silicone. The body and the bending portion are connected together using a seal (shown as a dashed rectangle) which extends across the join between these portions. The material chosen for the bending portion should typically be more flexible than the material of the body of the ET, to allow increased ease of bending the bending portion compared to the body of the ET. In this embodiment, the bending portion (1030) includes the distal tip portion (1040) of the ET.

In this particular embodiment, an inflatable cuff 1070 is also shown. Such a cuff is a standard feature of many well-known ET designs, and as such, the size and shape of the cuff is not particularly limited. Furthermore, the material which the inflatable cuff is made from is not particularly limited and the skilled person will be well aware of a number of suitable materials which could be used for this purpose.

In alternative embodiments, the bending portion may not be formed of a different material, but may be made of the same material having a lower density than the body of the ET. Alternatively or additionally, the bending portion may be locally thinned for increased flexibility. It is also considered that any of the above proposed features of the bending portion may be used in combination. The bending portion may be, for example:

a concertina portion formed from a different material to the material of the ET body;

a locally thinned portion formed of a different material to the material of the body;

a locally thinned concertina or bellows portion; etc. or a wire reinforced flexible bending segment or an entire ET that is wire reinforced to allow deflection while preventing kinking of the ET.

Figures 27, 28:
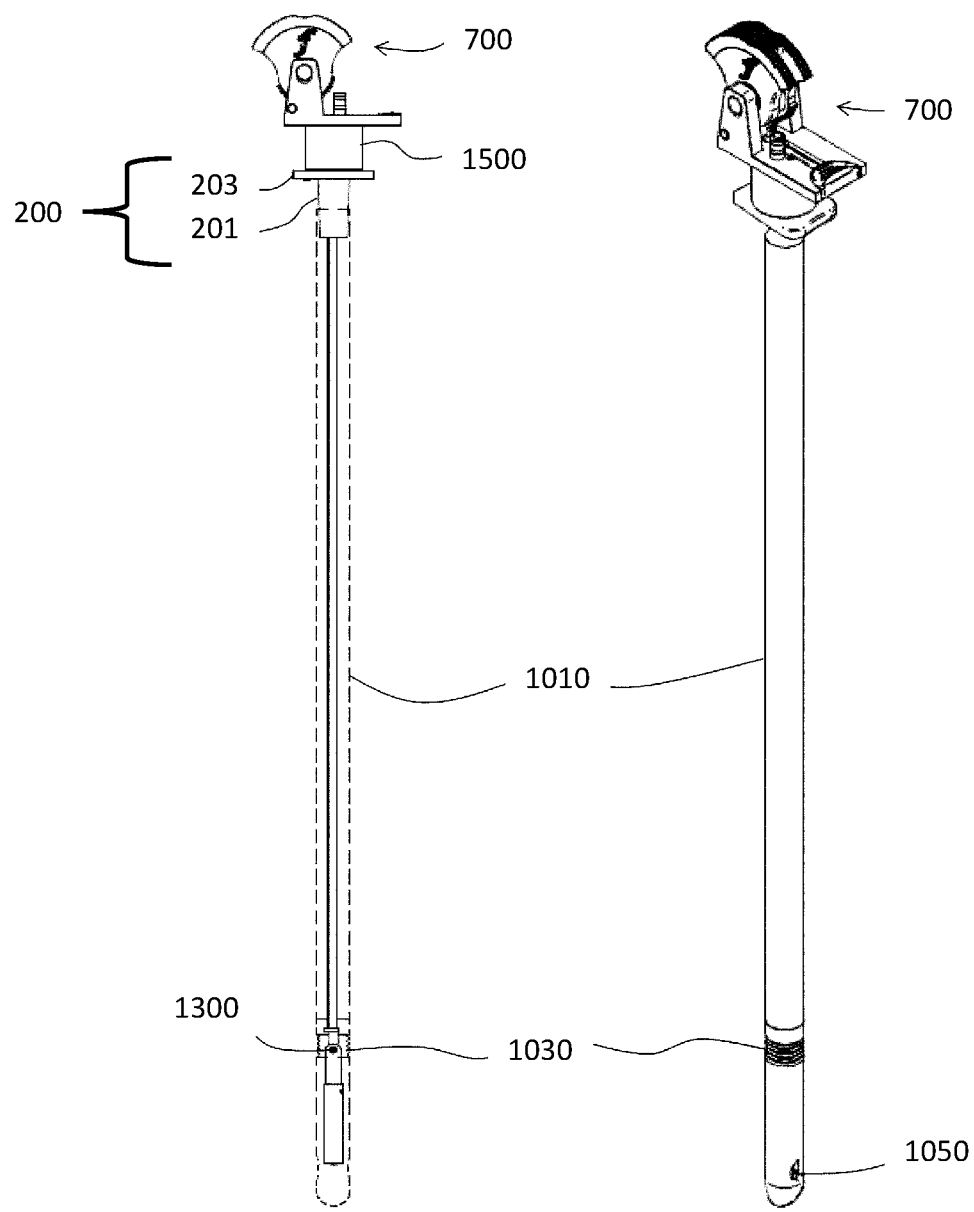
FIG. 27 shows a schematic view of an intubation kit.
FIG. 28 is a perspective view of the kit.

FIGS. 27 and 28 show views of an intubation kit, including a stylet of the first aspect and an ET of the second aspect, in addition to an ET connector (200). The ET shown here is an ET having a concertina or bellows flexible bending segment. In FIG. 26, the ET is shown as a dashed line. In this figure, it can be seen that the ET fits onto the tapered portion (201) of the ET connector. The ET described in this application can be alternatively designed in the form of a Nasal RAE ET, Oral RAE ET, NIM (Neural Integrity Monitor) ET, or standard single or double lumen ET.

Furthermore, the position of the stylet inside the tube can be visualized. Here, the location of the flexible bending segment (1030) is selected to align with the location of the angularly deflectable hinge (1300) of the stylet when the stylet and the ET are connected. Typically, the length of the stylet and ET respectively will be selected such that the stylet does not protrude from the end of the ET when the ET is connected to the stylet. This is because where the stylet protrudes from the end of the ET, there is a risk that it could cause damage to a patient's airway during the intubation due to the more rigid nature of the stylet (in particular, any rigid elements at the stylet tip) in comparison to the ET.

Figure 29:
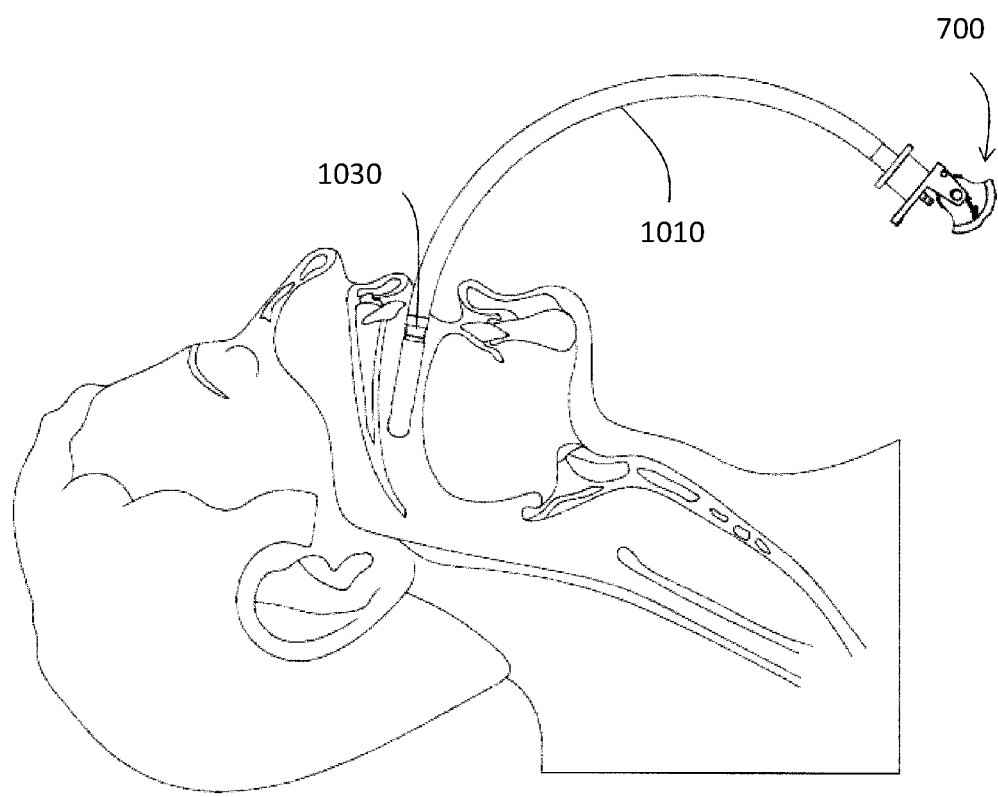
FIG. 29 is a schematic view of the kit in use.

FIG. 29 shows a schematic view of the intubation kit of FIG. 28 in use in an intubation process. As can be seen from the drawing, the ET body (1010) is generally flexible along its length and can curve to fit the patient's airway. The additional flexibility provided by the bending portion (1030) of the ET allows for ease of manipulation of the distal end of the ET using the pivotable stylet tip, which is controlled by a user using the actuator (700) of the stylet which remains outside of the patient's body during use. Due to the location of the image acquisition element in the stylet tip, the user can more easily guide the ET into the desired location by visualization of the airway from the distal end of the ET.

The kit can be used to perform an intubation process, including steps of a) inserting the stylet into the ET, b) inserting the stylet and ET into the airway of a patient, c) visualizing the airway of the patient using the image acquisition element disposed on the stylet tip, d) guiding the ET and stylet through the vocal cords of the patient into the trachea of the patient, and e) removing the stylet from the ET.

Figure 32:
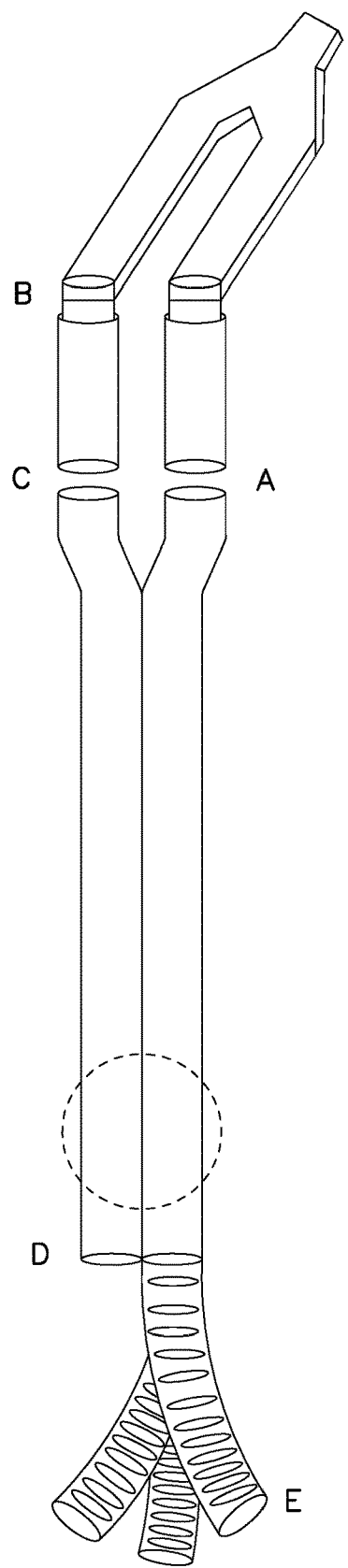
FIG. 32 is an ET in one embodiment of the invention.
Figure 33:
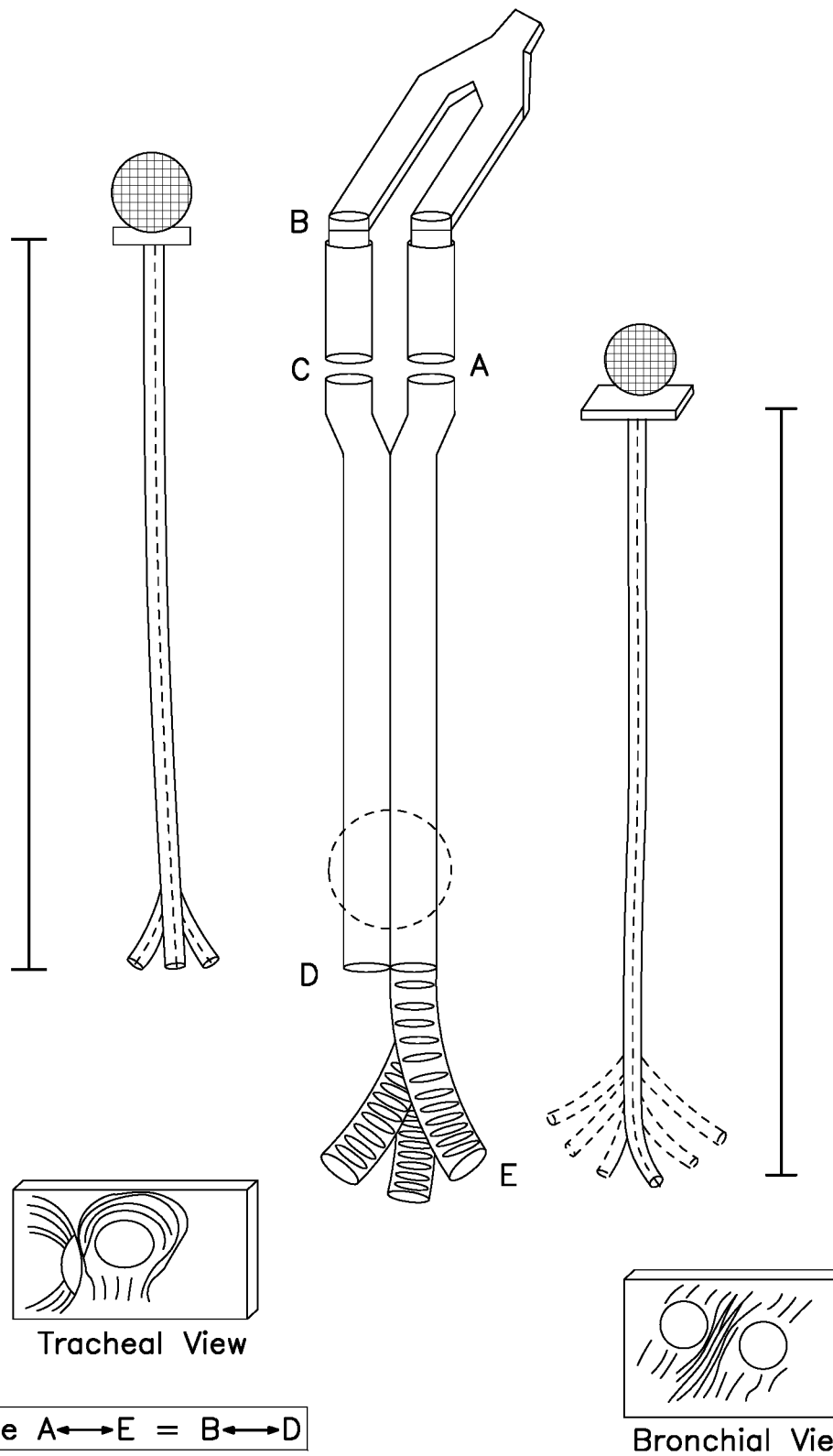
FIG. 33 illustrates use of the stylet depicted in FIGS. 30 and 31 with the ET of FIG. 32.

As discussed herein, the stylet of the invention may be preloaded in a single or double lumen ET. In embodiments the stylet is used with a double lumen ET as shown in FIG. 32. FIG. 33 illustrates an embodiment of use of a double lumen ET with the stylet shown in FIGS. 30 and 31.

In one embodiment, the stylet is adapted for use with a double lumen ET for one lung ventilation (OLV). Double lumen ETs have two lumens; a bronchial lumen that is placed so it's distal opening is in the left or right main stem bronchus and a tracheal lumen that is placed so it's distal lumen is in the trachea. The two lumens form one lumen proximally via an extension piece that allows either lumen to be clamped shut for isolated one lung ventilation or opened for bronchoscopy or suctioning.

Double lumen ETs are designed with a sharp distal curve to facilitate placement to the right or left main stem bronchus. Since double lumen ETs have this sharp distal curve and are more bulky than standard ETs, they are often difficult to place with direct or even with the aid of video laryngoscopy. Consequently, many practitioners place a bronchoscope thru the double lumen ET, then place the bronchoscope in the correct main stem bronchus, and finally railroad the double lumen ET over the bronchoscope. The same bronchoscope is typically used in the tracheal lumen to check double lumen ET position after placement. These extra steps require special skills and extra time. When the double lumen ET cannot be placed, a bronchial blocker is typically used in its place. However, the double lumen ET is the preferred airway for OLV in most cases.

Double lumen ETs without steering capability with a fixed and integrated camera and camera lens cleaning system such as US20140128672A1 to Daher and Granot are well known but since there is no steering capability, it is not helpful with initial placement of the double lumen ET thru the vocal cords or steering into the correct bronchus—one of the most technically challenging procedures in thoracic anesthesia. Additionally, the camera is not removable (as it would be with the stylet of this invention) so it is subject to blurred monitor views from secretions on its camera lens. Rather than removing the camera lens and cleaning then reinserting the camera lens, an ineffective spray for the camera lens is the only option for cleaning heavy secretions from patients with pulmonary disease.

Since up and down steering is necessary to aid placement of the double lumen ET thru the vocal cords and left to right steering is needed to place the tip of the double lumen ET into the correct bronchus, this invention—which is able to navigate in multiple planes—overcomes the steering limitations of double lumen ETs in use today.

In this embodiment, the tip of the double lumen ET can optionally be flexible and wire reinforced to prevent kinking. The initial position can optionally be straight instead of curved to keep the images from the camera oriented correctly.

This embodiment of double lumen ET of the invention would not have to be physically turned 90 degrees for placement into a bronchus, leading to quicker, more accurate placement. Optionally, a secondary distal bronchial opening would be another embodiment for a right sided double lumen ET version to allow for ventilation of the lung's right upper lobe.

To facilitate control of steering and use of the proximal actuator, the double lumen ET's proximal extension piece is manufactured slightly longer and consequently the double lumen ET slightly shorter, with ability to disconnect from the ISO 15-22 mm connectors very close to the two double lumen ET lumens' point of separation proximally.

Further, with regarding to FIG. 33, each tube of the double lumen ET, and the stylet is sized such that a single length stylet can be used in both the tracheal tube and bronchial tube. With reference to FIG. 33, length BD of the tracheal tube should be the same as length AE of the bronchial tube, and consequently equal to the length of the stylet body from the actuator to the distal tip of the stylet.

There is also a need for steering left to right when using the device with a channeled video laryngoscope. This is due to the location of the channel on the right side of the laryngoscope. Advantageously the device can steer left and then right to avoid contact with the right sided laryngeal structures.

Left sided double lumen ETs are turned 90 degrees counterclockwise in the trachea after insertion past the vocal cords. Conversely, right sided double lumen tubes are turned 90 degrees clockwise in the trachea after insertion past the vocal cords.

Since the video monitor is detached from the video camera and typically located on a pole mount, a video camera located at the distal lumen of either the bronchial or tracheal lumen will have its image turned 90 degrees in the opposite direction and ultimately display an image 180 degrees from the camera's orientation and 90 degrees from the original image orientation.

Accordingly, the system of the invention has an optional spatial orientation/position sensor placed on the double lumen ET and/or stylet to keep track of the tube and/or its associated video camera's spatial positioning. By wired or wireless connection to the monitor, the image orientation can be chosen by the user as the following: 1) no monitor image adjustment; 2) monitor image adjustment to current camera orientation; or 3) monitor image adjustment to original image orientation. An illustration of these settings is shown in FIG. 34. These adjustments can be made in 90 degree intervals or in as little as less than 1 degree intervals.

This spatial orientation/position sensor and consequent video monitor image adjustment can be applied to any video monitor used with any video camera for Airway Management, including Bronchoscopes, Video Stylets, Video Laryngoscopes, Video ETs, Video Supraglottic Airways, Video Oral Airways, and the like.

Further, the double lumen ET may include one or more sensors for sensing physiological parameters of the subject, such as deep tissue oxygen sensors located along the tracheal and bronchial sections as shown in FIG. 35. The sensors (4100) may be disposed longitudinally along each tube of the ET (4000) or radially around each tube. The main trunk of the pulmonary artery lies directly anterior to the left main stem bronchus. This provides an ideal location for a deep tissue oxygen sensor to measure desaturated pulmonary arterial blood. Combined with cardiac output monitoring from thermodilution techniques (from a pulmonary artery catheter for example), or echocardiography techniques (transesophageal echo for example), or electrical impedance monitoring (endotracheal cardiac output monitor—(ECOM for example); and hemoglobin values; the patients rate of oxygen consumption can be easily determined by the Fick equation:

$$VO2=(CO*CaO2)-(CO*CvO2)$$

wherein:
VO2=rate of oxygen consumption,
CO=cardiac output,
CaO2=arterial oxygen content,
(1.34*Hg*SaO2+0.0031*PaO2),
CvO2=venous oxygen content, and
(1.34*Hg*SvO2+0.0031*PvO2).

Figure 40:
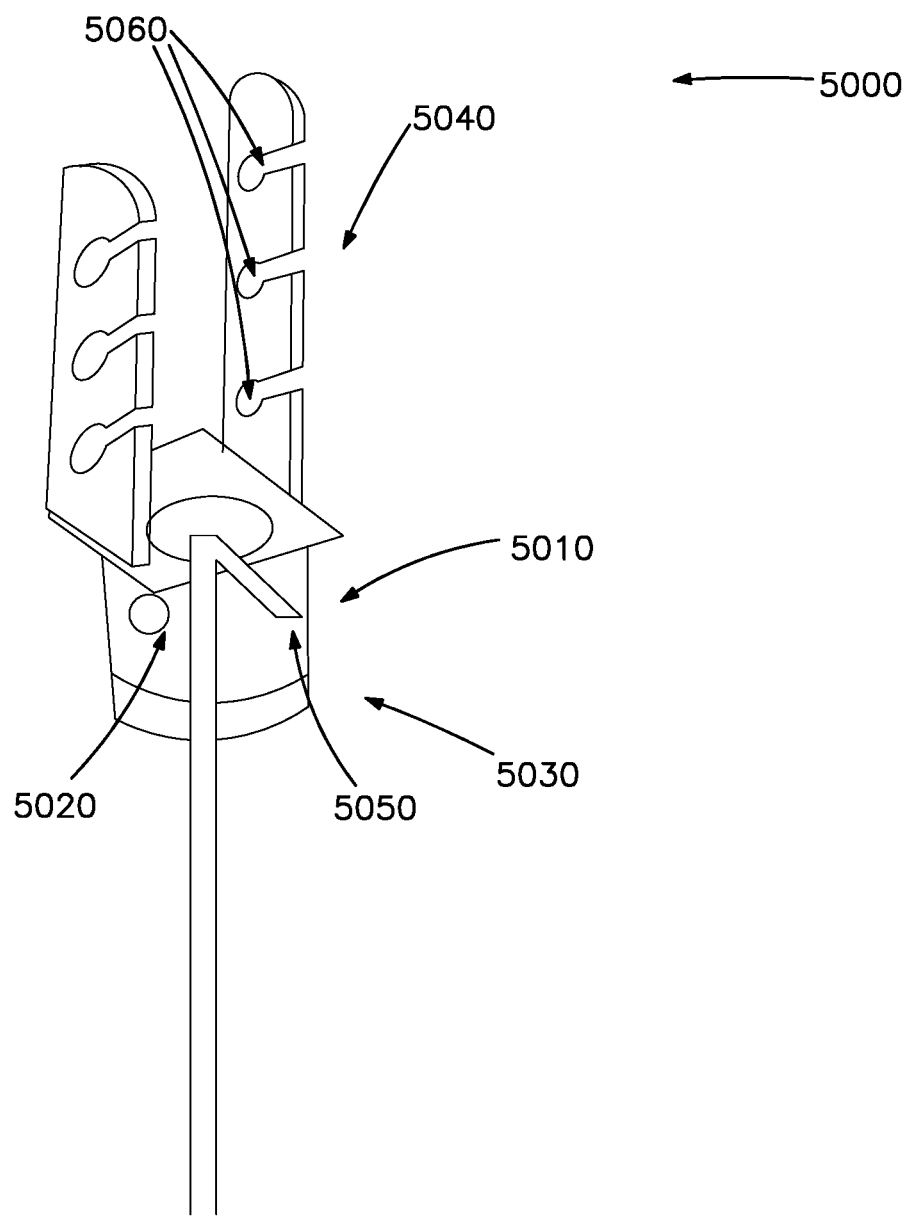
FIG. 40 illustrates an attachment and spacer device for coupling a stylet with an ET in one embodiment of the invention.

With reference to FIG. 40, shown is stylet attachment and spacer device (5000) for coupling a stylet with an ET. The device connects the stylet to the ET attachment portion (5010) and prevents rotational or longitudinal movement during use. As shown in FIG. 40, a port (5020) for a line to connect suction, 02, air, or medication is optionally included. Also shown is the proximal portion of the removable malleable rod (5030) in its housing in the stylet attachment portion (5040). The malleable rod has a tab (5050) bent at 90 degrees so the user can easily pull or push it into the desired location. This rod terminates distally at the stylets deflection point (not shown). Clearly seen are three points of attachment (5060) for the axle of the actuator control mechanism of the stylet. This variable height option allows for the use of a single stylet with several length endotracheal tubes.

Figure 41:
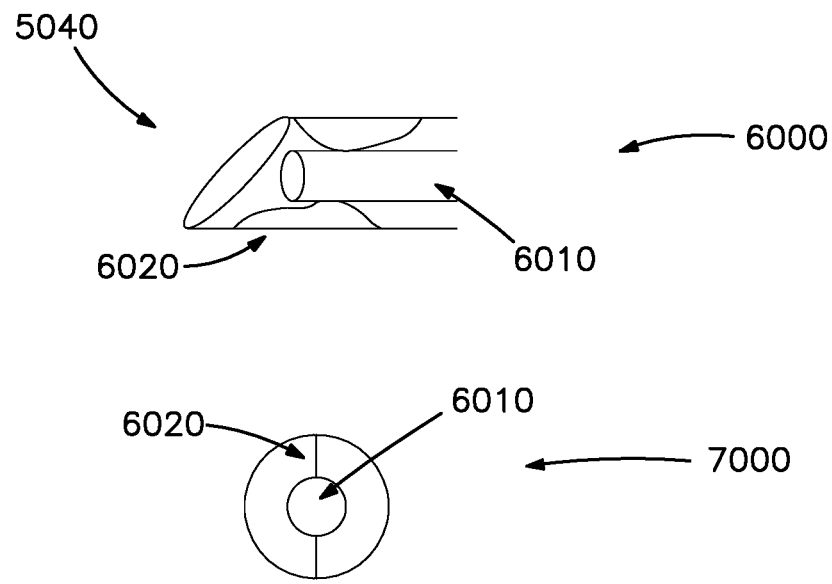
FIG. 41 are side and front views of a distal region of an ET tube having projections extending into the ET tube lumen from the inner wall of the tube for contacting and stabilizing the distal end of a stylet or endoscope inserted into the tube in one embodiment of the invention.

FIG. 41, shows a side view (lateral view) of an ET's distal end (6000) of the invention. Within the ET is a stylet or endoscope (6010) that is held in a stable position by projections (6020) extending from the inner wall of the tube and contacting the stylet or endoscope (6010). The design allows proper airflow through the endotracheal tube once the stylet or endoscope is removed. In embodiments, the inner wall of the tube may include any number of projections, including for example, 1, 2, 3, 4,5 ,6 ,7 8, 9, 10 or more projections extending into the tube lumen to stabilize the stylet or endoscope.

The front view of the ET's distal end (7000) is also shown in FIG. 41 with stylet or endoscope (6010) located within and reversibly secured by the projections (6020).

Figure 42:
FIG. 42 is an illustration of an ET having makings or color coding on the tube for making the depth of intubation conduit during intubation of a patient in one embodiment of the invention.

With reference to FIG. 42, the entire length of the ET of FIG. 41 is depicted. The ET includes a marking (8010) for identification of the depth of insertion in an intubation conduit where the ET's flexible bending segment exits the intubation conduit. Not shown are the flexible bending segment and stylet or endoscope.

Figure 43:
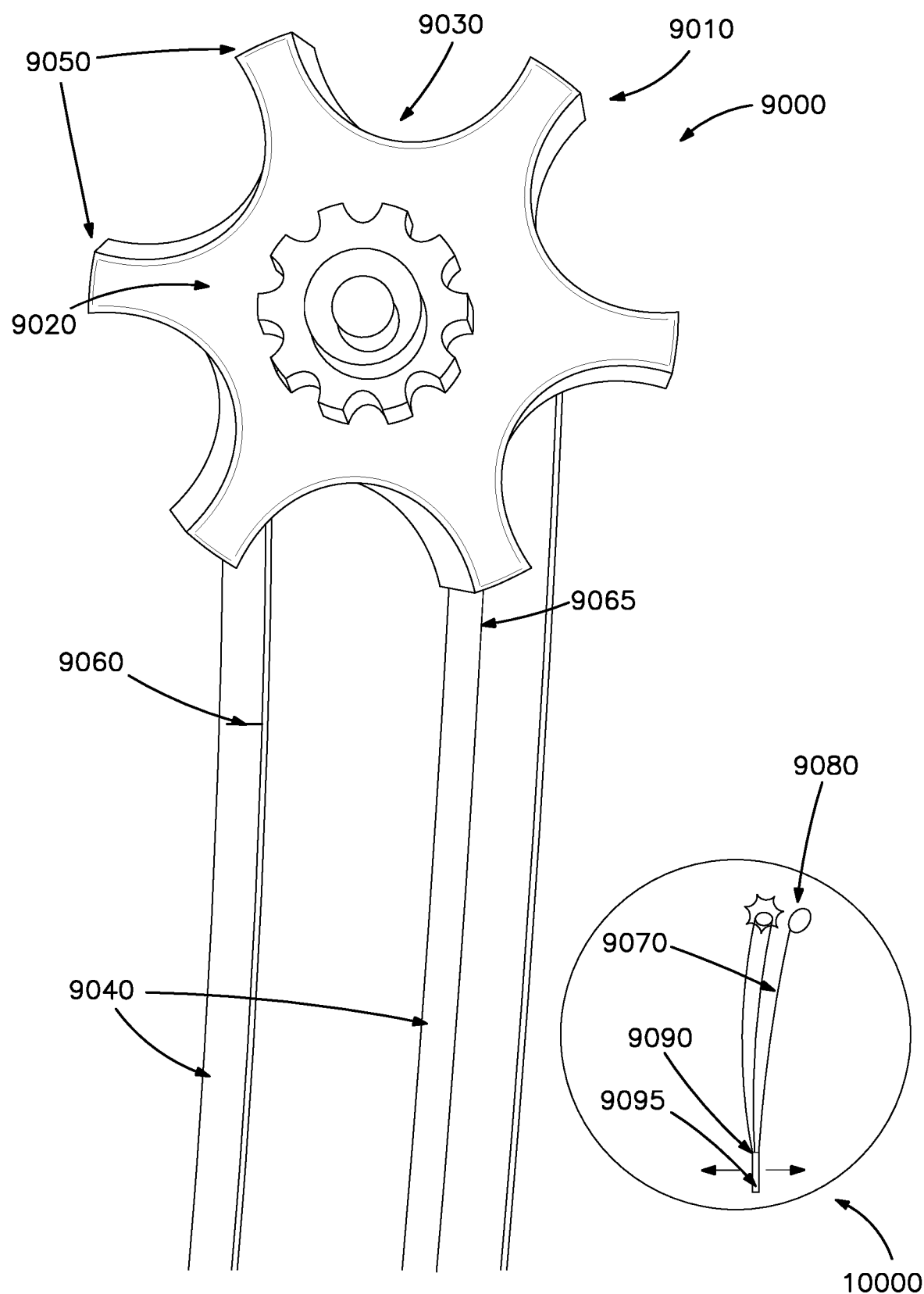
FIG. 43 is an illustration of stylet depicting operation of the actuator control mechanism and including markings for controlling the depth of intubation conduit during intubation of a patient in one embodiment of the invention.
Figure 44:
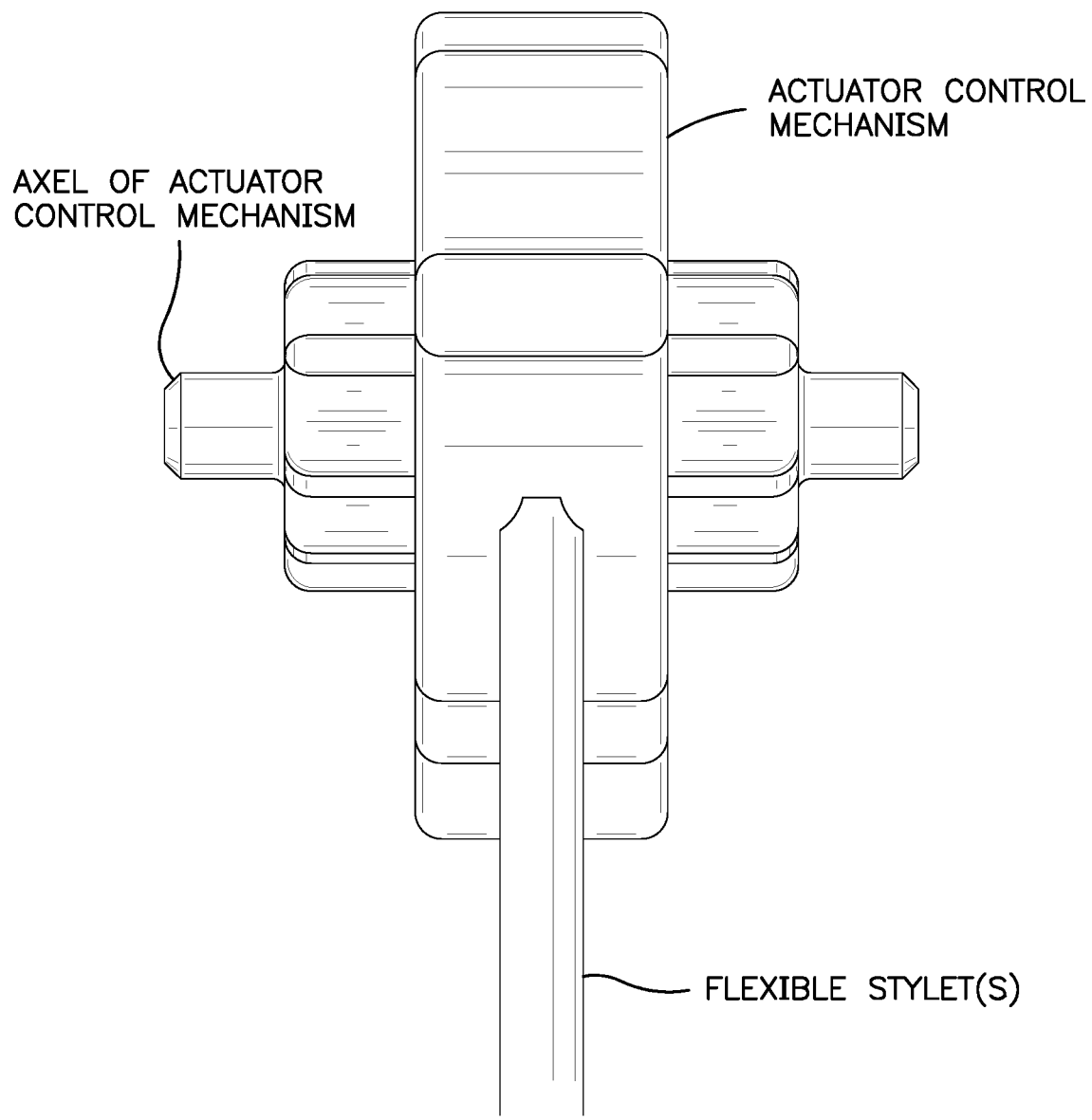
FIG. 44 is a view of a stylet having an actuator control mechanism having opposing pins extending perpendicular from the rotational axis of the control mechanism, the pins being configured to be disposed in the attachment and spacer device of FIG. 40, as well as two opposing sets of pressure receiving elements aligned to rotate the mechanism about its rotational axis, each pressure receiving element having recesses oriented toward the rotational axis in one embodiment of the invention.

With reference to FIG. 43 shown is the intubation device (e.g., stylet, 9000) in an embodiment where the actuator control mechanism (9010) comprises a wheel (9020) with several arcuate recesses (9030) about its circumference coupled to two flexible shafts (9040). The user's hand, typically thumb and forefinger, apply force (A and B) to the pressure receiving elements (9050) located about the circumference of the wheel (9020). These forces are transmitted to the flexible shafts (9040) and result in angular deflection at the deflection point of the stylet. For example, if Force A is applied by a thumb or forefinger to one of the pressure receiving elements (9050), the distal tip of the stylet and its surrounding endotracheal tube will retroflex. Conversely, if Force B is applied by a thumb or forefinger to one of the pressure receiving elements (9050), the distal tip of the stylet and its surrounding endotracheal tube will flex. The movement (flexion and retroflexion) at the distal tip of the endotracheal tube can be accomplished with individual or simultaneous forces on more than one pressure receiving element (9050). The flexible shafts (9040) can also function independently of each other with separate couplings to the actuator control mechanism (9010).

Also shown in FIG. 43 is the removable malleable rod (9065) and its lumen located in one of the flexible shafts (9040). This allows the intubation device to be temporarily shaped proximally and angularly deflected distally in either direction. Additionally, one or more markings (9060) are included on one or more of the shafts (9040) of the stylet to indicate the depth of the intubation conduit during intubation.

FIG. 43 further includes diagram (10000) of the intubation device (9000) with the addition of a third flexible shaft (9070) that enables steering in a third direction. In this embodiment, the third flexible shaft (9070) is a wire that has a proximal loop (9080) that can be pulled with a user's digit. The deflection point (9090) of the stylet is illustrated which includes a plastic living hinge or standard hinge configuration. At the distal end of the stylet is the optional camera and illumination source (9095) with power and wiring omitted.

In another aspect, the invention provides a kit. The kit may include an imaging system or intubation device as described herein. The kit may further include instructions for obtaining images of a confined space, such as an airway. In some embodiments, the kit further includes one or more spacer elements, an ET, a malleable rod, a display, or a combination thereof.

In another aspect, the invention provides a kit. The kit may include a stylet and single or double lumen ET as described herein. The kit may further include instructions for obtaining images of a confined space, such as an airway. In some embodiments, the kit further includes a malleable rod, one or more displays, or a combination thereof.

The present invention is useful in the visualization of any space, particularly confined spaces not amenable to direct visualization. Therefore, the present invention is useful in a variety of fields including but not limited to medical treatment and diagnosis, surveillance including law enforcement and military applications, inspection of machinery without disassembly and automotive applications. As such, the invention provides a method of imaging a confined space. The method includes inserting a stylet or device of the disclosure into the confined space, and visualizing the space via an image acquisition element before, during or after insertion of the device into the confined space, thereby imaging the confined space.

The present invention is useful for surveillance, particularly in the fields of law enforcement or military applications. For example, the image conduit may be threaded through very small spaces to enable visualization of the interiors of rooms or confuted spaces while minimizing the exposure of the operator to potentially dangerous situations. For example, the present invention may be used to visualize spaces which may contain explosive devices or contraband. Commercially available image sensors are capable of recognizing light outside the visible spectrum or in low or zero lux conditions. Consequently, the present invention may be useful as a "night vision" surveillance system to enable the operator to obtain an image of a space in the substantial absence of ambient light. As previously discussed, the illumination source of the present invention may provide illumination in a frequency range outside the visible spectrum and such non-visible light sources may be employed to invisibly illuminate an area and enhance such "night vision" capabilities.

The present invention is also useful in a variety of automotive applications. For example, the image conduit may be threaded through small spaces such as spark plug holes to enable visualization of the interiors of cylinders, intake and/or exhaust valves, intake and exhaust systems, HVAC systems, to inspect the status and operation of enclosed mechanical mechanisms without disassembly (e.g., window mechanisms, door locking mechanisms, transmissions, differentials, fuel systems, and the like), assess the state of replaceable parts such as brake linings or clutches, and the like.

Although the invention has been described with reference to the above example, it will be understood that modifications and variations are encompassed within the spirit and scope of the invention. Illustrative examples of the invention are attached herein as Exhibit A which is herein incorporated by reference in its entirety. Accordingly, the invention is limited only by the following claims.

What is claimed is:

1. A stylet comprising:
   a) an elongated stylet having a malleable rod removably housed within the stylet, the stylet having an opening in a manually operable actuator at a proximal end of the stylet for insertion and removal of the malleable rod, the stylet further comprising:
      i) a flexible proximal portion having a predetermined shape defined by the malleable rod when inserted in the stylet; and
      ii) a distal tip, the distal tip being capable of deflection when the malleable rod is inserted in the flexible proximal portion of the stylet; and
   b) the manually operable actuator configured to receive a force from a user at the proximal end of the stylet to control a deflection angle of the distal tip when the malleable rod is inserted in the flexible proximal portion of the stylet,
   wherein the stylet and the malleable rod are configured to engage each other upon insertion of the malleable rod into the flexible proximal portion of the stylet, and
   wherein, the stylet and the malleable rod are configured such that upon withdrawal of the malleable rod from the flexible proximal portion of the stylet, the malleable rod traverses a cross sectional plane of the actuator that is perpendicular to the malleable rod.

2. The stylet of claim 1, wherein the stylet further comprises an image acquisition element, an illumination source, or combination thereof.

3. The stylet of claim 2, wherein the stylet comprises an image acquisition element and an illumination source.

4. The stylet of claim 3, wherein the stylet further comprises a display monitor in electronic communication with the image acquisition element.

5. The stylet of claim 1, further comprising an endotracheal tube operably coupled to the stylet.

6. A method of intubating a patient comprising intubating the patient with the stylet of claim 1, in combination with an endotracheal tube.

* * * * *